United States Patent
Tomiyama et al.

(10) Patent No.: US 7,691,898 B2
(45) Date of Patent: Apr. 6, 2010

(54) PHOSPHONIC ACID DERIVATIVES AND THE TREATING AGENTS OF DISEASES RELATED HYPERPHOSPHATEMIA

(75) Inventors: Hiroshi Tomiyama, Sakaki-machi (JP); Masayuki Yokota, Chikuma (JP); Kazuo Tokuzaki, Sakaki-machi (JP); Ryoko Tomita, Chikuma (JP)

(73) Assignee: Kotobuki Pharmaceutical Co., Ltd., Nagano (JP)

( * ) Notice: Subject to any disclaimer, the term of this patent is extended or adjusted under 35 U.S.C. 154(b) by 129 days.

(21) Appl. No.: 11/664,830

(22) PCT Filed: Oct. 5, 2005

(86) PCT No.: PCT/JP2005/018739

§ 371 (c)(1),
(2), (4) Date: Apr. 5, 2007

(87) PCT Pub. No.: WO2006/038719

PCT Pub. Date: Apr. 13, 2006

(65) Prior Publication Data

US 2008/0119441 A1    May 22, 2008

(30) Foreign Application Priority Data

Oct. 8, 2004    (JP)    ............... 2004-296200

(51) Int. Cl.
*A61K 31/381*    (2006.01)
*C07D 333/46*    (2006.01)
*C07F 9/30*    (2006.01)

(52) U.S. Cl. ..................... 514/438; 549/70; 562/23; 562/24

(58) Field of Classification Search .......... 514/438; 549/70; 562/23, 24
See application file for complete search history.

(56) References Cited

U.S. PATENT DOCUMENTS

| | | | |
|---|---|---|---|
| 2,596,660 | A | 5/1952 | Dickey |
| 4,517,010 | A | 5/1985 | Theissen |
| 5,208,235 | A | 5/1993 | Poss |
| 6,174,874 | B1 | 1/2001 | Wang et al. |
| 6,465,687 | B1 | 10/2002 | Li et al. |
| 6,545,022 | B1 | 4/2003 | Bryans et al. |
| 2005/0065068 | A1 | 3/2005 | Kumagai et al. |

FOREIGN PATENT DOCUMENTS

| | | |
|---|---|---|
| JP | 56-127335 | 10/1981 |
| JP | 03-133964 | 6/1991 |
| JP | 2002-508352 | 3/2002 |
| JP | 2002-513422 | 5/2002 |
| JP | 2002-526505 | 8/2002 |
| JP | 2003-508446 | 3/2003 |

OTHER PUBLICATIONS

STN preliminary search report-U.S. Appl. No. 11/664,830.*
D'Auria et al., Synthetic Communications, 1992, 22(5), p. 699-727, Abstract from STN search report.*
Haelters et al., Phosphorus and Sulfur and Related Elements, 1988, 37(1-2), pp. 41-63, (Abstract and STN search report).*
STN search-U.S. Appl. No. 11/664,830-Aug. 6, 2009.*
"Structure-Activity Relationships in a Series of 5-[(2,5-Dihydroxybenzyl)amino]salicylate Inhibitors of EGF-Receptor-Associated Tyrosine Kinase: Importance of Additional Hydrophobic Aromatic Interactions", by H. Chen et al, *Journal of Medicinal Chemistry*, 1994, vol. 37, No. 6, pp. 845-859.
"Reactions of carbine intermediates from the reaction of trialkyl phosphites with dialkyl benzoylphosphonates: intramolecular cyclisations of 2-substituted dialkyl benzoylphosphonates", by D. Vaughn Griffiths et al, *Journal of the Chemical Society*, 1996, Perkin Transaction 1, No. 6, pp. 555-561.
"Mechanism of Inactivation of γ-Aminobutyric Acid Aminotransferase by (S)-4-Amino-4,5-dihydro-2-thiophenecarboxylic Acid", by M. Fu et al, *Journal of American Chemical Society*, 1999, vol. 121, No. 34, pp. 7751-7759.

\* cited by examiner

*Primary Examiner*—Yong Chu
(74) *Attorney, Agent, or Firm*—Flynn, Thiel, Boutell & Tanis, P.C.

(57) ABSTRACT

This invention related to a series of new phosphonic acid derivatives having anti-hyperphosphatemia activity.

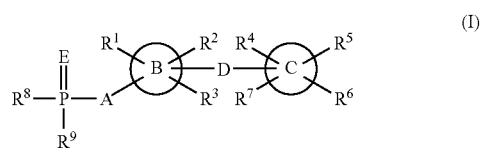

(I)

wherein: A is selected from $-(CH_2)_n-$, $-CO-$, $-(CH_2)_n-CO-(CH_2)_m-$, $-(CH_2)_n-CS-(CH_2)_m-$ or a branched alkylene group, B ring and C ring are selected from a benzene ring, naphthalene ring, azulene ring or, heterocycle or fused heterocycle compound, D is $-(CH_2)_{(n+1)}-$, $-(CH2)-O-(CH_2)_m-$, $-(CH_2)-S(O)_o-(CH_2)_m-$, $-CF_3$ or $-(CH_2)_n-NR^{10}-(CH_2)_m-$ wherein a D ring is connected with the carbon atom composing the C ring, E is selected from an oxygen atom or a sulfur atom, P is a phosphine atom, $R^1 \sim R^7$, wherein $R^1$ and $R^2$, $R^4$ and $R^5$ are joined together with neighbored carbon atom to form 5~7 membered saturated or unsaturated hydrocarbon ring, or 5~6 membered fused heterocycle, $R^1$, $R^2$ and $R^3$ are not a hydrogen atom if the B ring is a benzene ring and may be the same or different and are substituents, $R^8$ and $R^9$ are may be the same or different and are substituents, $R^{10}$ is an alkyl group, n and m are 0-10 and o is 0-2.

3 Claims, No Drawings

PHOSPHONIC ACID DERIVATIVES AND THE TREATING AGENTS OF DISEASES RELATED HYPERPHOSPHATEMIA

CROSS-REFERENCE TO RELATED APPLICATIONS

This application is a nationalized application filed under 35 USC 371 of PCT/JP2005/018739, filed on Oct. 5, 2005.

FIELD OF THE INVENTION

The present invention relates to novel phosphonic acid derivatives. In detail, the present invention relates to phosphonic acid derivatives having a serum phosphate concentration-lowering activity or their pharmaceutical acceptable salts or pharmaceutical compositions thereof.

BACKGROUND OF THE INVENTION

Recently, since patients with diabetes mellitus have markedly increased, hemodialysis with the progression of diabetic nephropathy has increased. These patients with renal failure, inhibited renal phosphate excretion, show hyperphosphatemia because serum phosphate cannot be sufficiently removed by hemodialysis. Hyperphosphatemia is a causative factor of secondary hyperparathyroidism and renal osteodystrophy by an excessive secretion of parathyroid hormone, and it also induces ectopic calcification in cardiovascular system by increase and accumulation of calcium phosphate, considering one of the causes of the cardiovascular diseases.

As the anti-hyperphosphatemia agent, various metallic salts (e.g. aluminum preparation, calcium preparation, rare earth metal salts such as Lanthanum Carbonate) and polymer preparation such as Sevelamer Hydrochloride and cholesterol sequestrants have been marketed and researched. However, these drugs have some problems such as large amounts of dosage required, expression of adverse effects such as gastrointestinal disorder, and poor specificity of phosphate adsorption.

As can be seen from the above discussion, more effective and high safety new serum phosphate lowering agents are needed. Recently, 2'-phosphophloretin (2'-PP) having a Na+ dependent phosphate transporter inhibitory effect is reported (Biochem. Biophys. Res. Commu., 301 (1), 8-12, 2003). It is thought that in vivo activity of the compound is insufficient due to it hydrolyzing by an alkaline phosphatase easily. Therefore, it is hoped that the compound had a potent activity and in vivo efficacy.

This invention aims to offer the newly phosphonate derivatives or the medicinally acceptable salts that have serum phosphate lowering effects.

DISCLOSURE OF INVENTION

This invention related to a series of new phosphonic acid derivatives, which are anti-hyperphosphatemia agents.

The compounds of the present invention comprise phosphonic acid derivatives represented by general formula (I) and their pharmaceutical acceptable salts

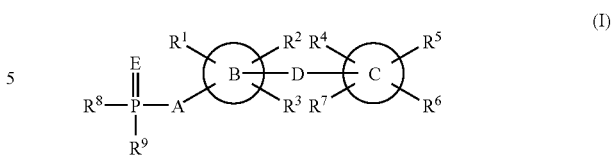

[wherein: A is selected from $-(CH_2)_n-$, $-CO-$, $-(CH_2)_n-CO-(CH_2)_m-$, $-(CH_2)_n-CS-(CH_2)_m-$ or branched alkylene group. B ring is selected from benzene ring, naphthalene ring, azulene ring or, heterocycle or fused heterocycle containing nitrogen, oxygen or sulfur atom and not containing nitrogen atom more than 1. The C ring may be the same or different from the B ring and is selected from a benzene ring, a naphthalene ring, an azulene ring or, a heterocycle or fused heterocycle compound containing a nitrogen, oxygen or sulfur atom.

D is selected from $-(CH_2)_{(n+1)}-$, or $-CF_3$. D ring is connected with the carbon atom composing B ring and with the carbon atom composing C ring.].

E is selected from an oxygen atom or sulfur atom. P is a phosphine atom.

$R^1 \sim R^7$ (however, $R^1$ and $R^2$, $R^4$ and $R^5$ can be joined together with neighboring carbon atoms to form 5~7 membered saturated or unsaturated hydrocarbon rings, or 5~6 membered fused heterocycles. $R^1$, $R^2$ and $R^3$ are not a hydrogen atom if the B ring is a benzene ring) may be the same or different and are selected from a hydrogen atom, a halogen atom, a nitro group, a cyano group, a straight-chain or branched-chain alkyl group of C1-20, a straight-chain or branched-chain haloalkyl group of C1-20, a straight-chain or branched-chain haloalkoxy group of C1-20, an unsubstituted or substituted aryl group, a heterocycle or fused heterocycle compound containing a nitrogen, oxygen or sulfur atom, $-(CH_2)_n-OH$, $-O-(CH_2)_{(n+1)}-OH$, an $-(CH_2)_n-O$-straight-chain or branched-chain alkyl group of C1-20, an $-(CH_2)_n$-unsubstituted or substituted aryl group, an $-O-(CH_2)_{(n+1)}-$ unsubstituted or substituted aryl group, an $-(CH_2)_n-S(O)_o$-straight-chain or branched-chain alkyl group of C1-20, an $-O-(CH_2)_{(n+1)}-S(O)_o$-straight-chain or branched-chain alkyl group of C1-20, an $-(CH_2)_n-S(O)_o$-unsubstituted or substituted aryl group, an $-O-(CH_2)_{(n+1)}-S(O)_o$-unsubstituted or substituted aryl group, $-(CH_2)_n-COOR^{11}$, $-O-(CH_2)_n-COOR^{11}$, $-(CH_2)_n-SO_3R^{11}$, $-O-(CH_2)_n-SO_3R^{11}$ [wherein $R^{11}$ is selected from a hydrogen atom, or a straight-chain or branched-chain alkyl group of C1-20.], $-(CH_2)_n-CONR^{12}R^{13}$, $-O-(CH_2)_n-CONR^{12}R^{13}$, $-(CH_2)_n-SO_2NR^{12}R^{13}$, $-O-(CH_2)_n-SO_2NR^{12}R^{13}$ [$R^{12}$ and $R^{13}$ are a hydrogen atom, or straight-chain or branched-chain alkyl group of C1-20.], an $-(CH_2)_n-CO$-branched-chain alkyl group of C1-20, an $-O-(CH_2)_n-CO$-branched-chain alkyl group of C1-20, an $-(CH_2)_n-CO$-unsubstituted or substituted aryl group, an $-O-(CH_2)_n-CO$-unsubstituted or substituted aryl group, an amino group, a monosubstituted amino group, a disubstituted amino group, a trisubstituted amino group, a tetrasubstituted amino group, an $-O-(CH_2)_{(n+1)}-O$-amino group, an $-O-(CH_2)_{(n+1)}-O$-monosubstituted amino group, an $-O-(CH_2)_{(n+1)}-O$-disubstituted amino group, an $-O-(CH_2)_{(n+1)}-O$-trisubstituted amino group, an $-O-(CH_2)_{(n+1)}-O$-tetrasubstituted amino group, a substituted amino group wherein the substituent is a straight-chain or branched-chain alkyl group of C1-20, a straight-chain or branched-chain alkanoyl group of C1-20, an unsubstituted or substituted arylcarbonyl group, a straight-chain or branched-chain alkylsulfonyl group of C1-20, an unsubstituted or substituted arylsulfonyl group or straight-chain or branched-chain alkoxycarbonyl group of C1-20.].

$R^8$ and $R^9$ may be the same or different and are selected from a hydroxyl group, a straight-chain or branched-chain alkoxy group of C1-20, a thiol group, a straight-chain, branched-chain thioalkyl group of C1-20 or an amino group.

n and m are 0-10. o is 0-2.].

FIELD OF INDUSTRIAL APPLICATION

Phosphonic acid derivatives represented by general formula (I) have serum phosphate concentration-lowering activity.

BEST MODE FOR CARRYING OUT THE INVENTION

Phosphonic acid derivatives represented by general formula (I) have serum phosphate concentration-lowering activity. A class of compound particular interest consists of those compounds of formula (I).

A is bond, —$CH_2$—, —$(CH_2)_2$—, —$(CH_2)_3$—, —$(CH_2)_4$—, —$(CH_2)_5$—, —CO—, —$COCH_2$—, —$CH_2CO$—, —$CH_2COCH_2$—, —CS—, —$CSCH_2$—, —$CH_2CS$—, —$CH_2CSCH_2$—.

The B ring is selected from a benzene ring, naphthalene ring, azulene ring, or heterocycle or fused heterocycle containing a nitrogen, oxygen or sulfur atom and not containing more than one nitrogen atom such as an unsubstituted or substituted thiophene ring, a furan ring, a pyrole ring, a pyridine ring, a thiazole ring, a benzothiophene ring, a benzofuran ring, an indole ring, a benzothiazole ring or a benzodioxane ring.

The C ring may be the same as or different from the B ring and is selected from a benzene ring, naphthalene ring, azulene ring, or heterocycle or fused heterocycle containing a nitrogen, oxygen or sulfur atom such as an unsubstituted or substituted thiophene ring, a furan ring, a pyrole ring, a pyridine ring, a thiazole ring, an imidazole ring, a pyrazole ring, a pyrimidine ring, a pyrazine ring, a pyridazine ring, a benzothiophene ring, a benzofuran ring, an indole ring, a benzothiazole ring, a benzimidazole ring or a benzodioxane ring.

D is —$CH_2$—, —$(CH_2)_2$—, —$(CH_2)_3$—, —$(CH_2)_4$—, —$(CH_2)_5$—, $CF_2$—. E is selected from an oxygen atom or a sulfur atom.

$R^1$~$R^7$ may be the same or different and are selected from a hydrogen atom, a halogen atom (fluorine atom, chlorine atom, bromine atom, iodine atom), a nitro group, a cyano group, a straight-chain or branched-chain alkyl group such as a methyl group, an ethyl group, a propyl group, an isopropyl group, a cyclopropyl group, a butyl group, an isobutyl group, a cyclobutyl group, a pentyl group, a cyclopentyl group, a hexyl group, an octyl group, a nonyl group or a decanyl group, a straight-chain or branched-chain haloalkyl group such as a monofluoromethyl group, a difluoromethyl group, a trifluoromethyl group, a 2,2,2-trifluoroethyl group, a pentafluoroethyl group, a monochloromethyl group, a dichloromethyl group, a trichloromethyl group or a 2,2,2-trichloroethyl group, a straight-chain or branched-chain haloalkoxy group such as a monofluoromethoxy group, a difluoromethoxy group, a trifluoromethoxy group, a 2,2,2-trifluoroethoxy group, a pentafluoroethoxy group, a monochloromethoxy group, a dichloromethoxy group, a trichloromethoxy group or a 2,2,2-trichloroethoxy group, an unsubstituted or substituted aryl group such as a methyoxyphenyl group, a chlorophenyl group or a methylphenyl group, a heterocycle or fused heterocycle containing nitrogen, oxygen or sulfur atom such as unsubstituted or substituted thiophene ring, furan ring, pyrole ring, pyridine ring, pyrazole ring, pyrimidine ring, pyrazine ring, pyridazine ring, benzothiophene ring, benzofuran ring, indole ring, benzothiazole ring, benzimidazole ring, quinoline ring or isoquinoline ring, —$(CH_2)_n$OH such as —$CH_2OH$, —$(CH_2)_2$—OH, $(CH_2)_3OH$, —$(CH_2)_4OH$ or —$(CH_2)_5OH$, —O—$(CH_2)_{(n+1)}OH$ such as —$OCH_2OH$, —O—$(CH_2)_2OH$, —$O(CH_2)_3OH$, —$O(CH_2)_4OH$ or —O—$(CH_2)_5OH$, —$(CH_2)_n$—O-straight-chain or branched-chain alkyl group such as methoxy group, ethoxy group, propoxy group, isopropoxy group, cyclopropoxy group, butoxy group, isobutoxyl group, cyclobutoxy group, pentoxy group, cyclopentoxy group, heptyloxy group, octyloxy group, nonyloxy group or decanyloxy group, —$CH_2OCH_3$, —$(CH_2)_2OCH_3$, —$(CH_2)_3OCH_3$, —$CH_2OCH_2CH_3$, —$(CH_2)_2OCH_2CH_3$ or —$(CH_2)_3OCH_2CH_3$, —O—$(CH_2)_{(n+1)}$O-straight-chain or branched-chain alkyl group such as —$OCH_2OCH_3$, —$O(CH_2)_2OCH_3$, —$O(CH_2)_3OCH_3$, —$OCH_2OCH_2CH_3$, —$O(CH_2)_2OCH_2CH_3$ or —$O(CH_2)_3OCH_2CH_3$, —$(CH_2)_n$-unsubstituted or substituted aryl group such as benzene ring, naphthalene ring, azulene ring, —$CH_2Ph$, —$(CH_2)_2Ph$, —$(CH_2)_3Ph$, —$(CH_2)_4Ph$ or —$(CH_2)_5Ph$, —$O(CH_2)_{(n+1)}$-unsubstituted or substituted aryl group such as —$OCH_2Ph$, —$O(CH_2)_2Ph$, —$O(CH_2)_3Ph$, —$O(CH_2)_4Ph$ or —$O(CH_2)_5Ph$, —$(CH_2)_n$—O-unsubstituted or substituted aryl group such as phenoxy group, methylphenoxy group, methoxyphenoxy group, chlorophenoxy group, —$CH_2OPh$, —$(CH_2)_2OPh$, —$(CH_2)_3OPh$, —$(CH_2)_4OPh$ or —$(CH_2)_5OPh$, —$O(CH_2)_{(n+1)}$—O-unsubstituted or substituted aryl group such as —$OCH_2OPh$, —$O(CH_2)_2OPh$, —$O(CH_2)_3OPh$, —$O(CH_2)_4OPh$ or —$O(CH_2)_5OPh$, —$(CH_2)_n$—$S(O)_o$-straight-chain or branched-chain alkyl group such as methylthio group, ethylthio group, propylthio group, isopropylthio group, cyclopropylthio group, butylthio group, isobutylthio group, cyclobutylthio group, pentylthio group, cyclopentylthio group, hexylthio group, heptylthio group, octylthio group, nonylthio group, decanylthio group, —$CH_2SCH_3$, —$CH_2SCH_2CH_3$, —$(CH_2)_2SCH_3$, —$(CH_2)_2SCH_2CH_3$, —$(CH_2)_3SCH_3$, —$(CH_2)_3SCH_2CH_3$, —$CH_2SOCH_3$, —$CH_2SOCH_2CH_3$, —$(CH_2)_2SOCH_3$, —$(CH_2)_2SOCH_2CH_3$, —$(CH_2)_3SOCH_3$, —$(CH_2)_3SOCH_2CH_3$, —$CH_2SO_2CH_3$, —$CH_2SO_2CH_2CH_3$, —$(CH_2)_2SO_2CH_3$, —$(CH_2)_2SO_2CH_2CH_3$, —$(CH_2)_3SO_2CH_3$, —$(CH_2)_3SO_2CH_2CH_3$, methylsulfonyl group, ethylsulfonyl group, propylsulfonyl group, isopropylsulfonyl group, cyclopropylsulfonyl group, butylsulfonyl group, isobutylsulfonyl group, cyclobutylsulfonyl group, pentylsulfonyl group or cyclopentylsulfonyl group, —O—$(CH_2)_{(n+1)}$—$S(O)$—$_o$-straight-chain or branched-chain alkyl group such as —$OCH_2SCH_3$, —$OCH_2SCH_2CH_3$, —$O(CH_2)_2SCH_3$, —$O(CH_2)_2SCH_2CH_3$, —$O(CH_2)_3SCH_3$, —$O(CH_2)_3SCH_2CH_3$, —$OCH_2SOCH_3$, —$OCH_2SOCH_2CH_3$, —$O(CH_2)_2SOCH_3$, —$O(CH_2)_2SOCH_2CH_3$, —$O(CH_2)_3SOCH_3$, —$O(CH_2)_3SOCH_2CH_3$, —$OCH_2SO_2CH_3$, —$OCH_2SO_2CH_2CH_3$, —$O(CH_2)_2SO_2CH_3$, —$O(CH_2)_2SO_2CH_2CH_3$, —$O(CH_2)_3SO_2CH_3$ or —$O(CH_2)_3SO_2CH_2CH_3$, —$(CH_2)_n$—$S(O)_o$-unsubstituted or substituted aryl group such as phenylthio group, methylphenylthio group, methoxyphenylthio group, chlorophenylthio group, —$CH_2SPh$, —$CH_2SOPh$, —$CH_2SO_2Ph$, —$(CH_2)_2SPh$, —$(CH_2)_2SOPh$ or —$(CH_2)_2SO_2Ph$, —$O(CH_2)_{(n+1)}$—$S(O)_o$-unsubstituted or substituted aryl group such as —$OCH_2SPh$, —$OCH_2SOPh$, —$OCH_2SO_2Ph$, —$O(CH_2)_2SPh$, —$O(CH_2)_2SOPh$, —O(CH$_2$)$_2$SO$_2$Ph, benzenesulfonyl group, toluenesulfonyl group, methoxybenzenesulfonyl group or chlorobenzenesulfonyl group, —(CH$_2$)$_n$—COOR$^{11}$ such as —COOH, —CH$_2$COOH, —(CH$_2$)$_2$COOH, —(CH$_2$)$_3$COOH, —(CH$_2$)$_4$COOH, —(CH$_2$)$_5$COOH, —CH$_2$COOCH$_3$, —(CH$_2$)$_2$COOCH$_3$, —CH$_2$COOCH$_2$CH$_3$, —(CH$_2$)$_2$COOCH$_2$CH$_3$, methoxycarbonyl group, ethoxycarbonyl group, propoxycarbonyl group, isopropoxycarbonyl group, cyclopropoxycarbonyl group, butoxycarbonyl group, isobutoxycarbonyl group, cyclobutoxycarbonyl group, pentyloxycarbonyl group or cyclopentyloxycarbonyl group, —O(CH$_2$)$_n$—COOR$^{11}$ such as —OCH$_2$COOH, —O(CH$_2$)$_2$COOH, —O(CH$_2$)$_3$COOH, —O(CH$_2$)$_4$COOH, —O(CH$_2$)$_5$COOH, —OCH$_2$COOCH$_3$, —O(CH$_2$)$_2$COOCH$_3$, —OCH$_2$COOCH$_2$CH$_3$, —O(CH$_2$)$_2$COOCH$_2$CH$_3$, —(CH$_2$)—SO$_3$R$^{11}$ such as —SO$_3$H, —CH$_2$SO$_3$H, —(CH$_2$)$_2$SO$_3$H, —(CH$_2$)$_3$SO$_3$H, —(CH$_2$)$_4$SO$_3$H, —(CH$_2$)$_5$SO$_3$H, —CH$_2$SO$_3$CH$_3$, —(CH$_2$)$_2$SO$_3$CH$_3$, —CH$_2$SO$_3$CH$_2$CH$_3$ or —(CH$_2$)$_2$SO$_3$CH$_2$CH$_3$, —O(CH$_2$)—SO$_3$R$^{11}$ such as —OCH$_2$SO$_3$H, —O(CH$_2$)$_2$SO$_3$H, —O(CH$_2$)$_3$SO$_3$H, —O(CH$_2$)$_4$SO$_3$H, —O(CH$_2$)$_5$SO$_3$H, —OCH$_2$SO$_3$CH$_3$, —O(CH$_2$)$_2$SO$_3$CH$_3$, —OCH$_2$SO$_3$CH$_2$CH$_3$, —O(CH$_2$)$_2$SO$_3$CH$_2$CH$_3$, —(CH$_2$)$_n$—CONR$^{12}$R$^{13}$ such as —CONH$_2$, —CONHCH$_3$, —CON(CH$_3$)$_2$, —CH$_2$CONH$_2$, —(CH$_2$)$_2$CONH$_2$, —(CH$_2$)$_3$CONH$_2$, —CH$_2$CONHCH$_3$, —(CH$_2$)$_2$CONHCH$_3$, —(CH$_2$)$_3$CONHCH$_3$, —CH$_2$CON(CH$_3$)$_2$, —(CH$_2$)$_2$CON(CH$_3$)$_2$, —CH$_2$CONHCH$_2$CH$_3$, —(CH$_2$)$_2$CONHCH$_2$CH$_3$, —(CH$_2$)$_3$CONHCH$_2$CH$_3$, —CH$_2$CON(CH$_2$CH$_3$)$_2$ or —(CH$_2$)$_2$CON(CH$_2$CH$_3$)$_2$, —O—(CH$_2$)$_n$—CONR$^{12}$R$^{13}$ such as —OCH$_2$CONH$_2$, —O(CH$_2$)$_2$CONH$_2$, —O(CH$_2$)$_3$CONH$_2$, —OCH$_2$CONHCH$_3$, —O(CH$_2$)$_2$CONHCH$_3$, —O(CH$_2$)$_3$CONHCH$_3$, —OCH$_2$CON(CH$_3$)$_2$, —O(CH$_2$)$_2$CON(CH$_3$)$_2$, —OCH$_2$CONHCH$_2$CH$_3$, —O(CH$_2$)$_2$CONHCH$_2$CH$_3$, —O(CH$_2$)$_3$CONHCH$_2$CH$_3$, —OCH$_2$CON(CH$_2$CH$_3$)$_2$, or —O(CH$_2$)$_2$CON(CH$_2$CH$_3$)$_2$, —(CH$_2$)$_n$—SO$_2$NR$^{12}$R$^{13}$ such as —SO$_2$NH$_2$, —SO$_2$NHCH$_3$, —SO$_2$N(CH$_3$)$_2$, —CH$_2$SO$_2$NH$_2$, —(CH$_2$)$_2$SO$_2$NH$_2$, —(CH$_2$)$_3$SO$_2$NH$_2$, —CH$_2$SO$_2$NHCH$_3$, —(CH$_2$)$_2$SO$_2$NHCH$_3$, —(CH$_2$)$_3$SO$_2$NHCH$_3$, —CH$_2$SO$_2$N(CH$_3$)$_2$, —(CH$_2$)$_2$SO$_2$N(CH$_3$)$_2$, —CH$_2$SO$_2$NHCH$_2$CH$_3$, —(CH$_2$)$_2$SO$_2$NHCH$_2$CH$_3$, —(CH$_2$)$_3$SO$_2$NHCH$_2$CH$_3$, —CH$_2$SO$_2$N(CH$_2$CH$_3$)$_2$ or —(CH$_2$)$_2$SO$_2$N(CH$_2$CH$_3$)$_2$, —O—(CH$_2$)$_n$—SO$_2$NR$^{12}$R$^{13}$ such as —OCH$_2$SO$_2$NH$_2$, —O(CH$_2$)$_2$SO$_2$NH$_2$, —O(CH$_2$)$_3$SO$_2$NH$_2$, —CH$_2$SO$_2$NHCH$_3$, —O(CH$_2$)$_2$SO$_2$NHCH$_3$, —O(CH$_2$)$_3$SO$_2$NHCH$_3$, —CH$_2$SO$_2$N(CH$_3$)$_2$, —O(CH$_2$)$_2$SO$_2$N(CH$_3$)$_2$, —OCH$_2$SO$_2$NHCH$_2$CH$_3$, —O(CH$_2$)$_2$SO$_2$NHCH$_2$CH$_3$, —O(CH$_2$)$_3$SO$_2$NHCH$_2$CH$_3$, —OCH$_2$SO$_2$N(CH$_2$CH$_3$)$_2$, or —O(CH$_2$)$_2$SO$_2$N(CH$_2$CH$_3$)$_2$, —(CH$_2$)$_n$—CO-straight-chain or branched-chain alkyl group such as acetyl group, trifluoroacetyl group, propionyl group, butyloyl group, pentanoyl group, cyclopentanoyl group, —CH$_2$COCH$_3$, —(CH$_2$)$_2$COCH$_3$, —(CH$_2$)$_3$COCH$_3$, —(CH$_2$)$_4$COCH$_3$, —(CH$_2$)$_5$COCH$_3$, —CH$_2$COCH$_2$CH$_3$, —(CH$_2$)$_2$COCH$_2$CH$_3$, —(CH$_2$)$_3$COCH$_2$CH$_3$, —(CH$_2$)$_4$COCH$_2$CH$_3$, —(CH$_2$)$_5$COCH$_2$CH$_3$, —CH$_2$CO(CH$_2$)$_2$CH$_3$, —(CH$_2$)$_2$CO(CH$_2$)$_2$CH$_3$, —(CH$_2$)$_3$CO(CH$_2$)$_2$CH$_3$, —(CH$_2$)$_4$ CO(CH$_2$)$_2$CH$_3$ or —(CH$_2$)$_5$CO(CH$_2$)$_2$CH$_3$, —O—(CH$_2$)$_n$—CO-straight-chain or branched-chain alkyl group such as —OCOCH$_3$, —OCOCH$_2$CH$_3$, —OCH$_2$COCH$_3$, —O(CH$_2$)$_2$COCH$_3$, —O(CH$_2$)$_3$COCH$_3$, —O(CH$_2$)$_4$COCH$_3$, —O(CH$_2$)$_5$COCH$_3$, —OCH$_2$COCH$_2$CH$_3$, —O(CH$_2$)$_2$COCH$_2$CH$_3$, —O(CH$_2$)$_3$COCH$_2$CH$_3$, —O(CH$_2$)$_4$COCH$_2$CH$_3$, —O(CH$_2$)$_5$COCH$_2$CH$_3$, —OCH$_2$CO(CH$_2$)$_2$CH$_3$, —O(CH$_2$)$_2$CO(CH$_2$)$_2$ CH$_3$, —O(CH$_2$)$_3$CO(CH$_2$)$_2$CH$_3$, —O(CH$_2$)$_4$CO(CH$_2$)$_2$CH$_3$ or —O(CH$_2$)$_5$CO(CH$_2$)$_2$CH$_3$, —(CH$_2$)$_n$—CO-unsubstituted or substituted aryl group such as benzoyl group, methylbenzoyl group, methoxybenzoyl group, chlorobenzoyl group, —CH$_2$COPh, —(CH$_2$)$_2$COPh, —(CH$_2$)$_3$COPh, —(CH$_2$)$_4$COPh or —(CH$_2$)$_5$COPh, —O—(CH$_2$)$_n$—CO-unsubstituted or substituted aryl group such as —OCOPh, —OCH$_2$COPh, —O(CH$_2$)$_2$COPh, —O(CH$_2$)$_3$COPh, —O(CH$_2$)$_4$COPh or —O(CH$_2$)$_5$COPh, —(CH$_2$)$_n$-substituted or substituted amino group such as 2-aminoethyl group, 2-methylaminoethyl group, 2-ethylaminiethyl group, 2-propylaminoethyl group, 2-dimethylaminoethyl group, 2-diethylaminoethyl group, 2-diisopropylaminoethyl group, 2-(morpholin-1-yl)ethyl group, 2-(pyrrolidine-1-yl)ethyl group or 2-(1,4-diazabicyclo[2,2,2]-octan-1-yl)ethyl group, —O—(CH$_2$)$_{(n+1)}$ substituted or substituted amino group such as 2-aminoethoxy group, 2-methylaminoethoxy group, 2-ethylaminiethoxy group, 2-propylaminoethoxy group, 2-dimethylaminoethoxy group, 2-diethylaminoethoxy group, 2-diisopropylaminoethoxy group, 2-(morpholin-1-yl)ethoxy group, 2-(pyrrolidine-1-yl)ethoxy group or 2-(1,4-diazabicyclo[2,2,2]-octan-1-yl)ethoxy group, unsubstituted or substituted amino group such as amino group, methylamino group, dimethylamino group, ethylamino group, diethylamino group, propylamino group, dipropylamino group, isopropylamino group, diisopropylamino group, butylamino group, dibutylamino group, pentylamino group, dipentylamino group, acetylamino group, trifluoroacetylamino group, propionylamino group, butyloylamino group, pentanoylamino group, benzoylamino group, methanesulfonylamino group, ethanesulfonylamino group, benzenesulfonylamino group, toluenesulfonylamino group, trifluoromethanesulfonylamino group, trifluoroethanesulfonylamino group, benzenesulfonyl group, methoxycarbonylamino group, ethoxycarbonylamino group, propoxycarbonylamino group, isopropoxycarbonylamino group, cyclopropoxycarbonylamino group, butoxycarbonylamino group, isobutoxycarbonylamino group, t-butoxycarbonylamino group, cyclobutoxycarbonylamino group, pentyloxycarbonylamino group or cyclopentyloxycarbonylamino group.

R$^8$ and R$^9$ may be the same or different and are selected from hydroxyl group, straight-chain or branched-chain alkoxy group such as methoxy group, ethoxy group, propoxy group, isopropoxy group, cyclopropoxy group, butoxy group, isobutoxy group, cyclobutoxy group, pentyloxy group or cyclopentyloxy group, thiol group, straight-chain or branched-chain thioalkyl group such as thiomethyl group, thioethyl group, thiopropyl group, thiobutyl group or thiopentyl group, unsubstituted or substituted amino group such as amino group, methylamino group, dimethylamino group, ethylamino group, diethylamino group, propylamino group, dipropylamino group, isopropylamino group, diisopropylamino group, butylamino group, dibutylamino group, pentylamino group, dipentylamino group.

The compounds of the present invention include individual stereoisomers, enantimers, tautomers and mixture of these.

Furthermore, the compounds of the present invention include the prodrugs. In general, such prodrugs will be functional derivatives of the compounds which readily convertible in vivo desired the therapeutically active compounds and salts thereof. The groups forming prodrugs are described, for example, in Prog. Med., 5, 2157, 1985 and [IYAKUHIN-KAIHATU] BUNSISEKKEI., 7, 163, 1990 (HIROKA-WASHOTEN) and the groups are straight-chain or branched-chain alkyl group such as methyl group, ethyl group, propyl group, isopropyl group, butyl group, isobutyl group, pentyl group, cyclopentyl group, hexyl group or cyclohexyl group, straight-chain or branched chain alkanoyl group such as acetyl group, propionyl group or butyloyl group, straight chain or branched-chain alkoxycarbonyl group such as methoxycarbonyl group, ethoxycarbonyl group, propyloxycarbonyl group, butoxycarbonyl group, pentyloxycarbonyl group or cyclooxycarbonyl group, methoxymethyl group, methoxyethoxy group, (5-methyl-2-oxo-1,3-dioxol-4-yl)methyl group and methylpivaloate.

The pharmaceutically acceptable salts of compounds of the present invention retain their biological efficacy and property of parent compounds. The pharmaceutically acceptable salts of this invention are mentioned as follow. Bases for forming addition salts include lithium hydroxide, sodium hydroxide, potassium hydroxide, calcium hydroxide, magnesium hydroxide, ammonia, isopropylamine, diethylamine, triethylamine, ethanolamine, piperidine, pyridine, tris(hydroxymethyl)methylamine, tris(hydroxyethyl)methylamine, arginine, colline. Acids for forming additional salts are hydrochloric acid, hydrobromic acid, hydriodic acid, sulfuric acid, nitric acid, phosphoric acid, methanesulfonic acid, benzenesulfonic acid, formic acid, acetic acid, trifluoroacetic acid, oxalic acid, citric acid, malonic acid, fumaric acid, glutaric acid, adipic acid, maleic acid, tartaric acid, succinic acid, mandelic acid, malic acid, pantothenic acid, glutamic acid, aspartic acid. The reagents forming prodrugs pharmaceutically acceptable salts of compounds of the present invention are described, for example, in [Handbook of Pharmaceutical salts] P. Heinrich Stahl. (WILEY-VCH SHUPPAN)

The compounds represented by general formula (I) in the present invention are exemplified as follows.

(1) [5-(4-Ethylbenzyl)-2-hydroxyphenyl]phosphonic acid
(2) [2,4-Dimethoxy-5-(4-ethylbenzyl)phenyl] phosphonic acid
(3) [5-(4-Ethylbenzyl)-2-methoxyphenyl]phosphonic acid
(4) [5-(4-Ethylbenzyl)-2-hydroxybenzyl]phosphonic acid
(5) [3-(4-Ethylbenzyl)-4-hydroxybenzyl]phosphonic acid
(6) [3-(4-Ethylbenzyl)-4-(2-hydroxyethoxy)benzyl]phosphonic acid
(7) [5-(4-Ethylbenzyl)-2-fluorobenzyl]phosphonic acid
(8) [2-Chloro-5-(4-ethylbenzyl)benzyl]phosphonic acid
(9) [5-(4-Ethylbenzyl)-2-methylbenzylphosphonic acid
(10) [5-(4-Ethylbenzyl)-2-methoxybenzylphosphonic acid
(11) [2,4-Dimethoxy-5-(4-ethylbenzyl)benzyl] phosphonic acid
(12) [4-Chloro-3-(4-ethylbenzyl)benzyl]phosphonic acid
(13) [3-(4-Ethylbenzyl)-4-methoxybenzyl]phosphonic acid
(14) [3-(4-Ethylbenzyl)-4-ethoxybenzyl]phosphonic acid
(15) [3-(4-Ethylbenzyl)-4-n-propoxybenzyl]phosphonic acid
(16) [3-(4-Ethylbenzyl)-4-i-propoxybenzyl]phosphonic acid
(17) [3-Benzyloxy-5-(4-ethylbenzyl)benzyl]phosphonic acid
(18) [3-(2-Ethoxybenzyl)-4-hydroxybenzyl]phosphonic acid
(19) [3-(3-Ethoxybenzyl)-4-hydroxybenzyl]phosphonic acid
(20) [3-(4-Ethoxybenzyl)-4-hydroxybenzyl]phosphonic acid
(21) [3-(4-Ethoxybenzyl)-2-hydroxybenzyl]phosphonic acid
(22) [3-(4-Ethoxybenzyl)-4-(2-hydroxyethoxy)benzyl]phosphonic acid
(23) [3-(4-Ethoxybenzyl)-4-fluorobenzyl]phosphonic acid
(24) [4-Chloro-3-(4-ethoxybenzyl)benzyl]phosphonic acid
(25) [2,4-Dimethoxy-5-(4-ethoxybenzyl)benzyl]phosphonic acid
(26) [3-(4-Ethoxyphenoxy)-4-hydroxybenzyl]phosphonic acid
(27) [5-(4-Ethoxybenzyl)-2-hydroxybenzyl]phosphonic acid
(28) [3-(4-t-Butylbenzyl)-4-chlorobenzyl]phosphonic acid
(29) [5-(4-t-Butylbenzyl)-2-hydroxybenzyl]phosphonic acid
(30) [4-Chloro-3-(naphtalen-2-ylmethyl)benzyl]phosphonic acid
(31) [2-Hydroxy-5-(naphtalen-2-ylmethyl)benzyl]phosphonic acid
(32) [3-(Benzofuran-2-ylmethyl)-4-chlorobenzyl]phosphonic acid
(33) [3-(Benzo[b]thiophen-2-ylmethyl)-4-chlorobenzyl] phosphonic acid
(34) 2-[5-(4-Ethylbenzyl)-2-hydroxyphenyl]ethylphosphonic acid
(35) 2-[5-(4-Ethylbenzyl)-2-methoxyphenyl]ethylphosphonic acid
(36) {2-[3-(4-Ethylbenzyl)-4-hydroxyphenyl]-2-oxoethyl}phosphonic acid
(37) [3-(4-Ethylbenzyl)-4-hydroxybenzoyl]phosphonic acid
(38) [3-(4-Ethoxybenzyl)-4-hydroxybenzoyl]phosphonic acid
(39) [3-(4-Ethylphenoxy)-4-hydroxybenzoyl]phosphonic acid
(40) [3-[2-(4-Ethoxyphenyl)ethyl]-4-hydroxybenzoyl]phosphonic acid
(41) [3-(4-Ethoxyphenoxymethyl)-4-hydroxybenzoyl]phosphonic acid
(42) [4-Hydroxy-3-(4-methylthiobenzyl)benzoyl]phosphonic acid
(43) [4-Hydroxy-3-(4-hydroxybenzyl)benzoyl]phosphonic acid
(44) [4-Hydroxy-3-(4-methoxybenzyl)benzoyl]phosphonic acid
(45) [4-Hydroxy-3-(4-n-propoxybenzyl)benzoyl]phosphonic acid
(46) [4-Hydroxy-3-(4-i-propoxybenzyl)benzoyl]phosphonic acid
(47) [4-(2-Hydroxyethoxy)-3-(4-i-propoxybenzyl)benzoyl] phosphonic acid
(48) [3-(4-n-Butoxybenzyl)-4-hydroxybenzyl]phosphonic acid
(49) [4-Hydroxy-3-(4-phenoxybenzyl)benzoyl]phosphonic acid
(50) [4-(2-Hydroxyethoxy)-3-(4-phenoxybenzyl)benzoyl] phosphonic acid
(51) [4-Hydroxy-3-(4-n-octyloxybenzyl)benzoyl]phosphonic acid
(52) [3-(4-n-Hexyloxybenzyl)-4-hydroxy]benzoyl]phosphonic acid
(53) [4-Hydroxy-3-[4-(2-hydroxyethoxy)benzyl]benzoyl] phosphonic acid
(54) [3-(Benzo[b]thiophen-2-ylmethyl)-4-hydroxybenzoyl] phosphonic acid
(55) [3-(Benzo[b]thiophen-2-ylmethyl)-4-(2-hydroxyethoxy)benzoyl]phosphonic acid
(56) [3-(Benzo[1,3]dioxol-5-ylmethyl)-4-hydroxybenzoyl] phosphonic acid
(57) [3-(4-Ethoxybenzyl)-4-(2-hydroxyethoxy)benzoyl] phosphonic acid
(58) [3-[4-(2-Ethoxyethoxy)benzyl]-4-hydroxybenzoyl] phosphonic acid
(59) [4-Hydroxy-3-(4-methylsulfonylbenzyl)benzoyl]phosphonic acid
(60) [4-(2-Hydroxyethoxy)-3-(4-methylthiobenzyl)benzoyl] phosphonic acid
(61) [3-(4-Ethylthiobenzyl)-4-hydroxybenzoyl]phosphonic acid
(62) [4-(2-Hydroxyethoxy)-3-(4-ethylthiobenzyl)benzoyl] phosphonic acid
(63) [3-(4-Ethylsulfonylbenzyl)-4-hydroxybenzoyl]phosphonic acid

(64) 5-(4-Ethoxybenzyl)-2-thiophenephosphonic acid
(65) [5-(4-Ethoxybenzyl)thiophen-2-ylmethyl]phosphonic acid
(66) [5-(Benzofuran-2-ylmethyl)-2-thiophenephosphonic acid
(67) [5-(Benzofuran-2-ylmethyl)thiophen-2-ylmethyl]phosphonic acid
(68) [5-(Benzo[b]thiophen-2-ylmethyl)-2-thiophenephosphonic acid
(69) [5-(Benzo[b]thiophen-2-ylmethyl)thiophen-2-ylmethyl]phosphonic acid
(70) [5-(4-Ethoxybenzyl)thiophen-2-carbonyl]phosphonic acid
(71) [5-(4-Ethoxybenzyl)-3-methylthiophen-2-carbonyl]phosphonic acid
(72) [5-(4-Ethoxybenzyl)thiophen-3-carbonyl]phosphonic acid
(73) [5-(4-Methylthiobenzyl)thiophen-2-carbonyl]phosphonic acid
(74) [5-(4-Methylsulfonylbenzyl)thiophen-2-carbonyl]phosphonic acid
(75) [5-(4-Chlorobenzyl)thiophen-2-carbonyl]phosphonic acid
(76) [5-(4-Ethylthiobenzyl)thiophen-2-carbonyl]phosphonic acid
(77) [5-(4-Phenoxybenzyl)thiophen-2-carbonyl]phosphonic acid
(78) [5-(4-Benzyloxybenzyl)thiophen-2-carbonyl]phosphonic acid
(79) [5-(4-i-Propoxybenzyl)thiophen-2-carbonyl]phosphonic acid
(80) [5-(4-n-Butoxybenzyl)thiophen-2-carbonyl]phosphonic acid
(81) [5-(4-n-Pentyloxybenzyl)thiophen-2-carbonyl]phosphonic acid
(82) [5-(4-n-Octyloxybenzyl)thiophen-2-carbonyl]phosphonic acid
(83) [5-(4-n-Tridecanyloxybenzyl)thiophen-2-carbonyl]phosphonic acid
(84) [5-[4-(Ethoxyethoxy)benzyl]thiophen-2-carbonyl]phosphonic acid
(85) [5-(4-Phosphonocarbonylthiophen-2-ylmethyl)phenoxy]phosphonic acid
(86) [5-(4-Carbamoylmethoxybenzyl)thiophen-2-carbonyl]phosphonic acid
(87) [5-[4-(2-Morpholin-4-ylethoxy)benzyl]thiophen-2-carbonyl]phosphonic acid
(88) [5-(Benzothiophen-2-ylmethyl)thiophen-2-carbonyl]phosphonic acid
(89) 5-(4-Ethylbenzyl)benzothiophen-2-ylphosphonic acid
(90) [5-(4-Ethylbenzyl)benzothiophen-2-ylmethyl]phosphonic acid
(91) [4-(4-Methylthiobenzyl)thiazol-2-carbonyl]phosphonic acid
(92) [3-(5-Ethylthiophen-2-ylmethyl)-4-hydroxybenzoyl]phosphonic acid
(93) [4-(2-Methoxyethoxy)-3-(4-phenoxybenzyl)benzoyl]phosphonic acid
(94) [2-(4-Phenoxybenzyl)-4-phosphonocarbonylphenoxy]acetic acid methylester
(95) [2-(4-Phenoxybenzyl)-4-phosphonocarbonylphenoxy]acetic acid
(96) [4-Carbamoylmethoxy-3-(4-phenoxybenzyl)benzoyl]phosphonic acid
(97) [4-(2-Aminoethoxy)-3-(4-phenoxybenzyl)benzoyl]phosphonic acid
(98) [4-(4-Ethoxybenzyl)-3-(4-hydroxybutoxy)benzoyl]phosphonic acid
(99) [3-(4-Ethoxybenzyl)-4-(6-hydroxyhexyloxy)benzoyl]phosphonic acid
(100) [5-(4-Ethylbenzyl)-2-hydroxyphenyl]thiophosphonic acid
(101) [4-Hydroxy-3-[4-(3-phenyl)phenoxybenzyl]benzoyl]phosphonic acid
(102) [4-Hydroxy-3-[4-(4-phenyl)phenoxybenzyl]benzoyl]phosphonic acid
(103) [4-(2-Methoxyethoxy)-3-[4-(3-phenyl)phenoxybenzyl]benzoyl]phosphonic acid
(104) [4-(2-Hydroxyethoxy)-3-[4-(3-phenyl)phenoxybenzyl]benzoyl]phosphonic acid
(105) [4-Carbamoylmethoxy-3-[4-(3-phenyl)phenoxybenzyl]benzoyl]phosphonic acid
(106) [4-(2-Hydroxyethoxy)-3-(4-n-octyloxybenzyl)benzoyl]phosphonic acid
(107) [4-[(2-Hydroxyethylcarbamoyl)methoxy]-3-(4-n-octyloxybenzyl)benzoyl]phosphonic acid
(108) [4-Carbamoylmethoxy-3-(4-n-octyloxybenzyl)benzoyl]phosphonic acid
(109) [4-[(1-Carbamoyl-1-methylethylcarbamoyl)methoxy]-3-(4-n-octyloxybenzyl)benzoyl]phosphonic acid
(110) [4-(2-Aminoethoxy)-3-(4-n-octyloxybenzyl)benzoyl]phosphonic acid
(111) [4-(Methoxyethoxy)-3-(4-n-octyloxybenzyl)benzoyl]phosphonic acid
(112) [4-Hydroxy-3-[4-[5-(2-hydroxy-1,1-bishydroxymethylethylcarbamoyl)pentyloxy]benzyl]bensoyl]phosphonic acid
(113) [4-Hydroxy-3-[4-(6-oxo-morpholin-1-ylhexyloxy)benzyl]benzoyl]phosphonic acid
(114) [4-Hydroxy-3-[4-[5-(2-hydroxyethylcarbamoyl)pentyloxy]benzyl]benzoyl]phosphonic acid
(115) [4-(2-Acetylaminoethoxy)-3-(4-n-octyloxybenzyl)benzoyl]phosphonic acid
(116) [4-(2-Methanesulfonylaminoethoxy)-3-(4-n-octyloxybenzyl)benzoyl]phosphonic acid
(117) [3-(4-n-Octyloxybenzyl)-4-(2-ureidoethoxy)benzoyl]phosphonic acid
(118) [4-Hydroxy-3-(3'-(5-hydroxypentyloxy)biphenyl-3-yloxy)benzyl]benzoyl]phosphonic acid
(119) [4-Hydroxy-3-[4-(6-oxo-piperadin-1-ylhexyloxy)benzyl]benzoyl]phosphonic acid
(120) [4-Hydroxy-6-methyl-3-(4-n-octyloxybenzyl)benzoyl]phosphonic acid
(121) [5-[4-(3-Phenyl)phenoxybenzyl]thiophene-2-carbonyl]phosphonic acid
(122) [5-[4-(4-Phenyl)phenoxybenzyl]thiophene-2-carbonyl]phosphonic acid The above mentioned compounds numbered from 1 to 122 will be referred to herein after, as compound 1 - - - compound 122, respectively.

The compounds of the invention can be synthesized according to the following procedures. During any of the processes for synthesis of the compounds of the present invention, it may be necessary and/or desirable to protect sensitive or reactive groups on any of the molecules concerned. This may be achived by means of conventional protecting groups, such as those described in (Protective Groups in Organic Synthesis] WILEY-Interscience, Greene Wuts and are selected from a benzyl group, 4-methoxybenzyl group, allyl group, methyl group, methoxymethyl group, methoxyethoxy group, benzyloxybenzyl group, methoxythiomethyl group, trimethylsilyl group, triisopropylsilyl group, t-butyldimethylsilyl group, t-butyldiphenylsilyl group, tetrahydropyranyl group, acetyl group, pivaloyl group, benzoyl group, t-butoxycarbonyl group, allyloxycarbonyl group and benzyloxycarbonyl group.

Scheme 1 shows the preparation of compounds represented by general formula (I) wherein E is an oxygen atom and A is a bond.

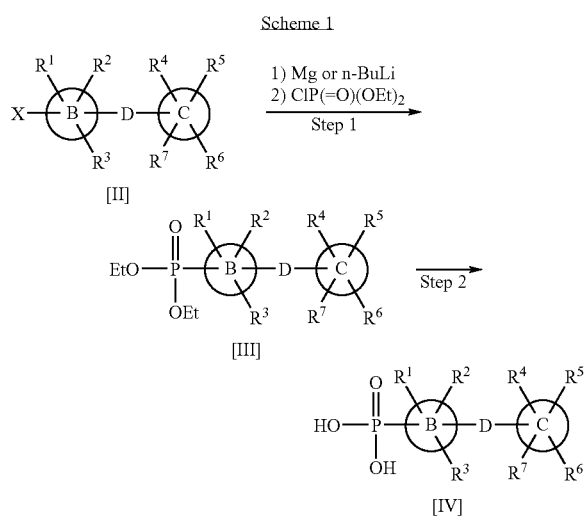

Scheme 1: wherein: X is halogen atom; B, C, D and $R^1 \sim R^7$ as defined above.

Step 1: Compound (III) can be obtained by the reaction of a Grignard reagent or organolithium reagent generated from compound (II) with diethyl chlorophosphonate. In general, the reaction is carried out in an inert solvent. Preferred reaction solvents for use in this reaction include ether and tetrahydrofuran (THF). In general, the reaction is carried out under in the range from −78° C. up to 25° C.

Step 2: Compound (IV) can be obtained by the hydrolysis or transesterification of compound (III). In hydrolysis under acidic conditions, hydrochloric acid, sulfuric acid and trifluoroacetic acid are used. On the other hand, lithium hydroxide, sodium hydroxide, potassium hydroxide, calcium hydroxide and barium hydroxide are used in hydrolysis under basic conditions. In general, the reaction is carried out in an inert solvent. Preferred reaction solvents for use in this reaction include water, methanol, ethanol, THF and 1,4-dioxane. In general, the reaction is carried out in the range of from 0° C. up to the reflux temperature of the reaction mixture. Alternatively, compound (IV) can be obtained by transestrification of compound (III). Chlorotrimethylsilane-sodium iodide, bromotrimethylsilane and iodotrimethylsilane can be used in this reaction. In general, the reaction is carried out in an inert solvent. Preferred reaction solvents for use in this reaction are aprotic solvents such as acetonitrile, THF, dichloromethane, chloroform, benzene and toluene. Furthermore, the reaction can be carried out in the presence of bases such as pyridine, lutidine and collidine. In general, the reaction is carried out in the range of −20° C. up to the reflux temperature of the reaction mixture.

Scheme 2 shows the preparation of compounds represented by general formula (I) wherein E is an oxygen atom and A is —CH$_2$—.

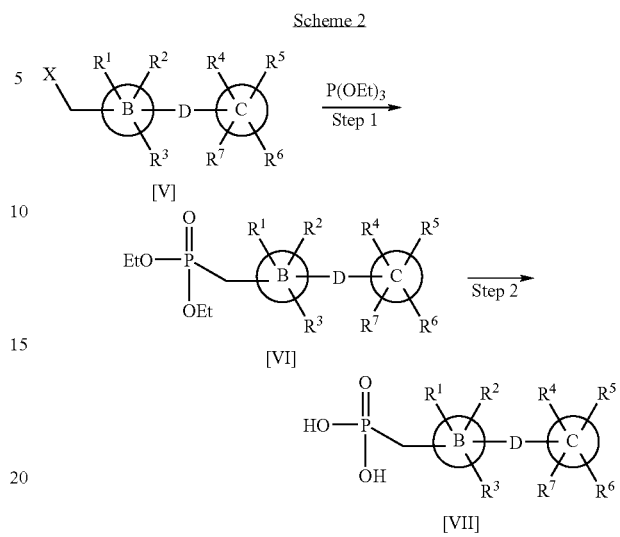

Scheme 2: wherein: X is halogen atom, methanesulfonyl group, toluenesulfonyl group or trifluoromethanesulfonyl group; B, C, D and $R^1 \sim R^7$ as defined above.

Step 1: Compound (VI) is obtained by the reaction of compound (V) with triethyl phosphite. The reaction is carried out in the absence of a solvent or in an inert solvent such as benzene, toluene or xylene. The best result of reaction gave was in the absence of reaction solvents. In general, the reaction is carried out in the range of from 70° C. up to 200° C.

Step 2: Compound (VII) can be obtained by the hydrolysis or transesterification of compound (VI). In hydrolysis under acidic conditions, hydrochloric acid, sulfuric acid and trifluoroacetic acid are used. On the other hand, lithium hydroxide, sodium hydroxide, potassium hydroxide, calcium hydroxide and barium hydroxide are used in hydrolysis under basic conditions. In general, the reaction is carried out in an inert solvent. Preferred reaction solvents for use in this reaction include water, methanol, ethanol, THF and 1,4-dioxane. In general, the reaction is carried out in the range of from 0° C. up to the reflux temperature of the reaction mixture. Alternatively, compound (VII) can be obtained by the transestrification of compound (VI). Chlorotrimethylsilane-sodium iodide, bromotrimethylsilane and iodotrimethylsilane can be used in this reaction. In general, the reaction is carried out in an inert solvent. Preferred reaction solvents for use in this reaction are aprotic solvents such as acetonitrile, THF, dichloromethane, chloroform, benzene and toluene. Furthermore, the reaction can be carried out in the presence of bases such as pyridine, lutidine and collidine. In general, the reaction is carried out under in the range of from −20° C. up to the reflux temperature of the reaction mixture.

Scheme 3 shows the preparation of compounds represented by general formula (I) wherein E is an oxygen atom and A is —CH$_2$CH$_2$—

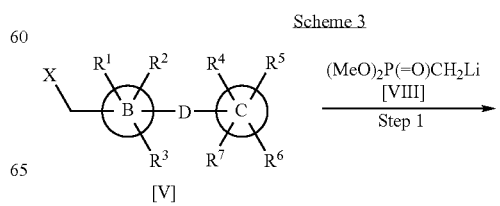

-continued

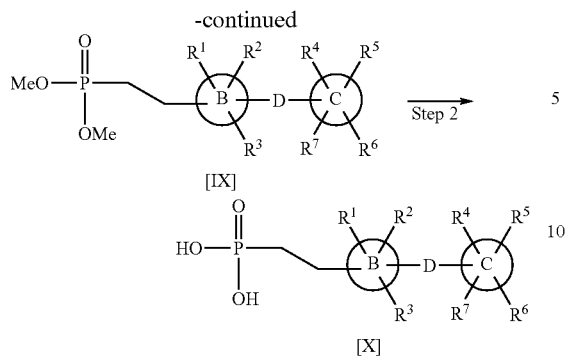

[IX]

[X]

Scheme 3: wherein: X is halogen atom, methanesulfonyl group, toluenesulfonyl group or trifluoromethanesulfonyl group; B, C, D and R¹~R⁷ as defined above.

Step 1: Compound (IX) can be obtained by reaction of compound (V) with organolithium reagent (VIII) generated from dimethyl methylphosphonate. In general, the reaction is carried out in an inert solvent. Preferred reaction solvents for use in this reaction include ether and THF. In general, the reaction is carried out in the range of from −78° C. up to 25° C.

Step 2: Compound (X) can be obtained by the hydrolysis or transesterification of compound (IX). In hydrolysis under acidic conditions, hydrochloric acid, sulfuric acid and trifluoroacetic acid are used. On the other hand, lithium hydroxide, sodium hydroxide, potassium hydroxide, calcium hydroxide and barium hydroxide are used in hydrolysis under basic conditions. In general, the reaction is carried out in an inert solvent. Preferred reaction solvents for use in this reaction include water, methanol, ethanol, THF and 1,4-dioxane. In general, the reaction is carried out in the range of from 0° C. up to the reflux temperature of the reaction mixture. Alternatively, compound (X) can be obtained by transestrification of compound (IX). Chlorotrimethylsilane-sodium iodide, bromotrimethylsilane and iodotrimethylsilane can be used in this reaction. In general, the reaction is carried out in an inert solvent. Preferred reaction solvents for use in this reaction are aprotic solvents such as acetonitrile, THF, dichloromethane, chloroform, benzene and toluene. Furthermore, the reaction can be carried out in the presence of bases such as pyridine, lutidine and collidine. In general, the reaction is carried out in the range of from −20° C. up to the reflux temperature of the reaction mixture.

Scheme 4 shows the preparation of compounds represented by general formula (I) wherein E is an oxygen atom and A is —CO—.

Scheme 4

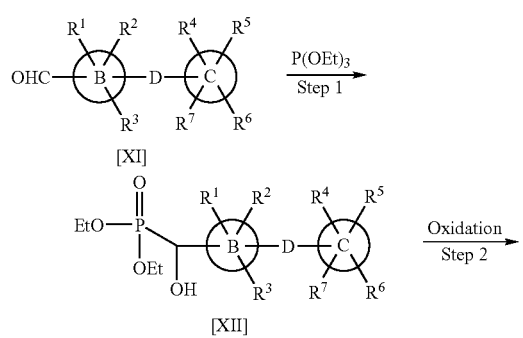

-continued

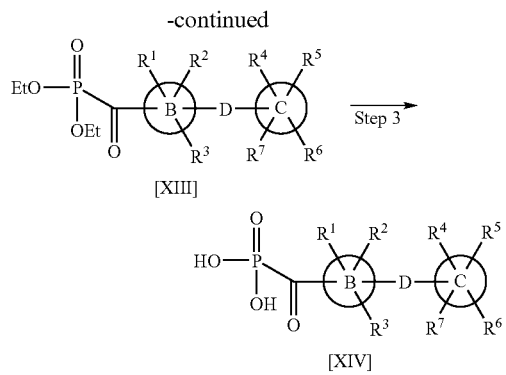

[XIII]

[XIV]

Scheme 4: wherein: each symbols as defined above.

Step 1: Compound (XII) can be obtained by the reaction of compound (XI) with diethyl phosphite. In general, the reaction is carried out in an inert solvent in the presence of bases. Sodium methoxide, sodium ethoxide, sodium hydride potassium hydride and triethylamine are suitable for bases. Preferred reaction solvents for use in this reaction include ether, THF, dichloromethane, benzene and toluene. In general, the reaction is carried out in the range of from −78° C. up to the reflux temperature of the reaction mixture.

Step 2: Compound (XIII) can be obtained by the oxidation of compound (XII). Pyridinium chlorochlomate, pyridinium dichromate or manganese dioxide, as oxidants, and oxalyl chloride-dimethylsulfoxide-triethylamine, sulfur-trioxide-pyridine complex-dimethylsulfoxide-triethylamine systems are used for this reaction. In general, the reaction is carried out in an inert solvent. Preferred reaction solvents for use in this reaction include dichloromethane, chloroform, benzene, toluene and acetone. In general, the reaction is carried out in the range of from −78° C. up to the reflux temperature of the reaction mixture.

Step 3: Compound (XIV) can be obtained by the hydrolysis or transesterification of compound (XIII). In hydrolysis under acidic conditions, hydrochloric acid, sulfuric acid and trifluoroacetic acid are used. On the other hand, lithium hydroxide, sodium hydroxide, potassium hydroxide, calcium hydroxide and barium hydroxide are used in hydrolysis-under basic conditions. In general, the reaction is carried out in an inert solvent. Preferred reaction solvents for use in this reaction include water, methanol, ethanol, THF and 1,4-dioxane. In general, the reaction is carried out in the range of from 0° C. up to the reflux temperature of the reaction mixture. Alternatively, compound (XIV) can be obtained by the transesterification of compound (XIII). Chlorotrimethylsilane-sodium iodide, bromotrimethylsilane and iodotrimethylsilane can be used in this reaction. In general, the reaction is carried out in an inert solvent. Preferred reaction solvents for use in this reaction are aprotic solvents such as acetonitrile, THF, dichloromethane, chloroform, benzene and toluene. Furthermore, the reaction can be carried out in the presence of bases such as pyridine, lutidine and collidine. In general, the reaction is carried out in the range of from −20° C. up to the reflux temperature of the reaction mixture.

Alternatively, compound (XIV) is synthesized by according to Scheme 5.

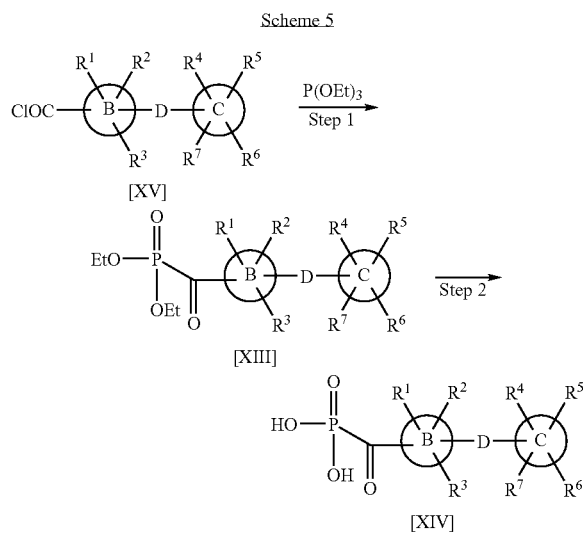

Scheme 5: wherein: each symbols as defined above.

Step 1: Compound (XIII) is obtained by the reaction of compound (XV) with triethyl phosphite. The reaction is carried out in the absence of a solvent or in an inert solvent such as benzene, toluene or xylene. The best reaction results were in the absence of a reaction solvent. In general, the reaction is carried out in the range of from 70° C. to 200° C.

Step 2: Compound (XIV) can be obtained by the hydrolysis or transesterification of compound (XIII). In hydrolysis under acidic conditions, hydrochloric acid, sulfuric acid and trifluoroacetic acid are used. On the other hand, lithium hydroxide, sodium hydroxide, potassium hydroxide, calcium hydroxide and barium hydroxide are used in hydrolysis under basic conditions. In general, the reaction is carried out in an inert solvent. Preferred reaction solvents for use in this reaction include water, methanol, ethanol, THF and 1,4-dioxane. In general, the reaction is carried out in the range from 0° C. up to the reflux temperature of the reaction mixture. Alternatively, compound (XIV) can be obtained by transesterification of compound (XIII). Chlorotrimethylsilane-sodium iodide, bromotrimethylsilane and iodotrimethylsilane can be used in this reaction. In general, the reaction is carried out in an inert solvent. Preferred reaction solvents for use in this reaction are aprotic solvents such as acetonitrile, THF, dichloromethane, chloroform, benzene and toluene. Furthermore, the reaction can be carried out in the presence of bases such as pyridine, lutidine and collidine. In general, the reaction is carried out in the range of from −20° C. up to the reflux temperature of the reaction mixture.

Scheme 6 shows the preparation of compounds represented by general formula (I) wherein E is an oxygen atom and A is —CH$_2$C(C═O)—.

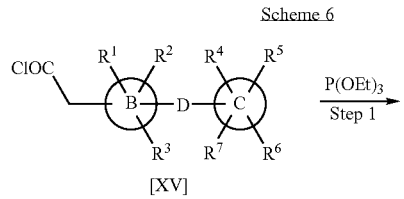

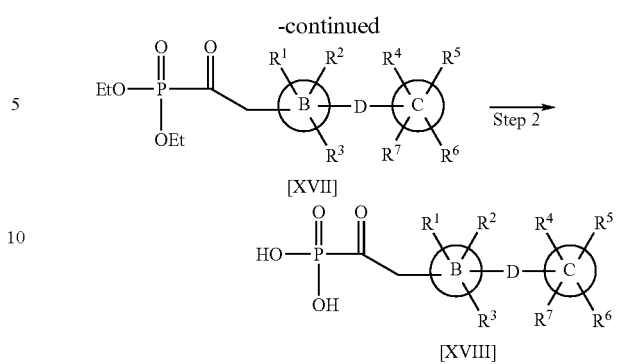

Scheme 6: wherein: each symbols as defined above.

Step 1: Compound (XVII) is obtained by the reaction of compound (XVI) with triethyl phosphite. The reaction was carried out in the absence of a solvent or in an inert solvent such as benzene, toluene or xylene. The best reaction result was in the absence of a reaction solvent. In general, the reaction is carried out in the range of from 70° C. up to 200° C.

Step 2: Compound (XVIII) can be obtained by hydrolysis or transesterification of compound (XVII). In hydrolysis under acidic conditions, hydrochloric acid, sulfuric acid and trifluoroacetic acid are used. On the other hand, lithium hydroxide, sodium hydroxide, potassium hydroxide, calcium hydroxide and barium hydroxide are used in hydrolysis under basic conditions. In general, the reaction is carried out in an inert solvent. Preferred reaction solvents for use in this reaction include water, methanol, ethanol, THF and 1,4-dioxane. In general, the reaction is carried out in the range of from 0° C. to the reflux temperature of the reaction mixture. Alternatively, compound (XVIII) can be obtained by the transesterification of compound (XVII). Chlorotrimethylsilane-sodium iodide, bromotrimethylsilane and iodotrimethylsilane can be used in this reaction. In general, the reaction is carried out in an inert solvent. Preferred reaction solvents for use in this reaction are aprotic solvents such as acetonitrile, THF, dichloromethane, chloroform, benzene and toluene. Furthermore, the reaction can be carried out in the presence of bases such as pyridine, lutidine and collidine. In general, the reaction is carried out in the range of from −20° C. to the reflux temperature of the reaction mixture.

Scheme 7 shows the preparation of compounds represented by general formula (I) wherein E is an oxygen atom and A is —C(═O)—CH$_2$—

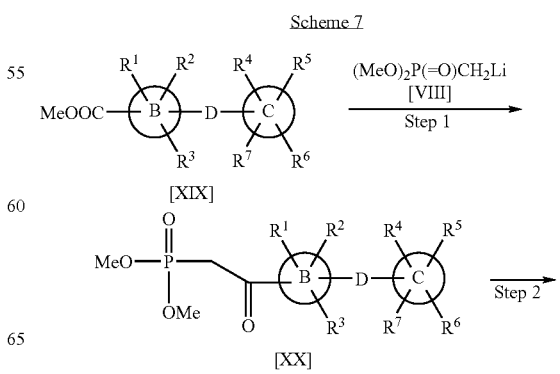

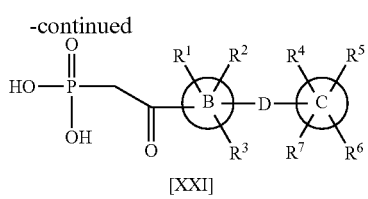

Scheme 7: wherein: each symbols as defined above.

Step 1: Compound (XX) can be obtained by reaction of compound (XIX) with organolithium reagent (VIII) generated from dimethyl methylphosphonate. In general, the reaction is carried out in an inert solvent. Preferred reaction solvents for use in this reaction include ether and THF. In general, the reaction is carried out in the range of from −78° C. up to 25° C.

Step 2: Compound (XXI) can be obtained by the hydrolysis or transesterification of compound (XX). In hydrolysis under acidic conditions, hydrochloric acid, sulfuric acid and trifluoroacetic acid are used. On the other hand, lithium hydroxide, sodium hydroxide, potassium hydroxide, calcium hydroxide and barium hydroxide are used in hydrolysis under basic conditions. In general, the reaction is carried out in an inert solvent. Preferred reaction solvents for use in this reaction include water, methanol, ethanol, THF and 1,4-dioxane. In general, the reaction is carried out in the range of from 0° C. up to the reflux temperature of the reaction mixture. Alternatively, compound (XXI) can be obtained by the transesterification of compound (XX). Chlorotrimethylsilane-sodium iodide, bromotrimethylsilane and iodotrimethylsilane can be used in this reaction. In general, the reaction is carried out in an inert solvent. Preferred reaction solvents for use in this reaction are aprotic solvents such as acetonitrile, THF, dichloromethane, chloroform, benzene and toluene. Furthermore, the reaction can be carried out in the presence of bases such as pyridine, lutidine and collidine. In general, the reaction is carried out in the range of from −20° C. up to the reflux temperature of the reaction mixture.

Scheme 8 shows preparation of compounds represented by general formula (I) wherein E is an oxygen atom.

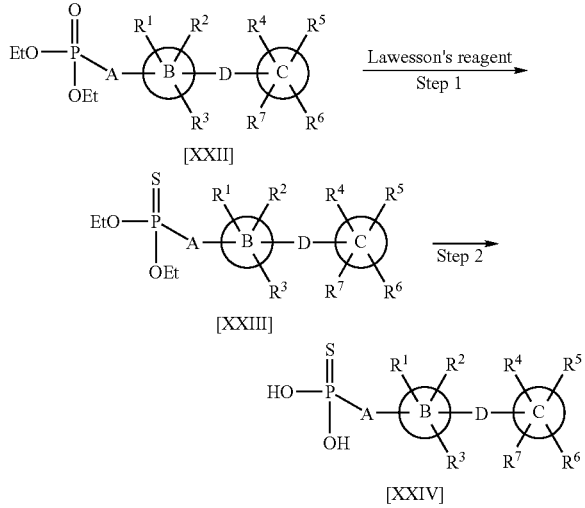

Scheme 8: wherein: each symbols as defined above.

Step 1: Compound (XXIII) can be obtained by the reaction of compound (XXII) with Lawesson's reagent. In general, the reaction is carried out in an inert solvent. Preferred reaction solvents for use in this reaction include benzene, toluene and N,N-dimethylformamide (DMF). In general, the reaction is carried out in the range of from 0° C. up to the reflux temperature of the reaction mixture.

Step 2: Compound (XXIV) can be obtained by the hydrolysis or transesterification of compound (XXIII). In hydrolysis under acidic conditions, hydrochloric acid, sulfuric acid and trifluoroacetic acid are used. On the other hand, lithium hydroxide, sodium hydroxide, potassium hydroxide, calcium hydroxide and barium hydroxide are used in hydrolysis under basic conditions. In general, the reaction is carried out in an inert solvent. Preferred reaction solvents for use in this reaction include water, methanol, ethanol, THF and 1,4-dioxane. In general, the reaction is carried out in the range of from 0° C. up to the reflux temperature of the reaction mixture. Alternatively, compound (XXIV) can be obtained by the transesterification of compound (XXIII). Chlorotrimethylsilane-sodium iodide, bromotrimethylsilane and iodotrimethylsilane can be used in this reaction. In general, the reaction is carried out in an inert solvent. Preferred reaction solvents for use in this reaction are aprotic solvents such as acetonitrile, THF, dichloromethane, chloroform, benzene and toluene. Furthermore, the reaction can be carried out in the presence of bases such as pyridine, lutidine and collidine. In general, the reaction is carried out in the range of from −20° C. up to the reflux temperature of the reaction mixture.

Scheme 9 shows preparation of compounds represented by general formula (I) wherein D is —$(CH_2)_{(n+1)}$—.

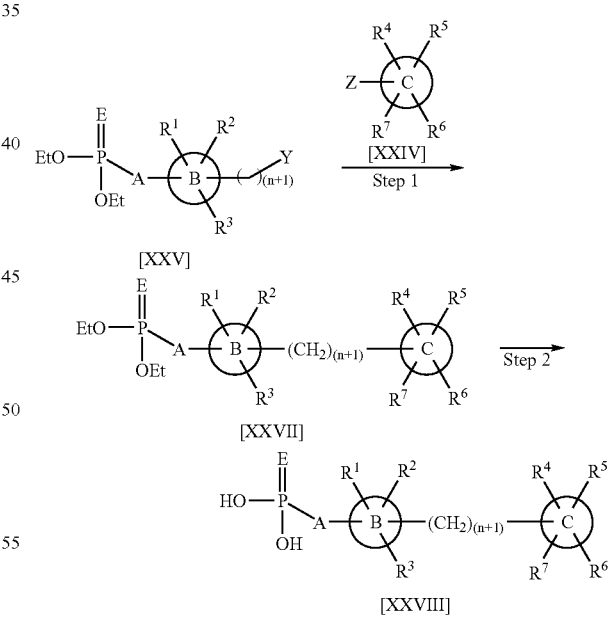

Scheme 9: wherein: Y is halogen atom or trifluoromethanesulfonyl group. Z is $B(OH)_2$ or $Sn(n-Bu)_3$. $R^1$~$R^7$, A, B, C, E and n as defined above.

Step 1: Compound (XXVII) can be obtained by the reaction of compound (XXV) with compound (XXVII). In the case of Y being $B(OH)_2$ in the formula (XXVI), the reaction is carried out using a palladium catalyst.

Tetrakis(triphenylphosphine)palladium (0), bis(triphenylphosphine)palladium chloride (2) and palladium acetate can be used as catalysts. This reaction is carried out in the presence of a base such as sodium hydrogencarbonate, sodium carbonate, sodium hydroxide, sodium methoxide, potassium fluoride, cesium fluoride triethylamine and pyridine. In general, the reaction is carried out in an inert solvent. Preferred reaction solvents for use in this reaction include benzene, toluene, dioxane, THF, chloroform, methanol, DMF, acetonitrile and water. In general, the reaction is carried out under the reflux temperature of the reaction mixture.

Step 2: Compound (XXVIII) can be obtained by the hydrolysis or transesterification of compound (XXVII). In hydrolysis under acidic conditions, hydrochloric acid, sulfuric acid and trifluoroacetic acid are used. On the other hand, lithium hydroxide, sodium hydroxide, potassium hydroxide, calcium hydroxide and barium hydroxide are used in hydrolysis under basic conditions. In general, the reaction is carried out in an inert solvent. Preferred reaction solvents for use in this reaction include water, methanol, ethanol, THF and 1,4-dioxane. In general, the reaction is carried out in the range of from 0° C. up to the reflux temperature of the reaction mixture. Alternatively, compound (XXVIII) can be obtained by the transesterification of compound (XXVII). Chlorotrimethylsilane-sodium iodide, bromotrimethylsilane and iodotrimethylsilane can be used in this reaction. In general, the reaction is carried out in an inert solvent. Preferred reaction solvents for use in this reaction are aprotic solvents such as acetonitrile, THF, dichloromethane, chloroform, benzene and toluene. Furthermore, the reaction can be carried out in the presence of bases such as pyridine, lutidine and collidine. In general, the reaction is carried out in the range of from −20° C. up to the reflux temperature of the reaction mixture.

Scheme 10 shows preparation of compounds represented by general formula (I) wherein D is —$(CH_2)_n$—O—$(CH_2)_m$—.

potassium hydride, sodium hydroxide, potassium hydroxide, sodium carbonate, potassium carbonate, triethylamine and pyridine. In general, the reaction is carried out in an inert solvent. Preferred reaction solvents for use in this reaction include benzene, toluene, dioxane, THF, chloroform, DMF and dimethylsulfoxide (DMSO) and acetonitrile. In general, the reaction is carried out in the range of from room temperature up to the reflux temperature of the reaction mixture.

Step 2: Compound (XXXII) can be obtained by the hydrolysis or transesterification of compound (XXXI). In hydrolysis under acidic conditions, hydrochloric acid, sulfuric acid and trifluoroacetic acid are used. On the other hand, lithium hydroxide, sodium hydroxide, potassium hydroxide, calcium hydroxide and barium hydroxide are used in hydrolysis under basic conditions. In general, the reaction is carried out in an inert solvent. Preferred reaction solvents for use in this reaction include water, methanol, ethanol, THF and 1,4-dioxane. In general, the reaction is carried out in the range of from 0° C. up to the reflux temperature of the reaction mixture. Alternatively, compound (XXXII) can be obtained by the transesterification of compound (XXXI). Chlorotrimethylsilane-sodium iodide, bromotrimethylsilane and iodotrimethylsilane can be used in this reaction. In general, the reaction is carried out in an inert solvent. Preferred reaction solvents for use in this reaction are aprotic solvents such as acetonitrile, THF, dichloromethane, chloroform, benzene and toluene. Furthermore, the reaction can be carried out in the presence of bases such as pyridine, lutidine and collidine. In general, the reaction is carried out in the range of from −20° C. up to the reflux temperature of the reaction mixture.

Scheme 11 shows the preparation of compounds represented by general formula (I) wherein D is —$(CH_2)_n$—NH—$(CH_2)_m$—.

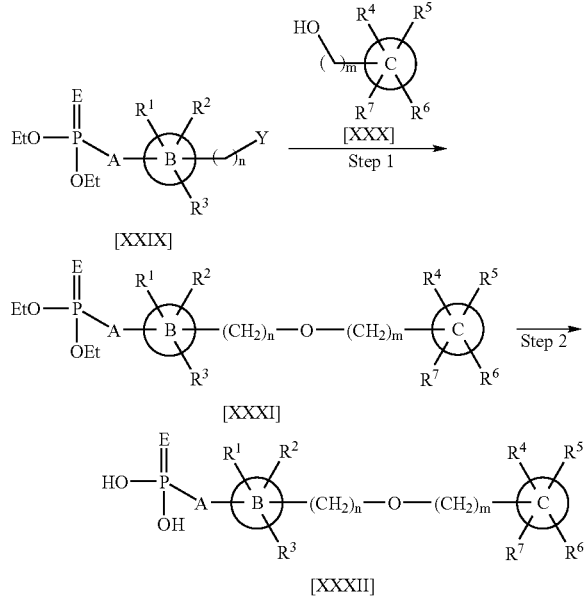

Scheme 10: wherein: Y is halogen atom, methanesulfonyl group, p-toluenesulfonyl group or trifluoromethanesulfonyl group. $R^1$~$R^7$, A, B, C, E, m and n as defined above.

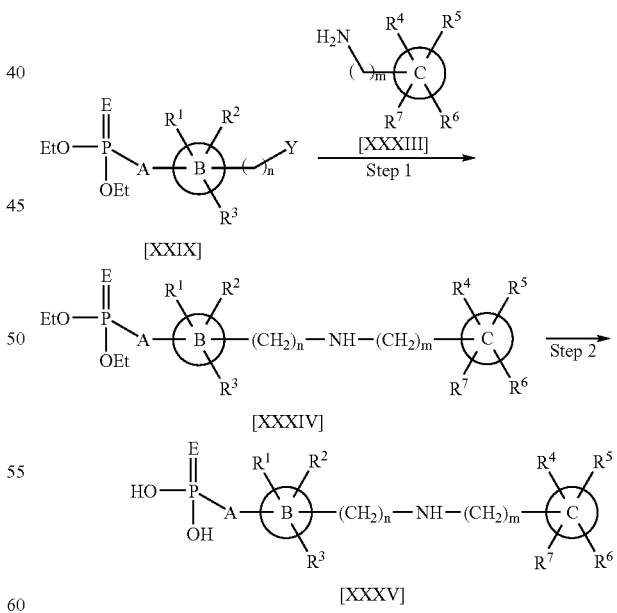

Scheme 11: wherein: Y is halogen atom, methanesulfonyl group, p-toluenesulfonyl group or trifluoromethanesulfonyl group. $R^1$~$R^7$, A, B, C, E, m and n as defined above.

Step 1: Compound (XXXI) can be obtained by the reaction of compound (XXIX) with compound (XXX). The reaction is carried out in the presence of bases such as sodium hydride, Step 1: Compound (XXXIV) can be obtained by the reaction of compound (XXIX) with compound (XXXIII). The reaction is carried out in the presence of bases such as sodium hydride, potassium hydride, sodium hydroxide, potassium hydroxide, sodium carbonate, potassium carbonate, triethylamine and pyridine. In general, the reaction is carried out in an inert solvent. Preferred reaction solvents for use in this reaction include benzene, toluene, dioxane, THF, chloroform, DMF and DMSO and acetonitrile. In general, the reaction is carried out in the range of from room temperature up to the reflux temperature of the reaction mixture.

Step 2: Compound (XXXV) can be obtained by the hydrolysis or transesterification of compound (XXXIV). In hydrolysis under acidic conditions, hydrochloric acid, sulfuric acid and trifluoroacetic acid are used. On the other hand, lithium hydroxide, sodium hydroxide, potassium hydroxide, calcium hydroxide and barium hydroxide are used in hydrolysis under basic conditions. In general, the reaction is carried out in an inert solvent. Preferred reaction solvents for use in this reaction include water, methanol, ethanol, THF and 1,4-dioxane. In general, the reaction is carried out in the range of from 0° C. up to the reflux temperature of the reaction mixture. Alternatively, compound (XXXV) can be obtained by the transesterification of compound (XXXIV). Chlorotrimethylsilane-sodium iodide, bromotrimethylsilane and iodotrimethylsilane can be used in this reaction. In general, the reaction is carried out in an inert solvent. Preferred reaction solvents for use in this reaction are aprotic solvents such as acetonitrile, THF, dichloromethane, chloroform, benzene and toluene. Furthermore, the reaction can be carried out in the presence of bases such as pyridine, lutidine and collidine. In general, the reaction is carried out in the range of from −20° C. up to the reflux temperature of the reaction mixture.

Scheme 12 shows the preparation of compounds represented by general formula (I) wherein D is —(CH$_2$)$_n$—S—(CH$_2$)$_m$—.

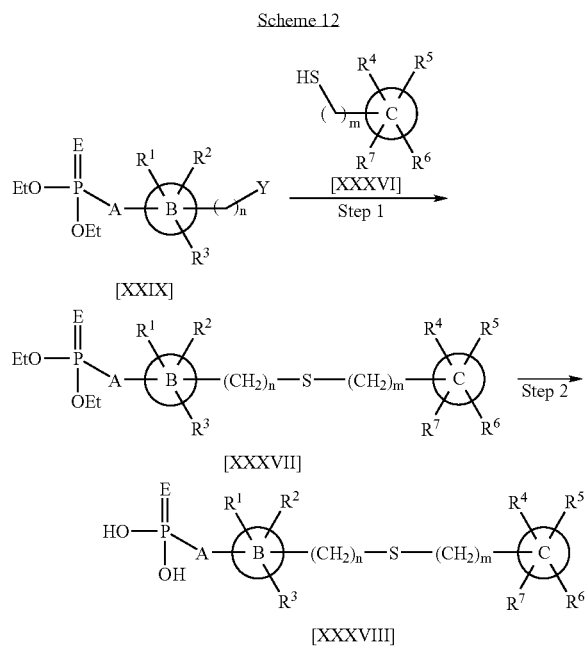

Scheme 12: wherein: Y is halogen atom, methanesulfonyl group, p-toluenesulfonyl group or trifluoromethanesulfonyl group. R$^1$~R$^7$, A, B, C, E, m and n as defined above.

Step 1: Compound (XXXVII) can be obtained by the reaction of compound (XXIX) with compound (XXXVI). The reaction is carried out in the presence of bases such as sodium hydride, potassium hydride, sodium hydroxide, potassium hydroxide, sodium carbonate, potassium carbonate, triethylamine and pyridine. In general, the reaction is carried out in an inert solvent. Preferred reaction solvents for use in this reaction include benzene, toluene, dioxane, THF, chloroform, DMF and DMSO and acetonitrile. In general, the reaction is carried out in the range of from room temperature up to the reflux temperature of the reaction mixture.

Step 2: Compound (XXXVIII) can be obtained by the hydrolysis or transesterification of compound (XXXVII). In hydrolysis under acidic conditions, hydrochloric acid, sulfuric acid and trifluoroacetic acid are used. On the other hand, lithium hydroxide, sodium hydroxide, potassium hydroxide, calcium hydroxide and barium hydroxide are used in hydrolysis under basic conditions. In general, the reaction is carried out in an inert solvent. Preferred reaction solvents for use in this reaction include water, methanol, ethanol, THF and 1,4-dioxane. In general, the reaction is carried out in the range of from 0° C. up to the reflux temperature of the reaction mixture. Alternatively, compound (XXXVIII) can be obtained by the transesterification of compound (XXXVII). Chlorotrimethylsilane-sodium iodide, bromotrimethylsilane and iodotrimethylsilane can be used in this reaction. In general, the reaction is carried out in an inert solvent. Preferred reaction solvents for use in this reaction are aprotic solvents such as acetonitrile, THF, dichloromethane, chloroform, benzene and toluene. Furthermore, the reaction can be carried out in the presence of bases such as pyridine, lutidine and collidine. In general, the reaction is carried out in the range of from −20° C. up to the reflux temperature of the reaction mixture.

The phosphonic acid derivatives represented by general formula (I) in the present invention synthesized by the methods in scheme 1~12 are isolated using extraction, concentration, evaporation, cystallization, filtration, recrystallization and chromatography etc.

The salts of the phosphonic acid derivatives represented by general formula (I) can be prepared by treatment with inorganic or organic addition bases such as lithium hydroxide, sodium hydroxide, potassium hydroxide, calcium hydroxide, magnesium hydroxide, ammonia, isopropylamine, diethylamine, triethylamine, ethanolamine, piperidine, pyridine, tris(hydroxymethyl)methylamine, tris(hydroxyethyl)methylamine, lysine and choline. Furthermore, the compounds may be present as solvates such as a hydrate.

The phosphonic acid derivatives represented by general formula (I) in the present invention and their pharmaceutically acceptable salts may be administered alone or combination with pharmaceutically acceptable carriers or diluent (diluents; starch, lactose, sucrose, calcium carbonate, calcium phosphate: binders; soluble starch, acacia, carboxymethylcellulose, hydroxypropylcellulose, crystalline cellulose, alginic acid, gelatin, polyvinylpyridone: lubricants; stearic acid, magnesium stearate, calcium stearate, talc: disintegrators; carboxymethylcellulose, talc: diluting agents; saline). The compounds of the present invention may be administered orally or parenterally. They may be combined with various pharmaceutically acceptable inert carriers in the form of powders, granule subtilaes, capsules, tablets, external applications and injections.

The dosage of the above-mentioned composition of this invention differs according to the route of administration, type and degree of the disease, subject's symptoms, weight and age, and the compound used, and the dosage can be set properly according to the purpose of administration. Generally, the daily dose of oral administration to an adult is from 0.01 to 1000 mg/kg/day, preferably from 0.05 to 500 mg/kg/day, and may be administered from 1 to several times per day. Also, although it is possible to administer it parenterally, for example into the rectum directly, this is only one example. However this invention is not limited by these examples.

The phosphonic acid derivatives or their pharmaceutically acceptable salts shown by general formula (I) in this invention have an excellent serum phosphate lowering effect. Therefore, the phosphonic acid derivatives or their pharmaceutically acceptable salts in this invention are useful for the treatment of diseases thought to be related to high levels of serum phosphate.

Also, a further effect of the phosphonic acid derivatives or their pharmaceutically acceptable salts shown by general formula (I) in this invention can be expected as the therapeutic agent of the disease related to high levels of serum phosphate by combination with other therapeutic agents of the disease related to high levels of serum phosphate. The phosphorus sequestrants are preferable as other therapeutic agents of the disease related to serum high phosphate. Moreover, an aluminum preparation (e.g. dried aluminum hydroxide gel etc.), calcium preparation (e.g. precipitated calcium carbonate, calcium lactate, calcium acetate etc.) or polycationpolymer (e.g. Sevelamer Hydrochloride etc.) are preferable as the phosphate sequestrants.

Stability Test Against Human Alkaline Phosphates

Compound 42 or 2'-PP was dissolved in dimethyl sulfoxide and the concentration was adjusted to $1 \times 10^{-2}$ M. 10 uL of the solution was added to 90 uL of Human alkaline phosphatase solution adjusted to 2 U/mL with 0.1 M carbonate buffer, and the mixture was incubated for 2 hours at 37° C. The amounts of each compound were measured by the HPLC method (HPLC condition, column: Inertsil ODS-2, eluent: 10 mM phosphate buffer/$CH_3CN$=8/2, wavelength: 230 nm, flow rate: 1 mL/min). The results are shown in Table 1.

TABLE 1

| Time (hr) | Compound 42 | 2'-PP |
| --- | --- | --- |
| 0 | 100.0 | 100.0 |
| 0.25 | 96.3 | 31.4 |
| 0.5 | 96.0 | 21.4 |
| 1 | 95.8 | 16.3 |
| 2 | 95.5 | 1.2 |

These results indicate that compound 42 in the present invention is stable against human alkaline phosphatase.

EVALUATION OF INHIBITORY EFFECT ON THE ELEVATION OF SERUM PHOSPHATE LEVELS IN $NaH_2PO_4$ LOADED MICE Male ddY mice, aged 6-7 weeks, were fasted overnight and used as 6 mice/group. The compounds suspended in 0.5% methylcellulose were administered orally at a dose of 100 or 300 mg/10 mL/kg. After 0.5 hours, 50 mg/300 uL/mouse of $NaH_2PO_4$ solution was administered orally. Blood samples were taken from retroorbital venousplexus of the mice before administration of the compounds and 0.5, 1, 2 and 4 hours after the $NaH_2PO_4$ administration, and serum phosphate concentration was measured using phospha C-test Wako kit (Wako pure chemicals Co. Ctd.). The area under the serum phosphate concentration-time curve (AUC) up to 4 hours after administration of $NaH_2PO_4$ was calculated and the inhibitory effect of serum phosphate levels was evaluated. The results are shown in Table 2.

TABLE 2

| Compd. No. | $ED_{30}$ (mg/kg) |
| --- | --- |
| 20 | 243.8 |
| 38 | 44.5 |
| 42 | 33.3 |
| 45 | 20.1 |
| 46 | 16.3 |
| 49 | 17.8 |
| 54 | 13.9 |
| 57 | 30.9 |
| 60 | 12.1 |
| 64 | 164.9 |
| 65 | 256.2 |
| 70 | 20.3 |
| 73 | 4.5 |
| 75 | 25.6 |
| 76 | 2.0 |
| 83 | 10.7 |

EXAMPLES

The synthetic methods of the compounds of the present invention are illustrated with the following Examples but are not limited thereby. Proton nuclear magnetic resonance ($^1$H NMR) spectra were measured at 400 MHz. Chemical shifts were expressed in parts per million relative to internal tetramethylsilane ($\delta$=0). The following abbreviations were used: s, singlet; d, doublet; t, triplet; q, quartet; dd, double of doublet; bs, broad singlet; m, multiplet.

Example 1

[5-(4-Ethylbenzyl)-2-hydroxyphenyl]phosphonic acid (compound 1)

(1)
[2-Benzyloxy-5-(4-ethylbenzyl)phenyl]phosphonic acid diethylester

To a solution a solution of [2-benzyloxy]-5-(4-ethylbenzyl)bromobenzene (5.00 g) in THF (36.5 mL) was added 2.44 M n-butyllithium/n-hexane solution (6.5 mL) at −78° C. and the reaction mixture was stirred for 1 hr at the same temperature. A solution of diethyl chlorophosphate (2.3 mL) in THF (5.6 mL) was added to the reaction mixture at −78° C. and the reaction mixture was stirred for 1 hr at −78° C. The reaction was quenched by the addition of saturated aqueous ammonium chloride and extracted with ethyl acetate. The combined ethyl acetate extracts were washed with brine, dried over anhydrous sodium sulfate and evaporated. The residue was purified by silica gel column chromatography (ethyl acetate/n-hexane) to give title compound (5.40 g) as a colorless oil.

$^1$H-NMR ($\delta$) $CDCl_3$; 1.21 (t, 3H, J=7 Hz), 1.26 (t, 6H, J=8 Hz), 2.60 (q, 2H, J=8 Hz), 3.90 (s, 2H), 4.02-4.25 (m, 4H), 5.14 (s, 2H), 6.87 (dd, 1H, J=7 Hz, 8 Hz), 7.08 (q, 4H, J=7 Hz), 7.49 (d, 2H, J=8 Hz), 7.71 (dd, 1H, J=2 Hz, 15 Hz). MS (m/z); 438 ($M^+$), 409, 348, 301, 275, 223, 195, 169, 119, 91 (Base peak).

(2) [5-(4-Ethylbenzyl)-2-hydroxybenzyl]phosphonic acid diethylester

To a solution of [2-benzyloxy-5-(4-ethylbenzyl)phenyl] phosphonic acid diethylester (2.08 g) in methanol (10.0 mL) was added 5% Pd—C (0.21 g) and the reaction mixture was stirred for 8 hr at room temperature under a hydrogen gas atmosphere. After filtration and evaporation, the residue was purified by silica gel column chromatography (ethyl acetate/n-hexane) to give the title compound (1.27 g) as a colorless crystal.

$^1$H-NMR (δ) CDCl$_3$; 1.21 (t, 3H, J=8 Hz), 1.28 (t, 6H, J=7 Hz), 2.60 (q, 2H, J=8 Hz), 3.87 (s, 2H), 3.97-4.16 (m, 4H), 6.85-6.90 (m, 1H), 7.04 (d, 2H, J=8 Hz), 7.10 (d, 2H, J=8 Hz), 7.14-7.23 (m, 2H), 7.25 (s, 1H), 10.05 (s, 1H). MS (m/z); 348 (M$^+$), 320, 291, 263, 239, 211, 169, 119, 91 (Base peak).

(3) [5-(4-Ethylbenzyl)-2-hydroxyphenyl]phosphonic acid (compound 1)

To a solution of [5-(4-ethylbenzyl)-2-hydroxybenzyl]phosphonic acid diethylester (0.50 g) in dichloromethane (19.0 mL) was added bromotrimethylsilane (1.9 mL) at 0° C., and the reaction mixture was stirred for 24 hr at room temperature. Methanol (5.0 mL) was added to the reaction mixture, and the mixture was stirred for 10 min at room temperature. After evaporation, the residue was crystallized from ethyl acetate-n-hexane to give the title compound (0.33 g) as a colorless crystal.

$^1$H-NMR (δ) CD$_3$OD; 1.18 (t, 3H, J=8 Hz), 2.57 (q, 2H, J=8 Hz), 3.84 (s, 2H), 6.77 (dd, 1H, J=2 Hz, 8 Hz), 7.00 (d, 2H, J=9 Hz), 7.10 (d, 2H, J=9 Hz), 7.19 (dd, 1H, J=2 Hz, 8 Hz), 7.37 (dd, 1H, J=2 Hz, 15 Hz). ESI-MS (m/z); 291 [M−H]$^-$.

Example 2

[2,4-Dimethoxy-5-(4-ethylbenzyl)phenyl]phosphonic acid (compound 2)

(1) [2,4-Dimethoxy-5-(4-ethylbenzyl)phenyl]phosphonic acid diethylester

To a solution of [2,4-dimethyoxy-5-(4-ethylbenzyl)bromobenzene (1.50 g) in THF (11.8 mL) was added 2.44 M n-butyllithium/n-hexane solution (2.2 mL) at −78° C., and the reaction mixture was stirred for 1 hr at −78° C. A solution of diethyl chlorophosphate (0.78 mL) in THF (1.0 mL) was added to the reaction mixture at −78° C., and the reaction mixture was stirred for 1 hr at −78° C. The reaction was quenched by the addition of saturated aqueous ammonium chloride and extracted with ethyl acetate. The combined ethyl acetate extracts were washed with brine, dried over anhydrous sodium sulfate and evaporated. The residue was purified by silica gel column chromatography (ethyl acetate/n-hexane) to give the title compound (1.02 g) as a colorless oil.

$^1$H-NMR (δ) CDCl$_3$; 1.20 (t, 3H, J=8 Hz), 1.28 (t, 6H, J=7 Hz), 2.59 (q, 2H, J=8 Hz), 3.85 (s, 5H), 3.89 (s, 3H), 4.03-4.12 (m, 4H), 6.43 (d, 1H, J=6 Hz), 7.08 (s, 4H), 7.52 (d, 1H, J=15 Hz).

MS (m/z); 392 (M$^+$), 363 317, 289, 255, 231, 201, 165, 119, 83 (Base peak).

(3) [2,4-Dimethoxy-5-(4-ethylbenzyl)phenyl]phosphonic acid (compound 2)

To a solution of [2,4-dimethoxy-5-(4-ethylbenzyl)phenyl]phosphonic acid diethylester (1.00 g) in dichloromethane (13.4 mL) was added bromotrimethylsilane (1.3 mL) at 0° C., and the reaction mixture was stirred for 17 hr at room temperature. Methanol (4.1 mL) was added to the reaction mixture, and the mixture was stirred for 10 min at room temperature. After evaporation, the residue was crystallized from ethyl acetate-n-hexane to give the title compound (0.78 g) as a colorless crystal.

$^1$H-NMR (δ) CD$_3$OD; 1.17 (t, 3H, J=8 Hz), 2.55 (q, 2H, J=8 Hz), 3.82 (s, 2H), 3.87 (s, 3H), 3.89 (s, 3H), 6.63 (d, 1H, J=6 Hz), 7.02-7.04 (m, 4H), 7.46 (d, 1H, J=17 Hz). ESI-MS (m/z); 335 [M−H]$^-$.

Example 3

[5-(4-Ethylbenzyl)-2-methoxyphenyl]phosphonic acid (compound 3)

The title compound was synthesized from 1-bromo-3-(4-ethylbenzyl)-6-methoxybenzene as a starting material by the same procedure as described in Example 2.

$^1$H-NMR (δ) CD$_3$OD; 1.18 (t, 3H, J=8 Hz), 2.56 (q, 2H, J=8 Hz), 2.98 (d, 2H, J=21 Hz), 3.76 (s, 3H), 3.85 (s, 2H), 6.85 (d, 1H, J=8 Hz), 7.02-7.13 (m, 6H). ESI-MS (m/z); 319 [M−H]$^-$.

Example 4

5-(4-Ethoxybenzyl)-2-thiophenephosphonic acid (compound 64)

The title compound was synthesized from 2-bromo-5-(4-ethoxybenzyl)thiophene as a starting material by the same procedure as described in Example 2.

$^1$H-NMR (δ) CD$_3$OD; 1.34 (t, 3H, J=7 Hz), 3.97 (q, 2H, J=7 Hz), 4.09 (s, 2H), 6.80-6.84 (m, 3H), 7.11 (d, 2H, J=9 Hz), 7.36 (dd, 1H, J=4 Hz, 9 Hz). ESI-MS (m/z); 297 [M−H]$^-$.

Example 5

5-(Benzofuran-2-ylmethyl)-2-thiophenephosphonic acid (compound 66)

The title compound was synthesized from 5-(Benzofuran-2-ylmethyl)-2-bromothiophene as a starting material by the same procedure as described in Example 2.

$^1$H-NMR (δ) CD$_3$OD; 4.38 (s, 2H), 6.57 (s, 1H), 7.04 (s, 1H), 7.14-7.23 (m, 2H), 7.37-7.44 (m, 2H), 7.49 (d, 1H, J=7 Hz). ESI-MS (m/z); 295 [M−H]$^-$.

Example 6

5-(Benzo[b]thiophene-2-ylmethyl)-2-thiophenephosphonic acid (compound 68)

The title compound was synthesized from 5-benzo[b]thiophene-2-ylmethyl)-2-bromothiophene as a starting material by the same procedure as described in Example 2.

$^1$H-NMR (δ) CD$_3$OD; 4.49 (s, 2H), 7.02-7.04 (m, 1H), 7.16 (s, 1H), 7.23-7.32 (m, 2H), 7.42 (dd, 1H, J=2 Hz, 8 Hz), 7.69 (d, 1H, J=8 Hz), 7.76 (d, 1H, J=2 Hz). ESI-MS (m/z); 311 [M−H]$^-$.

Example 7

[5-(4-Ethylbenzyl)-2-hydroxybenzyl]phosphonic acid (compound 4)

(1) [2-Benzyloxy-5-(4-ethylbenzyl)benzyl]phosphonic acid diethylester

Triethyl phosphite (0.6 mL) was added to 2-benzyloxy-5-(4-ethylbenzyl)benzylchloride (1.00 g), and the mixture was stirred for 4 hr at 150-160° C. The mixture was purified by silica gel column chromatography (ethyl acetate/n-hexane=1/2) to give the title compound (1.09 g) as a colorless oil.

$^1$H-NMR (δ) CDCl$_3$; 1.16 (t, 6H, J=7 Hz), 1.21 (t, 3H, J=8 Hz), 2.60 (q, 2H, J=8 Hz), 3.26 (d, 2H, J=22 Hz), 3.89 (s, 2H), 3.91-3.98 (m, 4H), 5.05 (s, 2H), 6.82 (d, 1H, J=9 Hz), 6.83-6.99 (m, 1H), 7.06-7.09 (m, 4H), 7.15-7.17 (m, 1H), 7.31 (t, 1H, J=7 Hz), 7.37 (t, 2H, J=7 Hz), 7.44 (d, 2H, J=7 Hz). MS (m/z); 452 (M$^+$), 361, 287, 195, 165, 119, 91 (Base peak).

(2) [5-(4-Ethylbenzyl)-2-hydroxybenzyl]phosphonic acid diethylester

To a solution of [2-benzyloxy-5-(4-ethylbenzyl)benzyl]phosphonic acid diethylester (1.03 g) in methanol (10.0 mL) was added 5% Pd—C (0.10 g), and the reaction mixture was stirred for 5 hr at room temperature under hydrogen gas atmosphere. After filtration and evaporation, the residue was purified by silica gel column chromatography (ethyl acetate/n-hexane=2/3) to give the title compound (0.80 g) as a colorless oil.

$^1$H-NMR (δ) CDCl$_3$; 1.17-1.23 (m, 9H), 2.60 (q, 2H, J=7 Hz), 3.15 (d, 2H, J=21 Hz), 3.84 (s, 2H), 3.91-4.06 (m, 4H), 6.85 (s, 1H), 6.90 (d, 1H, J=8 Hz), 6.98-7.10 (m, 5H), 8.33 (s, 1H).

MS (m/z); 362 (M$^+$), 316, 287, 259, 223, 195, 165, 142, 119, 91 (Base peak).

(3) [5-(4-Ethylbenzyl)-2-hydroxybenzyl]phosphonic acid (compound 4)

To a solution of [5-(4-ethylbenzyl)-2-hydroxybenzyl]phosphonic acid diethylester (0.40 g) in dichloromethane (7.8 mL) was added bromotrimethylsilane (0.8 mL) at 0° C., and the reaction mixture was stirred for 17 hr at room temperature. Methanol (1.1 mL) was added to the reaction mixture, and the mixture was stirred for 10 min at room temperature. After evaporation, the residue was crystallized from ethyl acetate-n-hexane to give the title compound (0.29 g) as a colorless crystal.

$^1$H-NMR (δ) CD$_3$OD; 1.18 (t, 3H, J=8 Hz), 2.56 (q, 2H, J=8 Hz), 3.11 (d, 2H, J=22 Hz), 3.79 (s, 2H), 6.70 (d, 1H, J=8 Hz), 6.84 (dd, 1H, J=2 Hz, 8 Hz), 7.05-7.08 (m, 5H). ESI-MS (m/z); 305 [M−H]$^-$.

Example 8

[3-(4-Ethylbenzyl)-4-hydroxybenzyl]phosphonic acid (compound 5)

The title compound was synthesized from 4-benzyloxy-5-(4-ethylbenzyl)benzyl chloride as a starting material by the same procedure as described in Example 7.

$^1$H-NMR (δ) CD$_3$OD; 1.18 (t, 3H, J=8 Hz), 2.56 (q, 2H, J=8 Hz), 2.95 (d, 2H, J=21 Hz), 3.85 (s, 2H), 6.70 (d, 1H, J=9 Hz), 6.96 (dd, 2H, J=2 Hz, 8 Hz), 6.92-6.96 (m, 2H), 7.03 (d, 2H, J=8 Hz), 7.11 (d, 2H, J=8 Hz). ESI-MS (m/z); 305 [M−H]$^-$.

Example 9

[3-(2-Ethoxybenzyl)-4-hydroxybenzyl]phosphonic acid (compound 18)

The title compound was synthesized from 4-benzyloxy-3-(2-ethoxybenzyl)benzyl chloride as a starting material by the same procedure as described in Example 7.

$^1$H-NMR (δ) CD$_3$OD; 1.40 (t, 3H, J=7 Hz), 2.90 (d, 2H, J=21 Hz), 3.88 (s, 2H), 4.03 (q, 2H, J=7 Hz), 6.69 (d, 1H, J=8 Hz), 6.77 (t, 1H, J=8 Hz), 6.86 (d, 1H, J=8 Hz), 6.96 (m, 2H), 7.04-7.10 (m, 2H). ESI-MS (m/z); 321 [M−H]$^-$.

Example 10

[3-(3-Ethoxybenzyl)-4-hydroxybenzyl]phosphonic acid (compound 19)

The title compound was synthesized from 4-benzyloxy-3-(3-ethoxybenzyl)benzyl chloride as a starting material by the same procedure as described in Example 7.

$^1$H-NMR (δ) CD$_3$OD; 1.31 (t, 3H, J=7 Hz), 2.91 (d, 2H, J=21 Hz), 3.86 (s, 2H), 3.93 (q, 2H, J=7 Hz), 6.65 (d, 1H, J=9 Hz), 6.69 (d, 1H, J=9 Hz), 6.96-6.98 (m, 2H), 7.07-7.11 (m, 1H). ESI-MS (m/z); 321 [M−H]$^-$.

Example 11

[3-(4-Ethoxybenzyl)-4-hydroxybenzyl]phosphonic acid (compound 20)

The title compound was synthesized from 4-benzyloxy-3-(4-ethoxybenzyl)benzyl chloride as a starting material by the same procedure as described in Example 7.

$^1$H-NMR (δ) CD$_3$OD; 1.34 (t, 3H, J=7 Hz), 2.94 (d, 2H, J=21 Hz), 3.82 (s, 2H), 3.96 (q, 2H, J=7 Hz), 6.69 (d, 1H, J=8 Hz), 6.75 (d, 2H, J=8 Hz), 6.95-6.96 (m, 2H), 7.10 (d, 2H, J=8 Hz). ESI-MS (m/z); 321 [M−H]$^-$.

Example 12

[5-(4-Ethoxybenzyl)-2-hydroxybenzyl]phosphonic acid (compound 21)

The title compound was synthesized from 2-benzyloxy-5-(4-ethoxybenzyl)benzyl chloride as a starting material by the same procedure as described in Example 7.

$^1$H-NMR (δ) CD$_3$OD; 1.33 (t, 3H, J=7 Hz), 3.08 (d, 2H, J=21 Hz), 3.77 (s, 2H), 3.94 (q, 2H, J=7 Hz), 6.68 (d, 1H, J=8 Hz), 6.75-6.78 (m, 2H), 6.83 (d, 1H, J=8 Hz), 7.04 (d, 3H, J=8 Hz). ESI-MS (m/z); 321 [M−H]$^-$.

Example 13

[3-(4-Ethoxyphenoxy)-4-hydroxybenzyl]phosphonic acid (compound 26)

The title compound was synthesized from 4-benzyloxy-3-(4-ethoxyphenoxy)benzyl chloride as a starting material by the same procedure as described in Example 7.

$^1$H-NMR (δ) CD$_3$OD; 1.36 (t, 3H, J=7 Hz), 2.94 (d, 2H, J=21 Hz), 3.98 (q, 2H, J=7 Hz), 6.78 (t, 1H, J=2 Hz), 6.82-6.91 (m, 6H). ESI-MS (m/z); 323 [M−H]$^-$.

Example 14

[5-(4-Ethoxyphenoxy)-2-hydroxybenzyl]phosphonic acid (compound 27)

The title compound was synthesized from 2-benzyloxy-5-(4-ethoxyphenoxy)benzyl chloride as a starting material by the same procedure as described in Example 7.

$^1$H-NMR (δ) CD$_3$OD; 1.20 (t, 3H, J=8 Hz), 2.58 (q, 2H, J=8 Hz), 3.13 (d, 2H, J=22 Hz), 6.68-6.72 (m, 1H), 6.76-6.83 (m, 3H), 6.93-6.59 (m, 1H), 7.10 (d, 2H, J=9 Hz). ESI-MS (m/z); 307 [M−H]$^-$.

Example 15

[5-(4-t-Butylbenzyl)-2-hydroxybenzyl]phosphonic acid (compound 29)

The title compound was synthesized from 2-benzyloxy-5-(4-t-butylbenzyl)benzyl chloride as a starting material by the same procedure as described in Example 7.

$^1$H-NMR (δ) CD$_3$OD; 1.28 (s, 9H), 3.13 (d, 2H, J=21 Hz), 3.80 (s, 2H), 6.70 (d, 1H, J=8 Hz), 6.86 (d, 1H, J=8 Hz), 7.05-7.08 (m, 3H), 7.26 (d, 2H, J=9 Hz). ESI-MS (m/z); 333 [M−H]$^-$.

Example 16

[2-Hydroxy-5-(naphtalen-2-ylmethyl)benzyl]phosphonic acid (compound 31)

The title compound was synthesized from 2-benzyloxy-5-(naphthalen-2-ylmethyl)benzyl chloride as a starting material by the same procedure as described in Example 7.

$^1$H-NMR (δ) CD$_3$OD; 2.95 (d, 2H, J=21 Hz), 4.07 (s, 2H), 6.74 (d, 1H, J=8 Hz), 7.00-7.03 (m, 2H), 7.34-7.40 (m, 3H), 7.63 (s, 1H), 7.68-7.75 (m, 3H). ESI-MS (m/z); 327 [M−H]$^-$.

Example 17

[5-(4-Ethylbenzyl)-2-fluorobenzyl]phosphonic acid (compound 7)

(1) [5-(4-Ethylbenzyl)-2-fluorobenzyl]phosphonic acid diethylester

Triethyl phosphite (0.8 mL) was added to [5-(4-ethylbenzyl)-2-fluorobenzyl chloride (0.65 g), and the mixture was stirred for 16 hr at 150-160° C. The mixture was purified by silica gel column chromatography (ethyl acetate/n-hexane=1/1) to give the title compound (0.70 g) as a colorless oil.

$^1$H-NMR (δ) CDCl$_3$; 1.19-1.23 (m, 9H), 2.57 (q, 2H, J=8 Hz), 3.12 (d, 2H, J=21 Hz), 3.88 (s, 2H), 3.97-4.04 (m, 4H), 6.92 (t, 1H, J=9 Hz), 7.00-7.17 (m, 6H). MS (m/z); 364 (M$^+$), 335, 307, 260, 209, 183, 161, 133, 109, 84 (Base peak).

(2) [5-(4-Ethylbenzyl)-2-fluorobenzyl]phosphonic acid (compound 7)

To a solution of [5-(4-ethylbenzyl)-2-fluorobenzyl]phosphonic acid diethylester (0.70 g) in dichloromethane (12.0 mL) was added bromotrimethylsilane (1.2 mL) at 0° C., and the reaction mixture was stirred for 18 hr at room temperature. Methanol (7.0 mL) was added to the reaction mixture, and the mixture was stirred for 10 min at room temperature. After evaporation, the residue was crystallized from ethyl acetate-n-hexane to give the title compound (0.53 g) as a colorless crystal.

$^1$H-NMR (δ) CD$_3$OD; 1.17 (t, 3H, J=8 Hz), 2.55 (q, 2H, J=8 Hz), 3.06 (d, 2H, J=21 Hz), 3.87 (s, 2H), 6.92 (t, 1H, J=9 Hz), 7.00 (bs, 1H), 7.08 (s, 4H), 7.23 (d, 1H, J=7 Hz). ESI-MS (m/z); 307 [M−H]$^-$.

Example 18

[2-Chloro-5-(4-ethylbenzyl)benzyl]phosphonic acid (compound 8)

The title compound was synthesized from 2-chloro-5-(4-ethylbenzyl)benzyl chloride as a starting material by the same procedure as described in Example 17.

$^1$H-NMR (δ) CD$_3$OD; 1.19 (t, 3H, J=8 Hz), 2.57 (q, 2H, J=8 Hz), 3.27 (d, 2H, J=20 Hz), 3.88 (s, 2H), 6.99 (d, 1H, J=8 Hz), 7.02 (d, 2H, J=8 Hz), 7.10 (d, 2H, J=8 Hz), 7.25 (d, 1H, J=8 Hz), 7.32 (s, 1H). ESI-MS (m/z); 323 [M−H]$^-$.

Example 19

[5-(4-Ethylbenzyl)-2-methylbenzyl]phosphonic acid (compound 9)

The title compound was synthesized from 5-(4-ethylbenzyl)-2-methylbenzyl chloride as a starting material by the same procedure as described in Example 17.

$^1$H-NMR (δ) CD$_3$OD; 1.16 (t, 3H, J=8 Hz), 2.33 (s, 3H), 2.54 (q, 2H, J=8 Hz), 3.06 (d, 2H, J=22 Hz), 3.84 (s, 2H), 6.89 (d, 1H, J=8 Hz), 7.02-7.06 (m, 5H), 7.12 (s, 1H). ESI-MS (m/z); 303 [M−H]$^-$.

Example 20

[5-(4-Ethylbenzyl)-2-methoxybenzyl]phosphonic acid (compound 10)

The title compound was synthesized from 5-(4-ethylbenzyl)-2-methoxybenzyl chloride as a starting material by the same procedure as described in Example 17.

$^1$H-NMR (δ) CD$_3$OD; 1.18 (t, 3H, J=8 Hz), 2.57 (q, 2H, J=8 Hz), 3.12 (d, 2H, J=22 Hz), 3.79 (s, 3H), 6.83 (d, 1H, J=8 Hz), 6.98 (d, 2H, J=8 Hz), 7.05-7.07 (m, 4H), 7.15 (s, 1H). ESI-MS (m/z); 319 [M−H]$^-$.

Example 21

[2,4-Dimethoxy-5-(4-ethylbenzyl)benzyl]phosphonic acid (compound 11)

The title compound was synthesized from 2,4-dimethoxy-5-(4-ethylbenzyl)benzyl chloride as a starting material by the same procedure as described in Example 17.

$^1$H-NMR (δ) CD$_3$OD; 1.18 (t, 3H, J=8 Hz), 2.55 (q, 2H, J=8 Hz), 3.06 (d, 2H, J=21 Hz), 3.79 (s, 3H), 3.83 (s, 5H), 6.57 (s, 1H), 7.01-7.07 (m, 5H). ESI-MS (m/z); 349 [M−H]$^-$.

Example 22

[4-Chloro-3-(4-ethylbenzyl)benzyl]phosphonic acid (compound 12)

The title compound was synthesized from 4-chloro-3-(4-ethylbenzyl)benzyl chloride as a starting material by the same procedure as described in Example 17.

$^1$H-NMR (δ) CD$_3$OD; 1.17 (t, 3H, J=8 Hz), 2.55 (q, 2H, J=8 Hz), 3.01 (d, 2H, J=21 Hz), 4.00 (s, 2H), 7.06-7.08 (m, 4H), 7.13-7.20 (m, 2H), 7.27-7.29 (m, 1H). ESI-MS (m/z); 323 [M−H]$^-$.

Example 23

3-(4-Ethylbenzyl)-4-methoxybenzyl]phosphonic acid (compound 13)

The title compound was synthesized from 3-(4-ethylbenzyl)-4-methoxybenzyl chloride as a starting material by the same procedure as described in Example 17.

$^1$H-NMR (δ) CD$_3$OD; 1.18 (t, 3H, J=8 Hz), 2.56 (q, 2H, J=8 Hz), 2.98 (d, 2H, J=21 Hz), 3.76 (s, 3H), 3.85 (s, 2H), 6.85 (d, 1H, J=8 Hz), 7.02-7.13 (m, 6H). ESI-MS (m/z); 319 [M−H]$^-$.

Example 24

[4-Ethoxy-3-(4-ethylbenzyl)benzyl]phosphonic acid (compound 14)

The title compound was synthesized from 4-ethylbenzyl-3-(4-ethylbenzyl)benzyl chloride as a starting material by the same procedure as described in Example 17.

$^1$H-NMR ($\delta$) CD$_3$OD; 1.15 (t, 3H, J=7 Hz), 1.30 (t, 3H, J=7 Hz), 2.53 (q, 2H, J=7 Hz), 2.96 (d, 2H, J=21 Hz), 3.86 (s, 2H), 3.94 (q, 2H, J=7 Hz), 6.81 (d, 1H, J=8 Hz), 7.01-7.10 (m, 6H). ESI-MS (m/z); 333 [M−H]$^-$.

Example 25

[3-(4-Ethylbenzyl)-4-n-propoxybenzyl]phosphonic acid (compound 15)

The title compound was synthesized from 3-(4-ethylbenzyl)-4-n-propoxybenzyl chloride as a starting material by the same procedure as described in Example 17.

$^1$H-NMR ($\delta$) CD$_3$OD; 0.94 (t, 3H, J=7 Hz), 1.15 (t, 3H, J=8 Hz), 1.71-1.76 (m, 2H), 2.53 (q, 2H, J=8 Hz), 2.96 (d, 2H, J=21 Hz), 3.85-3.88 (m, 4H), 6.80 (d, 1H, J=8 Hz), 7.01-7.10 (m, 6H). ESI-MS (m/z); 347 [M−H]$^-$.

Example 26

[3-(4-Ethylbenzyl)-4-i-propoxybenzyl]phosphonic acid (compound 16)

The title compound was synthesized from 3-(4-ethylbenzyl)-4-i-propoxybenzyl chloride as a starting material by the same procedure as described in Example 17.

$^1$H-NMR ($\delta$) CD$_3$OD; 1.15-1.23 (m, 9H), 2.53 (q, 2H, J=8 Hz), 2.96 (d, 2H, J=20 Hz), 3.83 (s, 2H), 4.51-4.54 (m, 1H), 6.82 (d, 1H, J=9 Hz), 7.01-7.10 (m, 6H). ESI-MS (m/z); 347 [M−H]$^-$.

Example 27

[4-Benzyloxy-3-(4-ethylbenzyl)benzyl]phosphonic acid (compound 17)

The title compound was synthesized from 4-benzyloxy-3-(4-ethylbenzyl)benzyl chloride as a starting material by the same procedure as described in Example 17.

$^1$H-NMR ($\delta$) CD$_3$OD; 1.18 (t, 3H, J=8 Hz), 2.54 (q, 2H, J=8 Hz), 2.97 (d, 2H, J=20 Hz), 3.91 (s, 2H), 5.01 (s, 2H), 6.88 (d, 1H, J=8 Hz), 7.01-7.11 (m, 6H), 7.22-7.2.8 (m, 5H). ESI-MS (m/z); 395 [M−H]$^-$.

Example 28

[3-(4-Ethoxybenzyl)-4-fluorobenzyl]phosphonic acid (compound 23)

The title compound was synthesized from 3-(4-ethoxybenzyl)-4-fluorobenzyl chloride as a starting material by the same procedure as described in Example 17.

$^1$H-NMR ($\delta$) CD$_3$OD; 1.34 (t, 3H, J=7 Hz), 3.03 (d, 2H, J=21 Hz), 3.87 (s, 2H), 3.97 (q, 2H, J=7 Hz), 6.78 (d, 2H, J=8 Hz), 6.92 (t, 1H, J=8 Hz), 7.08-7.15 (m, 4H). ESI-MS (m/z); 323 [M−H]$^-$.

Example 29

[4-Chloro-3-(4-ethoxybenzyl)benzyl]phosphonic acid (compound 24)

The title compound was synthesized from 4-chloro-3-(4-ethoxybenzyl)benzyl chloride as a starting material by the same procedure as described in Example 17.

$^1$H-NMR ($\delta$) CD$_3$OD; 1.33 (t, 3H, J=7 Hz), 3.01 (d, 2H, J=22 Hz), 3.95 (q, 2H, J=7 Hz), 6.77 (d, 2H, J=9 Hz), 7.06 (d, 2H, J=9 Hz), 7.13-7.18 (m, 2H), 7.27 (d, 1H, J=8 Hz). ESI-MS (m/z); 339 [M−H]$^-$.

Example 30

[2,4-Dimethoxy-5-(4-ethoxybenzyl)benzyl]phosphonic acid (compound 25)

The title compound was synthesized from 2,3-dimethoxy-5-(4-ethoxybenzyl)benzyl chloride as a starting material by the same procedure as described in Example 17.

$^1$H-NMR ($\delta$) CD$_3$OD; 1.34 (t, 3H, J=7 Hz), 3.04 (d, 2H, J=21 Hz), 3.76 (s, 2H), 3.79 (s, 3H), 3.83 (s, 3H), 3.95 (q, 2H, J=7 Hz), 6.57 (s, 1H), 6.73 (dd, 1H, J=2 Hz, 9 Hz), 7.02 (d, 1H, J=3 Hz), 7.04 (dd, 2H, J=2 Hz, 9 Hz). ESI-MS (m/z); 365 [M−H]$^-$.

Example 31

[3-(4-t-Butylbenzyl)-4-chlorobenzyl]phosphonic acid (compound 28)

The title compound was synthesized from 3-(4-t-butylbenzyl)-4-chlorobenzyl chloride as a starting material by the same procedure as described in Example 17.

$^1$H-NMR ($\delta$) CD$_3$OD; 1.27 (s, 9H), 3.02 (d, 2H, J=22 Hz), 4.02 (s, 2H), 7.09-7.15 (m, 3H), 7.21 (s, 1H), 7.26-7.30 (m, 3H). ESI-MS (m/z); 351 [M−H]$^-$.

Example 32

[4-Chloro-3-(naphtalen-2-ylmethyl)benzyl]phosphonic acid (compound 30)

The title compound was synthesized from 4-chloro-3-(naphthalen-2-ylmethyl)benzyl chloride as a starting material by the same procedure as described in Example 17.

$^1$H-NMR ($\delta$) CD$_3$OD; 2.88 (d, 2H, J=21 Hz), 4.21 (s, 2H), 7.20-7.41 (m, 6H), 7.59 (s, 1H), 7.72-7.77 (m, 3H). ESI-MS (m/z); 345 [M−H]$^-$.

Example 33

[3-(Benzofuran-2-ylmethyl)-4-chlorobenzyl]phosphonic acid (compound 32)

The title compound was synthesized from 3-(benzofuran-2-ylmethyl)-4-chlorobenzyl chloride as a starting material by the same procedure as described in Example 17.

$^1$H-NMR ($\delta$) CD$_3$OD; 3.05 (d, 2H, J=22 Hz), 4.22 (s, 2H), 6.39 (s, 1H), 6.39-7.23 (m, 3H), 7.32-7.38 (m, 3H). ESI-MS (m/z); 335 [M−H]$^-$.

Example 34

[3-(Benzo[b]thiophen-2-ylmethyl)-4-chlorobenzyl] phosphonic acid (compound 33)

The title compound was synthesized from 3-(benzo[b]thiophen-2-ylmethyl)-4-chlorobenzyl chloride as a starting material by the same procedure as described in Example 17.

$^1$H-NMR (δ) CD$_3$OD; 3.05 (d, 2H, J=22 Hz), 4.33 (s, 2H), 7.01 (s, 1H), 7.20-7.28 (m, 4H), 7.33 (d, 1H, J=8 Hz), 7.63 (d, 1H, J=7 Hz), 7.71 (d, 1H, J=8 Hz). ESI-MS (m/z); 351 [M−H]$^-$.

Example 35

[5-(4-Ethoxybenzyl)thiophen-2-ylmethyl]phosphonic acid (compound 65)

The title compound was synthesized from 2-chloromethyl-5-(4-ethoxybenzyl)thiophene as a starting material by the same procedure as described in Example 17.

$^1$H-NMR (δ) CD$_3$OD; 1.35 (t, 3H, J=7 Hz), 3.21 (d, 2H, J=21 Hz), 3.96-4.01 (m, 4H), 6.61 (d, 1H, J=4 Hz), 3.74 (t, 1H, J=4 Hz), 6.80 (d, 2H, J=9 Hz), 7.11 (d, 2H, J=9 Hz). ESI-MS (m/z); 311 [M−H]$^-$.

Example 36

[5-(Benzofuran-2-ylmethyl)thiophen-2-ylmethyl] phosphonic acid (compound 67)

The title compound was synthesized from 5-(benzofuran-2-ylmethyl)-2-chloromethylthiophene as a starting material by the same procedure as described in Example 17.

$^1$H-NMR (δ) CD$_3$OD; 3.25 (d, 2H, J=21 Hz), 4.25 (s, 2H), 6.52 (s, 1H), 6.80 (s, 2H), 7.12-7.21 (m, 2H), 7.36 (d, 1H, J=7 Hz), 7.45 (d, 2H, J=7 Hz). ESI-MS (m/z); 307 [M−H]$^-$.

Example 37

[5-(Benzo[b]thiophen-2-ylmethyl)thiophen-2-ylmethyl]phosphonic acid (compound 69)

The title compound was synthesized from 5-(benzo[b]thiophen-2-ylmethyl)-2-chloromethylthiophene as a starting material by the same procedure as described in Example 17.

$^1$H-NMR (δ) CD$_3$OD; 3.25 (d, 2H, J=21 Hz), 4.36 (s, 2H), 6.79 (q, 2H, J=4 Hz), 7.11 (s, 2H), 7.21-7.30 (m, 2H), 7.66 (d, 1H, J=8 Hz), 7.73 (d, 2H, J=8 Hz). ESI-MS (m/z); 323 [M−H]$^-$.

Example 38

[3-(4-Ethylbenzyl)-4-(2-hydroxyethoxy)benzyl] phosphonic acid (compound 6)

(1) [4-(2-t-Butyldiphenysilyloxyethoxy)-3-(4-ethylbenzyl)phosphonic acid diethylester A mixture of [3-(4-ethylbenzyl)-4-hydroxybenzyl]phosphonic acid diethylester (1.00 g), potassium carbonate (0.45 g) and 2-(t-butyldiphenylsilyloxy)ethyl bromide (1.20 g) in DMF (20.0 mL) was stirred for 21 hr at 60° C. The mixture was poured into ice-water, and extracted with ethyl acetate. The combined ethyl acetate extracts were washed with water and brine, dried over anhydrous sodium sulfate and evaporated. The residue was purified by silica gel column chromatography (ethyl acetate/n-hexane=1/1) to give the title compound (1.43 g) as a colorless oil.

$^1$H-NMR (δ) CDCl$_3$; 1.05 (s, 9H), 1.19 (t, 9H, J=7 Hz), 2.57 (q, 2H, J=7 Hz), 3.02 (d, 2H, J=21 Hz), 3.91-3.98 (m, 8H), 4.06 (t, 2H, J=5 Hz), 6.75 (d, 1H, J=8 Hz), 6.96-7.11 (m, 6H), 7.32-7.43 (m, 6H), 7.66-7.70 (m, 4H). ESI-MS (m/z); 662 [M+(NH4)]$^+$.

(2) [3-(4-Ethylbenzyl)-4-(2-hydroxyethoxy)benzyl] phosphonic acid diethylester To a solution of [4-(2-t-butyldiphenysilyloxyethoxy)-3-(4-ethylbenzyl)phosphonic acid diethylester (1.43 g) in THF (10.0 mL) was added 1.0 M tetra-n-butylammonium fluoride/THF (2.6 mL), at 0° C. and the reaction mixture was stirred for 15.5 hr at room temperature. The mixture was diluted with ethyl acetate, washed with water and brine, dried over anhydrous sodium sulfate and evaporated. The residue was purified by silica gel column chromatography (ethyl acetate) to give the title compound (0.70 g) as a colorless oil.

$^1$H-NMR (δ) CDCl$_3$; 1.17-1.24 (m, 9H), 2.59 (q, 2H, J=8 Hz), 3.08 (d, 2H, J=21 Hz), 3.78-3.82 (m, 2H), 3.92 (s, 2H), 3.96-4.03 (m, 6H), 6.75 (d, 1H, J=8 Hz), 7.08-7.13 (m, 6H). MS (m/z); 407 (M$^+$), 377, 333, 301, 269, 225, 195, 165, 119 (Base peak), 91.

(3) [3-(4-Ethylbenzyl)-4-(2-hydroxyethoxy)benzyl] phosphonic acid (compound 6)

To a solution of [3-(4-ethylbenzyl)-4-(2-hydroxyethoxy)benzyl]phosphonic acid diethylester (0.70 g) in dichloromethane (11.0 mL) was added bromotrimethylsilane (1.1 mL) at 0° C., and the reaction mixture was stirred for 14 hr at room temperature. Methanol (6.0 mL) was added to the reaction mixture, and the mixture was stirred for 10 min at room temperature. Evaporation of the solvent gave the title compound (0.51 g) as a light gray oil.

$^1$H-NMR (δ) CD$_3$OD; 1.17 (t, 3H, J=8 Hz), 2.55 (q, 2H, J=8 Hz), 3.00 (d, 2H, J=20 Hz), 3.81 (t, 2H, J=5 Hz), 3.91 (s, 2H), 3.98 (t, 2H, J=5 Hz), 6.85 (d, 1H, J=8 Hz), 7.02-7.13 (m, 6H). ESI-MS (m/z); 349 [M−H]$^-$.

Example 39

[3-(4-Ethoxybenzyl)-4-(2-hydroxyethoxy)benzyl] phosphonic acid (compound 22)

The title compound was synthesized from 3-(4-ethoxybenzyl)-4-hydroxybenzyl]phosphonic acid diethylester as a starting material by the same procedure as described in Example 38.

$^1$H-NMR (δ) CD$_3$OD; 1.33 (t, 3H, J=7 Hz), 2.95 (d, 2H, J=21 Hz), 3.82 (t, 2H, J=5 Hz), 3.87 (s, 2H), 3.93-3.98 (m, 4H), 6.74 (d, 2H, J=8 Hz), 6.83 (d, 1H, J=8 Hz), 7.06-7.13 (m, 4H). ESI-MS (m/z); 365 [M−H]$^-$.

Example 40

2-[5-(4-Ethylbenzyl)-2-hydroxyphenyl]ethylphosphonic acid (compound 34)

(1) 2-[2-Benzyloxy-5-(4-ethylbenzyl)phenyl]ethylphosphonic acid diethylester To a solution of dimethyl methylphosphonate (0.7 mL) in THF (8.2 mL) was added 2.44 M n-butyllithium/n-hexane solution (2.6 mL) at −78° C., and the reaction mixture was stirred for 0.5 hr at −78° C. A solution of [2-benzyloxy-5-(4-ethylbenzyl)benzyl chloride (1.50 g) in THF (8.2 mL) was added to the mixture at −78° C., and the reaction mixture was stirred for 2 hr at −78° C.~−10° C. The reaction was quenched by the addition of saturated aqueous ammonium chloride and extracted with ethyl acetate. The combined ethyl acetate extracts were washed with brine, dried over anhydrous sodium sulfate and evaporated. The residue was purified by silica gel column chromatography (ethyl acetate/n-hexane=2/3) to give the title compound (0.74 g) as a colorless oil.

$^1$H-NMR ($\delta$) CDCl$_3$; 1.22 (t, 3H, J=8 Hz), 2.02-2.91 (m, 2H), 2.61 (q, 2H, J=8 Hz), 2.84-2.91 (m, 2H), 3.59 (s, 3H), 3.62 (s, 3H), 3.56 (s, 2H), 5.04 (s, 2H), 6.81 (d, 1H, J=9 Hz), 6.89-7.06 (m, 2H), 7.07 (d, 2H, J=8 Hz), 7.10 (d, 2H, J=8 Hz), 7.30-7.42 (m, 5H).

MS (m/z); 438 (M$^+$), 347, 319, 237, 209, 165, 119, 91 (Base peak).

(2) 2-[5-(4-Ethylbenzyl)-2-hydroxyphenyl]ethylphosphonic acid diethylester

To a solution of 2-[2-benzyloxy-5-(4-ethylbenzyl)phenyl]ethylphosphonic acid diethylester (0.71 g) in methanol (7.0 mL) was added 5% Pd—C (0.07 g), and the reaction mixture was stirred for 4.5 hr at room temperature under a hydrogen gas atmosphere. After filtration and evaporation, the residue was purified by silica gel column chromatography (ethyl acetate/n-hexane=2/3) to give the title compound (0.52 g) as a colorless oil.

$^1$H-NMR ($\delta$) CDCl$_3$; 1.21 (t, 3H, J=8 Hz), 2.08-2.17 (m, 2H), 2.60 (q, 2H, J=8 Hz), 3.63 (s, 3H), 3.66 (s, 3H), 3.83 (s, 2H), 6.78 (d, 1H, J=9 Hz), 6.89-6.91 (m, 2H), 7.05-7.11 (m, 4H), 7.31 (s, 1H). MS (m/z); 348 (M$^+$), 316 (Base peak), 287, 238, 209, 165, 119.

(3) -[5-(4-Ethylbenzyl)-2-hydroxyphenyl]ethylphosphonic acid (compound 34)

To a solution of 2-[5-(4-Ethylbenzyl)-2-hydroxyphenyl]ethylphosphonic acid diethylester (0.50 g) in ethanol (5.0 mL) was added 6N—HCl (5.0 mL), and the reaction mixture was refluxed for 24 hr. Evaporation and crystallization from ethyl acetate-n-hexane gave the title compound (0.40 g) as a colorless crystal.

$^1$H-NMR ($\delta$) CD$_3$OD; 1.19 (t, 3H, J=8 Hz), 1.92-2.01 (m, 2H), 2.57 (q, 2H, J=8 Hz), 2.78-2.85 (m, 2H), 3.78 (s, 2H), 6.65 (d, 1H, J=8 Hz), 6.82 (dd, 1H, J=2 Hz, 8 Hz), 6.89 (d, 1H, J=2 Hz), 7.03 (d, 2H, J=8 Hz), 7.07 (d, 2H, J=8 Hz). ESI-MS (m/z); 319 [M−H]$^-$.

Example 41

2-[5-(4-Ethylbenzyl)-2-methoxyphenyl]ethylphosphonic acid (compound 35)

The title compound was synthesized from [5-(4-ethylbenzyl)-2-methoxybenzyl chloride as a starting material by the same procedure as described in Example 40.

$^1$H-NMR ($\delta$) CD$_3$OD; 1.20 (t, 3H, J=8 Hz), 1.91-2.04 (m, 2H), 2.60 (q, 2H, J=8 Hz), 2.81-2.90 (m, 2H), 3.45 (s, 3H), 3.88 (s, 2H), 6.66 (d, 1H, J=8 Hz), 6.84 (dd, 1H, J=2 Hz, 8 Hz), 6.81 (d, 1H, J=2 Hz), 7.13 (d, 2H, J=8 Hz), 7.18 (d, 2H, J=8 Hz). ESI-MS (m/z); 333 [M−H]$^-$.

Example 42

{2-[3-(4-Ethoxybenzyl)-4-hydroxyphenyl]-2-oxoethyl}phosphonic acid (compound 36)

(1) {2-[3-(4-Ethoxybenzyl)-4-hydroxyphenyl]-2-oxoethyl}phosphonic acid diethylester To a solution of dimethyl methylphosphonate (0.68 mL) in THF (3.1 mL) was added 2.44 M n-butyllithium/n-hexane solution (2.5 mL) at −78° C., and the reaction mixture was stirred for 0.5 hr at −78° C. A solution of 3-(4-ethoxybenzyl)-4-methoxymethyloxybenzoic acid methylester (1.00 g) in THF (3.0 mL) was added to the mixture at −78° C., and the reaction mixture was stirred for 0.5 hr at −78° C. The reaction was quenched by the addition of saturated aqueous ammonium chloride and extracted with ethyl acetate. The combined ethyl acetate extracts were washed with brine, dried over anhydrous sodium sulfate and evaporated. The residue was purified by silica gel column chromatography (ethyl acetate/n-hexane=4/1) to give the title compound (1.00 g) as a colorless oil.

$^1$H-NMR ($\delta$) CDCl$_3$; 1.38 (t, 3H, J=7 Hz), 3.35 (s, 3H), 3.56 (d, 2H, J=22 Hz), 3.74 (s, 3H), 3.77 (s, 3H), 3.94 (s, 2H), 3.98 (q, 2H, J=7 Hz), 5.24 (s, 2H), 6.79 (d, 2H, J=9 Hz), 7.10 (d, 3H, J=9 Hz), 7.81 (d, 1H, J=2 Hz), 7.85 (dd, 1H, J=2 Hz, 9 Hz).

MS (m/z); 422 (M$^+$), 377, 239, 151 (Base peak), 109.

(2) {2-[3-(4-Ethoxybenzyl)-4-hydroxyphenyl]-2-oxoethyl}phosphonic acid (compound 36)

To a solution of {2-[3-(4-ethoxybenzyl)-4-hydroxyphenyl]-2-oxoethyl}phosphonic acid diethylester (1.00 g) in dichloromethane (4.7 mL) was added bromotrimethylsilane (1.6 mL) at 0° C., and the reaction mixture was stirred for 9 hr at room temperature. Methanol (4.0 mL) was added to the reaction mixture, and the mixture was stirred for 10 min at room temperature. Evaporation and crystallization from ethyl acetate-n-hexane gave the title compound (0.72 g) as a pale brown crystal.

$^1$H-NMR ($\delta$) CD$_3$OD; 1.35 (t, 3H, J=7 Hz), 3.51 (d, 2H, J=22 Hz), 3.88 (s, 2H), 3.97 (q, 2H, J=7 Hz), 6.77 (d, 2H, J=9 Hz), 6.83 (d, 1H, J=9 Hz), 7.12 (d, 2H, J=9 Hz), 7.77 (d, 1H, J=2 Hz), 7.79 (dd, 1H, J=2 Hz, 9 Hz). ESI-MS (m/z); 351 [M−H]$^-$.

Example 43

[4-Hydroxy-3-(4-phenoxybenzyl)benzoyl]phosphonic acid (compound 49)

(1) [4-Methoxymethyloxy-3-(4-phenoxybenzyl)phenyl]hydroxymethylphosphonic acid diethylester To a solution of 4-methoxymethyloxy-3-(4-phenoxybenzyl)benzaldehyde (3.00 g) in THF were added diethyl phosphite (1.1 mL) and sodium methoxide (0.02 g) at 0° C., and the reaction mixture was stirred for 0.5 hr at 0° C. The reaction was quenched by the addition of saturated aqueous ammonium chloride and extracted with ethyl acetate. The combined ethyl acetate extracts were washed with brine, dried over anhydrous sodium sulfate and evaporated. The residue was purified by silica gel column chromatography (ethyl acetate) to give the title compound (3.16 g) as a colorless oil.

$^1$H-NMR ($\delta$) CDCl$_3$; 1.18-1.27 (m, 6H), 2.63 (dd, 1H, J=5 Hz, 10 Hz), 3.36 (s, 3H), 3.92-4.06 (m, 6H), 4.91 (dd, 1H, J=5 Hz, 10 Hz), 5.15 (s, 2H), 6.88 (d, 2H, J=9 Hz), 6.94 (d, 1H, J=8 Hz), 7.04-7.31 (m, 9H).

(2) [4-Methoxymethyloxy-3-(4-phenoxybenzyl)phenyl]benzoyllphosphonic acid diethylester To a solution of oxalyl chloride (1.1 mL) in dichloromethane (9.0 mL) was added a solution of dimethylsulfoxide (1.0 mL) in dichloromethane (9.0 mL) at −78° C., and the mixture was stirred for 0.5 hr at −78° C. A solution of [4-methoxymethyloxy-3-(4-phenoxybenzyl)phenyl]hydroxymethylphosphonic acid diethylester (3.16 g) in dichloromethane (12.0 mL) was added at −78° C., and the mixture was stirred for 0.5 hr at −78° C. Triethylamine (3.0 mL) was added at −78° C., and the cold bath was removed. The reaction mixture was stirred for 0.5 hr. The mixture was poured into ice-water, and dichloromethane layer was separated. The dichloromethane layer was washed with brine, dried over anhydrous sodium sulfate and evaporated. The residue was purified by silica gel column chromatography (ethyl acetate) to give the title compound (3.00 g) as a colorless oil.

$^1$H-NMR (δ) CDCl$_3$; 1.36 (t, 6H, J=7 Hz), 3.34 (s, 3H), 3.99 (s, 2H), 4.20-4.27 (m, 4H), 5.26 (s, 2H), 6.90-7.32 (m, 10H), 8.05 (d, 1H, J=2 Hz), 8.22 (dd, 1H, J=2 Hz, 8 Hz).

(3) [4-Hydroxy-3-(4-phenoxybenzyl)phenyl]benzoyllphosphonic acid (compound 49)

To a solution of [4-methoxymethyloxy-3-(4-phenoxybenzyl)phenyl]benzoyllphosphonic acid diethylester (3.00 g) in dichloromethane (30.0 mL) was added bromotrimethylsilane (3.0 mL) at 0° C., and the reaction mixture was stirred for 18 hr at room temperature. Methanol (4.0 mL) was added to the reaction mixture, and the mixture was stirred for 10 min at room temperature. Evaporation and crystallization from ethyl acetate-n-hexane gave the title compound (1.31 g) as a pale brown crystal.

$^1$H-NMR (δ) CD$_3$OD; 3.90 (s, 2H), 6.87-6.97 (m, 5H), 7.07-7.37 (m, 5H), 7.93 (d, 1H, J=2 Hz), 8.06 (dd, 1H, J=2 Hz, 8 Hz). ESI-MS (m/z); 383 [M−H]$^-$.

Example 44

[3-(4-Ethylbenzyl)-4-hydroxybenzoyl]phosphonic acid (compound 37)

The title compound was synthesized from 3-(4-ethylbenzyl)-4-methoxymethyloxybenzaldehyde as a starting material by the same procedure as described in Example 43.

$^1$H-NMR (δ) CD$_3$OD; 1.16 (t, 3H, J=8 Hz), 2.54 (q, 2H, J=8 Hz), 3.92 (s, 2H), 6.85 (d, 1H, J=8 Hz), 7.05 (d, 2H, J=8 Hz), 7.11 (d, 2H, J=8 Hz), 7.97 (s, 1H), 8.05 (d, 1H, J=2 Hz, 8 Hz). ESI-MS (m/z); 319 [M−H]$^-$.

Example 45

[3-(4-Ethoxybenzyl)-4-hydroxybenzoyl]phosphonic acid (compound 38)

The title compound was synthesized from 3-(4-ethoxybenzyl)-4-methoxymethyloxybenzaldehyde as starting material by the same procedure as described in Example 43.

$^1$H-NMR (δ) CD$_3$OD; 1.32 (t, 3H, J=7 Hz), 3.89 (s, 2H), 3.94 (q, 2H, J=7 Hz), 6.77 (dd, 2H, J=2 Hz, 8 Hz), 6.85 (d, 1H, J=9 Hz), 7.10 (dd, 2H, J=2 Hz, 8 Hz), 7.95 (d, 1H, J=2 Hz), 8.04 (dd, 1H, J=2 Hz, 8 Hz). ESI-MS (m/z); 335 [M−H]$^-$.

Example 46

[3-(4-Ethoxyphenoxy)-4-hydroxybenzoyl]phosphonic acid (compound 39)

The title compound was synthesized from 3-(4-ethoxyphenoxy)-4-methoxymethyloxybenzaldehyde as a starting material by the same procedure as described in Example 43.

$^1$H-NMR (δ) D$_2$O; 1.35 (t, 3H, J=7 Hz), 4.06 (q, 2H, J=7 Hz), 6.95 (d, 2H, J=9 Hz), 6.98 (d, 2H, J=9 Hz), 7.12 (d, 1H, J=8 Hz), 7.66 (d, 1H, J=2 Hz), 8.07 (dd, 1H, J=2 Hz, 8 Hz). ESI-MS (m/z); 337 [M−H]$^-$.

Example 47

[3-[2-(4-Ethoxyphenyl)ethyl]-4-hydroxybenzoyl]phosphonic acid (compound 40)

The title compound was synthesized from 3-[2-(4-ethoxyphenyl)ethyl]-4-methoxymethyloxybenzaldehyde as a starting material by the same procedure as described in Example 43.

$^1$H-NMR (δ) CD$_3$OD; 1.34 (t, 3H, J=7 Hz), 2.75-2.82 (m, 4H), 3.97 (q, 2H, J=7 Hz), 6.81 (d, 2H, J=9 Hz), 6.91 (d, 1H, J=8 Hz), 7.13 (d, 2H, J=9 Hz), 7.95 (d, 1H, J=2 Hz), 8.03 (dd, 1H, J=2 Hz, 8 Hz). ESI-MS (m/z); 349 [M−H]$^-$.

Example 48

[3-(4-Ethoxyphenoxymethyl)-4-hydroxybenzoyl]phosphonic acid (compound 41)

The title compound was synthesized from 3-(4-ethoxyphenoxymethyl-4-methoxymethyloxybenzaldehyde as a starting material by the same procedure as described in Example 43.

$^1$H-NMR (δ) CD$_3$OD; 1.34 (t, 3H, J=7 Hz), 3.95 (q, 2H, J=7 Hz), 5.04 (s, 2H), 6.81 (d, 2H, J=9 Hz), 6.91-6.94 (2d, 3H), 8.16 (d, 1H, J=9 Hz), 8.33 (s, 1H). ESI-MS (m/z); 351 [M−H]$^-$.

Example 49

[4-Hydroxy-3-(4-methylthiobenzyl)benzoyl]phosphonic acid (compound 42)

The title compound was synthesized from 3-(4-methylthiobenzyl)-4-methoxymethyloxybenzaldehyde as a starting material by the same procedure as described in Example 43.

$^1$H-NMR (δ) CD$_3$OD; 2.42 (s, 3H), 3.87 (s, 2H), 6.92 (d, 1H, J=8 Hz), 7.14 (d, 2H, J=9 Hz), 7.17 (d, 2H, J=9 Hz), 7.91 (d, 1H, J=2 Hz), 8.07 (dd, 1H, J=2 Hz, 8 Hz). ESI-MS (m/z); 337 [M−H]$^-$.

Example 50

[4-Hydroxy-3-(4-hydroxybenzyl)benzoyl]phosphonic acid (compound 43)

The title compound was synthesized from 3-(4-methoxymethyloxybenzyl)-4-methoxymethyloxybenzaldehyde as a starting material by the same procedure as described in Example 43.

¹H-NMR (δ) CD₃OD; 3.86 (s, 2H), 6.65 (dd, 2H, J=2 Hz, 9 Hz), 6.85 (d, 1H, J=9 Hz), 7.03 (dd, 2H, J=2 Hz, 8 Hz), 7.94 (d, 1H, J=2 Hz), 8.05 (dd, 1H, J=2 Hz, 9 Hz). ESI-MS (m/z); 307 [M−H]⁻.

Example 51

[4-Hydroxy-3-(4-methoxybenzyl)benzoyl]phosphonic acid (compound 44)

The title compound was synthesized from 3-(4-methoxybenzyl)-4-methoxymethyloxybenzaldehyde as a starting material by the same procedure as described in Example 43.
¹H-NMR (δ) CD₃OD; 3.69 (s, 3H), 3.83 (s, 2H), 6.82 (d, 2H, J=8 Hz), 6.91 (d, 1H, J=9 Hz), 7.11 (d, 2H, J=8 Hz), 7.88 (s, 1H), 8.06 (d, 1H, J=8 Hz). ESI-MS (m/z); 321 [M−H]⁻.

Example 52

[4-Hydroxy-3-(4-n-propoxybenzyl)benzoyl]phosphonic acid (compound 45)

The title compound was synthesized from 3-(4-n-propoxybenzyl)-4-methoxymethyloxybenzaldehyde as a starting material by the same procedure as described in Example 43.
¹H-NMR (δ) CD₃OD; 1.02 (t, 3H, J=7 Hz), 1.72-1.78 (m, 2H), 3.89 (s, 2H), 3.88 (t, 2H, J=7 Hz), 6.78 (d, 2H, J=9 Hz), 6.85 (d, 1H, J=9 Hz), 7.13 (d, 2H, J=9 Hz), 7.95 (d, 1H, J=2 Hz), 8.07 (dd, 1H, J=2 Hz, 9 Hz). ESI-MS (m/z); 349 [M−H]⁻.

Example 53

[4-Hydroxy-3-(4-i-propoxybenzyl)benzoyl]phosphonic acid (compound 46)

The title compound was synthesized from 3-(4-i-propoxybenzyl)-4-methoxymethyloxybenzaldehyde as a starting material by the same procedure as described in Example 43.
¹H-NMR (δ) CD₃OD; 1.26 (d, 6H, J=6 Hz), 3.89 (s, 2H), 4.50-4.53 (m, 1H), 6.77 (d, 2H, J=9 Hz), 6.89 (d, 1H, J=8 Hz), 7.11 (d, 2H, J=9 Hz), 7.96 (d, 1H, J=2 Hz), 8.04 (dd, 1H, J=2 Hz, 8 Hz). ESI-MS (m/z); 349 [M−H]⁻.

Example 54

[4-(2-Hydroxyethoxy)-3-(4-i-propoxybenzyl)benzoyl]phosphonic acid (compound 47)

The title compound was synthesized from 4-(2-methoxymethylethoxy)-3-(4-i-propoxybenzyl)benzaldehyde as a starting material by the same procedure as described in Example 43.
¹H-NMR (δ) DMSO-d₆; 1.21 (d, 6H, J=6 Hz), 3.80 (s, 2H), 4.21 (m, 2H), 4.34 (m, 2H), 4.51 (m, 1H), 6.75-6.77 (m, 2H), 6.91-6.96 (m, 1H), 7.08-7.13 (m, 2H), 7.92 (d, 1H, J=2 Hz), 8.32 (d, 1H, J=8 Hz). ESI-MS (m/z); 393 [M−H]⁻.

Example 55

[3-(4-n-butoxybenzyl)-4-hydroxybenzoyl]phosphonic acid (compound 48)

The title compound was synthesized from 3-(4-n-butoxybenzyl)-4-methoxymethyloxybenzaldehyde as starting material by the same procedure as described in Example 43.
¹H-NMR (δ) CD₃OD; 0.97 (t, 3H, J=7 Hz), 1.45-1.51 (m, 2H), 1.68-1.75 (m, 2H), 3.89 (s, 2H), 3.92 (t, 2H, J=7 Hz), 6.78 (d, 2H, J=9 Hz), 6.86 (d, 1H, J=9 Hz), 7.11 (d, 2H, J=9 Hz), 7.96 (d, 1H, J=2 Hz), 8.06 (dd, 1H, J=2 Hz, 9 Hz). ESI-MS (m/z); 363 [M−H]⁻.

Example 56

[4-(2-Hydroxyethoxy)-3-(4-phenoxybenzyl)benzoyl]phosphonic acid (compound 50)

The title compound was synthesized from 4-(2-methoxymethyloxyethoxy)-3-(4-phenoxybenzyl)benzaldehyde as a starting material by the same procedure as described in Example 43.
¹H-NMR (δ) CD₃OD; 3.84 (s, 2H), 3.88-4.00 (m, 2H), 4.11-4.12 (m, 2H), 6.86-7.00 (m, 4H), 7.00-7.07 (m, 2H), 7.22-7.31 (m, 4H), 7.78 (bs, 1H), 7.87 (d, 1H, J=9 Hz). ESI-MS (m/z); 429 [M+H]⁺.

Example 57

[4-Hydroxy-3-(4-n-octyloxybenzyl)benzoyl]phosphonic acid (compound 51)

The title compound was synthesized from 4-methoxymethyloxy-3-(4-n-octyloxybenzyl)benzaldehyde as a starting material by the same procedure as described in Example 43.
¹H-NMR (δ) CD₃OD; 0.90 (t, 3H, J=7 Hz), 1.30-1.49 (m, 10H), 1.72-1.74 (m, 2H), 3.89-3.93 (m, 4H), 3.92 (t, 2H, J=7 Hz), 6.78 (d, 2H, J=9 Hz), 6.86 (d, 1H, J=8 Hz), 7.12 (d, 2H, J=9 Hz), 7.96 (d, 1H, J=2 Hz), 8.06 (dd, 1H, J=2 Hz, 9 Hz). ESI-MS (m/z); 419 [M−H]⁻.

Example 58

[3-(4-n-Hexyloxybenzyl)-4-hydroxybenzoyl]phosphonic acid (compound 52)

The title compound was synthesized from 3-(4-n-hexyloxybenzyl)-4-(2-methoxymethyloxyethoxy)benzaldehyde as a starting material by the same procedure as described in Example 43.
¹H-NMR (δ) CD₃OD; 0.90-0.93 (t, 3H, J=7 Hz), 1.34-1.36 (m, 4H), 1.44-1.48 (m, 2H), 1.71-1.75 (m, 2H), 3.89 (s, 2H), 3.91 (t, 2H, J=7 Hz), 6.77 (d, 2H, J=9 Hz), 6.85 (d, 1H, J=8 Hz), 7.12 (d, 2H, J=9 Hz), 7.95 (d, 1H, J=2 Hz), 8.07 (dd, 1H, J=2 Hz, 8 Hz). ESI-MS (m/z); 391 [M−H]⁻.

Example 59

[4-Hydroxy-3-[4-(2-hydroxyethoxybenzyl)]benzoyl]phosphonic acid (compound 53)

The title compound was synthesized from 4-methoxymethyloxy-3-[4-(2-methoxymethyloxyethoxybenzyl)]benzaldehyde as a starting material by the same procedure as described in Example 43.
¹H-NMR (δ) CD₃OD; 3.75-3.85 (m, 2H), 3.90 (s, 2H), 4.00 (t, 2H, J=5 Hz), 6.80-6.90 (m, 3H), 7.13 (d, 2H, J=9 Hz), 7.96 (d, 1H, J=2 Hz), 8.06 (d, 1H, J=2 Hz, 9 Hz). ESI-MS (m/z); 351 [M−H]⁻.

Example 60

[3-(Benzo[b]thiophen-2-ylmethyl)-4-hydroxybenzoyl]phosphonic acid (compound 54)

The title compound was synthesized from 3-(benzo[b]thiophen-2-ylmethyl)-4-methoxymethyloxybenzaldehyde as a starting material by the same procedure as described in Example 43.

$^1$H-NMR (δ) CD$_3$OD; 4.24 (s, 2H), 6.92 (d, 1H, J=9 Hz), 7.04 (s, 1H), 7.19-7.26 (m, 2H), 7.63 (d, 1H, J=7 Hz), 7.70 (dd, 1H, J=2 Hz, 7 Hz), 8.10 (dd, 1H, J=2 Hz 7 Hz), 8.12 (d, 1H, J=2 Hz). ESI-MS (m/z); 347 [M−H]$^-$.

Example 61

[3-(Benzo[b]thiophen-2-ylmethyl)-4-(2-hydroxythoxy)benzoyl]phosphonic acid (compound 55)

The title compound was synthesized from 3-(benzo[b]thiophen-2-ylmethyl)-4-(2-methoxymethyloxyethoxy)benzaldehyde as a starting material by the same procedure as described in Example 43.

$^1$H-NMR (δ) CD$_3$OD; 3.82 (m, 2H), 4.00 (s, 2H), 4.19 (m, 2H), 7.05 (s, 1H), 6.83-7.30 (m, 5H), 8.06 (s, 1H), 8.20 (d, 1H, J=8 Hz). ESI-MS (m/z); 391 [M−H]$^-$.

Example 62

[3-(Benzo[1,3]dioxol-5-ylmethyl)-4-hydroxybenzoyl]phosphonic acid (compound 56)

The title compound was synthesized from 3-(benzo[1,3]dioxol-5-ylmethyl)-4-methoxymethyloxybenzaldehyde as a starting material by the same procedure as described in Example 43.

$^1$H-NMR (δ) CD$_3$OD; 3.88 (s, 2H), 5.86 (s, 2H), 6.67-6.71 (m, 3H), 6.87 (d, 1H, J=9 Hz), 7.97 (d, 1H, J=2 Hz), 8.06 (dd, 1H, J=2 Hz, 9 Hz). ESI-MS (m/z); 335 [M−H]$^-$.

Example 63

[3-(4-Ethoxybenzyl)-4-(2-hydroxyethoxy)benzoyl]phosphonic acid (compound 57)

The title compound was synthesized from 3-(4-ethoxybenzyl)-4-(2-methoxymethyloxyethoxy)benzaldehyde as a starting material by the same procedure as described in Example 43.

$^1$H-NMR (δ) CD$_3$OD; 1.34 (t, 3H, J=7 Hz), 3.88 (t, 2H, J=5 Hz), 3.95 (s, 2H), 3.98 (q, 2H, J=7 Hz), 4.14 (t, 2H, J=5 Hz), 6.78 (dd, 2H, J=2 Hz, 8 Hz), 7.05 (d, 1H, J=9 Hz), 7.14 (d, 2H, J=2 Hz, 8 Hz), 7.98 (d, 1H, J=2 Hz), 8.21 (dd, 1H, J=2 Hz, 9 Hz). ESI-MS (m/z); 383 [M−H]$^-$.

Example 64

[3-[4-(2-Ethoxyethoxy)benzyl]-4-hydroxybenzoyl]phosphonic acid (compound 58)

The title compound was synthesized from 3-[4-(2-ethoxyethoxy)benzyl]-4-methoxymethyloxybenzaldehyde as a starting material by the same procedure as described in Example 43.

$^1$H-NMR (δ) CD$_3$OD; 1.20 (t, 3H, J=7 Hz), 3.58 (q, 2H, J=7 Hz), 3.75 (t, 2H, J=5 Hz), 3.90 (s, 2H), 4.06 (t, 2H, J=5 Hz), 6.81-6.87 (m, 3H), 7.13 (d, 2H, J=9 Hz), 7.96 (d, 1H, J=2 Hz), 8.06 (dd, 1H, J=2 Hz, 9 Hz). ESI-MS (m/z); 381 [M+H]$^+$.

Example 65

[4-Hydroxy-3-(4-methylsulfonylbenzyl)benzoyl]phosphonic acid (compound 59)

The title compound was synthesized from 4-methylmethyoxy-3-(4-methylsulfonylbenzyl)benzaldehyde as a starting material by the same procedure as described in Example 43.

$^1$H-NMR (δ) CD$_3$OD; 3.07 (s, 3H), 4.09 (s, 2H), 6.89 (d, 1H, J=8 Hz), 7.49 (d, 2H, J=8 Hz), 7.83 (d, 2H, J=8 Hz), 8.07 (s, 1H), 8.09 (d, 1H, J=8 Hz). ESI-MS (m/z); 369 [M−H]$^-$.

Example 66

[4-(2-Hydroxyethoxy)-3-(4-methylthiobenzyl)benzoyl]phosphonic acid (compound 60)

The title compound was synthesized from 4-(2-methylmethyoxyethoxy)-3-(4-methylthiobenzyl)benzaldehyde as a starting material by the same procedure as described in Example 43.

$^1$H-NMR (δ) CD$_3$OD; 2.44 (s, 3H), 3.93 (t, 2H, J=5 Hz), 3.99 (s, 2H), 4.19 (t, 2H, J=5 Hz), 7.11 (d, 1H, J=9 Hz), 7.17 (d, 2H, J=9 Hz), 7.20 (d, 2H, J=9 Hz), 7.99 (d, 1H, J=2 Hz), 8.22 (dd, 1H, J=2 Hz, 9 Hz). ESI-MS (m/z); 381 [M−H]$^-$.

Example 67

[3-(4-Ethylthiobenzyl)-4-hydroxybenzoyl]phosphonic acid (compound 61)

The title compound was synthesized from 3-(4-ethylthiobenzyl)-4-methoxymethyloxybenzaldehyde as a starting material by the same procedure as described in Example 43.

$^1$H-NMR (δ) CD$_3$OD; 1.23 (t, 3H, J=7 Hz), 2.87 (q, 2H, J=7 Hz), 3.93 (s, 2H), 6.87 (d, 1H, J=9 Hz), 7.16 (d, 2H, J=8 Hz), 7.22 (d, 2H, J=8 Hz), 7.99 (d, 1H, J=2 Hz), 8.06 (dd, 1H, J=2 Hz, 8 Hz). ESI-MS (m/z); 35 1[M−H]$^-$.

Example 68

[3-(4-Ethylthiobenzyl)-4-(2-hydroxyethoxy)benzoyl]phosphonic acid (compound 62)

The title compound was synthesized from 3-(4-ethylthiobenzyl)-4-(2-methoxymethyloxyethoxy)benzaldehyde as starting material by the same procedure as described in Example 43.

$^1$H-NMR (δ) CD$_3$OD; 1.22 (t, 3H, J=7 Hz), 2.86 (q, 2H, J=7 Hz), 3.84 (t, 2H, J=5 Hz), 3.98 (s, 2H), 4.08 (t, 2H, J=5 Hz), 6.96 (d, 1H, J=8 Hz), 7.18 (m, 4H), 8.15 (s, 1H), 8.51 (d, 1H, J=8 Hz). ESI-MS (m/z); 395 [M−H]$^-$.

Example 69

[3-(4-Ethylsulfonylbenzyl)-4-hydroxybenzoyl]phosphonic acid (compound 63)

The title compound was synthesized from 3-(4-ethylsulfonylbenzyl)-4-methoxymethyloxybenzaldehyde as a starting material by the same procedure as described in Example 43.

¹H-NMR (δ) DMSO-d₆; 1.06 (t, 3H, J=7 Hz), 3.20 (q, 2H, J=7 Hz), 3.98 (s, 2H), 6.90 (d, 1H, J=8 Hz), 7.45 (d, 2H, J=8 Hz), 7.74 (d, 2H, J=8 Hz), 7.96 (s, 1H), 8.14 (d, 1H, J=8 Hz). ESI-MS (m/z); 383 [M−H]⁻.

Example 70

[5-(4-Ethoxybenzyl)thiophen-2-carbonyl]phosphonic acid (compound 70)

(1)
[5-(4-Ethoxybenzyl)thiophen-2-carbonyl]phosphonic acid diethylester

Triethyl phosphite (1.3 mL) was added to 5-(4-ethoxybenzyl)thiophen-2-carbonylchloride (1.10 g), and the mixture was stirred for 22 hr at room temperature. After evaporation, the residue was purified by silica gel column chromatography (ethyl acetate/n-hexane=2/1) to give the title compound (0.54 g) as a pale yellow oil.

¹H-NMR (δ) CDCl₃; 1.34-1.42 (m, 9H), 4.00 (q, 2H, J=7 Hz), 4.11 (s, 2H), 4.25-4.28 (m, 4H), 6.83 (dd, 2H, J=2 Hz, 8 Hz), 6.88 (d, 1H, J=4 Hz), 7.13 (dd, 2H, J=2 Hz, 8 Hz), 8.27 (d, 1H, J=4 Hz).

MS (m/z); 382 (M)⁺, 245 (Base peak), 217, 189, 160, 128, 107, 84.

(2)
[5-(4-Ethoxybenzyl)thiophen-2-carbonyl]phosphonic acid (compound 70)

To a solution of [5-(4-ethoxybenzyl)thiophen-2-carbonyl]phosphonic acid diethylester (0.54 g) in dichloromethane (14.0 mL) was added bromotrimethylsilane (0.9 mL) at 0° C., and the reaction mixture was stirred for 22 hr at room temperature. Methanol (1.0 mL) was added to the reaction mixture, and the mixture was stirred for 10 min at room temperature. After evaporation, the residue was crystallized from ethyl acetate to give the title compound (0.15 g) as a colorless crystal.

¹H-NMR (δ) CD₃OD; 1.36 (t, 3H, J=7 Hz), 3.99 (q, 2H, J=7 Hz), 4.14 (s, 2H), 6.84 (dd, 2H, J=2 Hz, 9 Hz), 6.97 (d, 1H, J=4 Hz), 7.16 (dd, 2H, J=2 Hz, 9 Hz), 8.16 (d, 1H, J=4 Hz). ESI-MS (m/z); 325 [M−H]⁻.

Example 71

[5-(4-Ethoxybenzyl)-3-methylthiophen-2-carbonyl] phosphonic acid (compound 71)

The title compound was synthesized from 5-(4-ethoxybenzyl)-3-methylthiophen-2-carbonylchloride as a starting material by the same procedure as described in Example 70.

¹H-NMR (δ) CD₃OD; 1.36 (t, 3H, J=7 Hz), 2.50 (s, 3H), 3.99 (q, 2H, J=7 Hz), 4.09 (s, 2H), 6.81-6.85 (m, 3H), 7.16 (d, 2H, J=8 Hz). ESI-MS (m/z); 339 [M−H]⁻.

Example 72

[5-(4-Ethoxybenzyl)thiophen-3-carbonyl]phosphonic acid (compound 72)

The title compound was synthesized from 5-(4-ethoxybenzyl)thiophen-3-carbonylchloride as a starting material by the same procedure as described in Example 70.

¹H-NMR (δ) CD₃OD; 1.36 (t, 3H, J=7 Hz), 3.99 (q, 2H, J=7 Hz), 4.08 (s, 2H), 6.83 (dd, 2H, J=2 Hz, 8 Hz), 7.14 (dd, 2H, J=2 Hz, 8 Hz), 7.31 (s, 1H), 8.56 (s, 1H). ESI-MS (m/z); 325 [M−H]⁻.

Example 73

[5-(4-Methylthiobenzyl)thiophen-2-carbonyl]phosphonic acid (compound 73)

The title compound was synthesized from 5-(4-methylthiobenzyl)thiophen-2-carbonylchloride as a starting material by the same procedure as described in Example 70.

¹H-NMR (δ) CD₃OD; 2.45 (s, 3H), 4.17 (s, 2H), 6.99 (d, 1H, J=4 Hz), 7.18 (dd, 2H, J=2 Hz, 8 Hz), 7.23 (dd, 2H, J=2 Hz, 8 Hz), 8.17 (d, 1H, J=4 Hz). ESI-MS (m/z); 327 [M−H]⁻.

Example 74

[5-(4-Methylsulfonylbenzyl)thiophen-2-carbonyl] phosphonic acid (compound 74)

The title compound was synthesized from 5-(4-methylsulfonylbenzyl)thiophen-2-carbonylchloride as a starting material by the same procedure as described in Example 70.

¹H-NMR (δ) CD₃OD; 3.18 (s, 3H), 4.29 (s, 2H), 6.97 (d, 1H, J=4 Hz), 7.54 (d, 2H, J=8 Hz), 7.86 (d, 2H, J=8 Hz), 8.19 (d, 1H, J=4 Hz). ESI-MS (m/z); 359 [M−H]⁻.

Example 75

[5-(4-Chlorobenzyl)thiophen-2-carbonyl]phosphonic acid (compound 75)

The title compound was synthesized from 5-(4-chlorobenzyl)thiophen-2-carbonylchloride as a starting material by the same procedure as described in Example 70.

¹H-NMR (δ) CD₃OD; 4.17 (s, 2H), 6.92 (d, 1H, J=4 Hz), 7.24 (dd, 2H, J=2 Hz, 8 Hz), 7.29 (dd, 2H, J=2 Hz, 8 Hz), 8.29 (d, 1H, J=4 Hz). ESI-MS (m/z); 315 [M−H]⁻.

Example 76

[5-(4-Ethylthiobenzyl)thiophen-2-carbonyl]phosphonic acid (compound 76)

The title compound was synthesized from 5-(4-ethylthiobenzyl)thiophen-2-carbonylchloride as a starting material by the same procedure as described in Example 70.

¹H-NMR (δ) CD₃OD; 1.27 (t, 3H, J=8 Hz), 2.92 (q, 2H, J=8 Hz), 4.19 (s, 2H), 7.01 (d, 1H, J=4 Hz), 7.21 (dd, 2H, J=2 Hz, 6 Hz), 7.29 (dd, 2H, J=2 Hz 6 Hz), 8.18 (d, 1H, J=4 Hz). ESI-MS (m/z); 341 [M−H]⁻.

Example 77

[5-(4-Phenoxybenzyl)thiophen-2-carbonyl]phosphonic acid (compound 77)

The title compound was synthesized from 5-(4-phenoxybenzyl)thiophen-2-carbonylchloride as a starting material by the same procedure as described in Example 70.

¹H-NMR (δ) CD₃OD; 4.21 (s, 2H), 6.92-6.98 (m, 4H), 7.03 (d, 1H, J=4 Hz), 7.09 (t, 1H, J=8 Hz), 7.24-7.35 (m, 4H), 8.19 (d, 1H, J=4 Hz). ESI-MS (m/z); 373 [M−H]⁻.

Example 78

[5-(4-Benzyloxybenzyl)thiophen-2-carbonyl]phosphonic acid (compound 78)

The title compound was synthesized from 5-(4-benzyloxybenzyl)thiophen-2-carbonylchloride as a starting material by the same procedure as described in Example 70.

$^1$H-NMR (δ) CD$_3$OD; 4.14 (s, 2H), 5.05 (s, 2H), 6.94 (d, 2H, J=9 Hz), 6.97 (d, 1H, J=4 Hz), 7.17 (d, 2H, J=9 Hz), 7.27-7.42 (m, 5H), 8.18 (d, 1H, J=4 Hz). ESI-MS (m/z); 387 [M−H]$^−$.

Example 79

[5-(4-i-Propoxybenzyl)thiophen-2-carbonyl]phosphonic acid (compound 79)

The title compound was synthesized from 5-(4-i-propoxybenzyl)thiophen-2-carbonylchloride as a starting material by the same procedure as described in Example 70.

$^1$H-NMR (δ) DMSO-d$_6$; 1.23 (d, 6H, J=6 Hz), 4.07 (s, 2H), 4.52-4.58 (m, 1H), 6.84 (d, 2H, J=9 Hz), 6.91 (d, 1H, J=4 Hz), 7.16 (d, 2H, J=9 Hz), 8.17 (d, 1H, J=4 Hz). ESI-MS (m/z); 339 [M−H]$^−$.

Example 80

[5-(4-n-Butoxybenzyl)thiophen-2-carbonyl]phosphonic acid (compound 80)

The title compound was synthesized from 5-(4-n-butoxybenzyl)thiophen-2-carbonylchloride as a starting material by the same procedure as described in Example 70.

$^1$H-NMR (δ) CD$_3$OD; 0.98 (t, 3H, J=7 Hz), 1.48-1.52 (m, 2H), 1.72-1.75 (m, 2H), 3.95 (t, 2H, J=7 Hz), 4.15 (s, 2H), 6.68 (d, 2H, J=9 Hz), 6.99 (d, 1H, J=4 Hz), 7.16 (d, 2H, J=9 Hz), 8.18 (d, 1H, J=4 Hz). ESI-MS (m/z); 353 [M−H]$^−$.

Example 81

[5-(4-n-Pentyloxybenzyl)thiophen-2-carbonyl]phosphonic acid (compound 81)

The title compound was synthesized from 5-(4-n-pentyloxybenzyl)thiophen-2-carbonylchloride as a starting material by the same procedure as described in Example 70.

$^1$H-NMR (δ) CD$_3$OD; 0.94 (t, 3H, J=7 Hz), 1.34-1.49 (m, 4H), 1.75-1.78 (m, 2H), 3.94 (t, 2H, J=7 Hz), 4.14 (s, 2H), 6.85 (d, 2H, J=9 Hz), 6.98 (d, 1H, J=4 Hz), 7.16 (d, 2H, J=9 Hz), 8.17 (d, 1H, J=4 Hz). ESI-MS (m/z); 367 [M−H]$^−$.

Example 82

[5-(4-n-Octyloxybenzyl)thiophen-2-carbonyl]phosphonic acid (compound 82)

The title compound was synthesized from 5-(4-n-octyloxybenzyl)thiophen-2-carbonylchloride as a starting material by the same procedure as described in Example 70.

$^1$H-NMR (δ) CD$_3$OD; 0.90 (t, 3H, J=7 Hz), 1.31-1.48 (m, 10H), 1.74-1.75 (m, 2H), 3.94 (t, 2H, J=7 Hz), 4.14 (s, 2H), 6.85 (d, 2H, J=9 Hz), 6.98 (d, 1H, J=4 Hz), 7.16 (d, 2H, J=9 Hz), 8.18 (d, 1H, J=4 Hz). ESI-MS (m/z); 411 [M+H]$^+$.

Example 83

[5-(4-n-Tridecanyloxybenzyl)thiophen-2-carbonyl]phosphonic acid (compound 83)

The title compound was synthesized from 5-(4-n-tridecanyloxybenzyl)thiophen-2-carbonylchloride as a starting material by the same procedure as described in Example 70.

$^1$H-NMR (δ) CD$_3$OD; 0.89 (t, 3H, J=7 Hz), 1.28-1.38 (m, 18H), 1.44-1.46 (m, 2H), 1.74-1.76 (m, 2H), 3.94 (t, 2H, J=7 Hz), 4.14 (s, 2H), 6.85 (d, 2H, J=9 Hz), 6.98 (d, 1H, J=4 Hz), 7.16 (d, 2H, J=9 Hz), 8.17 (d, 1H, J=4 Hz). ESI-MS (m/z); 479 [M−H]$^−$.

Example 84

[5-(4-(2-Ethoxyethoxybenzyl)thiophen-2-carbonyl)phosphonic acid (compound 84)

The title compound was synthesized from 5-[4-(2-ethoxyethoxybenzyl)]thiophen-2-carbonylchloride as a starting material by the same procedure as described in Example 70.

$^1$H-NMR (δ) CD$_3$OD; 1.62 (t, 3H, J=7 Hz), 3.54 (q, 2H, J=7 Hz), 3.72 (t, 2H, J=5 Hz), 4.04 (t, 2H, J=5 Hz), 4.08 (s, 2H), 6.84 (d, 2H, J=9 Hz), 6.89 (d, 1H, J=4 Hz), 7.12 (d, 2H, J=9 Hz), 8.19 (d, 1H, J=4 Hz). ESI-MS (m/z); 369 [M−H]$^−$.

Example 85

[4-(5-Phosphonocarbonylthiophen-2-ylmethyl)]phenoxyacetic acid (compound 85)

The title compound was synthesized from [5-(4-t-butoxycarbonylmethoxybenzyl)]thiophen-2-carbonylchloride as a starting material by the same procedure as described in Example 70.

$^1$H-NMR (δ) DMSO-d$_6$; 4.08 (s, 2H), 4.06 (s, 2H), 6.83 (d, 2H, J=9 Hz), 6.88 (d, 1H, J=4 Hz), 7.16 (d, 2H, J=9 Hz), 8.16 (d, 1H, J=4 Hz). ESI-MS (m/z); 355 [M−H]$^−$.

Example 86

[5-(4-Carbamoylmethoxybenzyl)]thiophen-2-carbonyl]phosphonic acid (compound 86)

The title compound was synthesized from [5-(4-carbamoylmethoxybenzyl)]thiophen-2-carbonylchloride as a starting material by the same procedure as described in Example 70.

$^1$H-NMR (δ) CD$_3$OD; 4.17 (s, 2H), 4.39 (s, 2H), 6.93 (d, 2H, J=9 Hz), 6.99 (d, 1H, J=4 Hz), 7.21 (d, 2H, J=9 Hz), 8.16 (d, 1H, J=4 Hz). ESI-MS (m/z); 354 [M−H]$^−$.

Example 87

{5-[4-(2-Morpholin-4-ylethoxy)benzyl]thiophen-2-carbonyl}phosphonic acid (compound 81)

The title compound was synthesized from 5-[4-(2-morpholin-4-ylethoxy)benzyl]thiophen-2-carbonylchloride hydrochloride as a starting material by the same procedure as described in Example 70.

$^1$H-NMR (δ) D$_2$O; 3.20-3.55 (m, 2H), 3.55-3.70 (m, 4H), 3.70-3.90 (m, 2H), 4.00-4.15 (m, 2H), 4.11 (s, 2H), 4.34 (m,

2H), 6.94 (d, 2H, J=8 Hz), 7.00 (d, 1H, J=4 Hz), 7.23 (d, 2H, J=8 Hz), 8.13 (d, 1H, J=4 Hz). ESI-MS (m/z); 410 [M–H]⁻.

Example 88

[5-(Benzo[b]thiophen-2-ylmethyl)thiophen-2-carbonyl]phosphonic acid (compound 88)

The title compound was synthesized from [5-(benzo[b]thiophen-2-ylmethyl)thiophen-2-carbonylchloride as a starting material by the same procedure as described in Example 70.

¹H-NM (δ) DMSO-$d_6$; 4.50 (s, 2H), 7.03 (d, 1H, J=4 Hz), 7.27-7.33 (m, 3H), 7.77 (d, 1H, J=7 Hz), 7.87 (d, 1H, J=7 Hz), 8.21 (d, 1H, J=4 Hz). ESI-MS (m/z); 337 [M–H]⁻.

Example 89

[5-(4-Ethylbenzyl)benzo[b]thiophen-2-phosphonic acid (compound 89)

(1) [5-(4-Ethylbenzyl)benzo[b]thiophen-2-phosphonic acid diethylester

To a solution of 5-(4-ethylbenzyl)benzo[b]thiophene (1.50 g) in THF (11.8 mL) was added 2.44 M n-butyllithium/n-hexane solution (2.9 mL) at –78° C., and the reaction mixture was stirred for 1 hr at same temperature. Diethyl chlorophosphate (0.9 mL) was added to the reaction mixture at –78° C., and the reaction mixture was stirred for 0.5 hr at –78° C. The reaction was quenched by the addition of saturated aqueous ammonium chloride and extracted with ethyl acetate. The combined ethyl acetate extracts were washed with brine, dried over anhydrous sodium sulfate and evaporated. The residue was purified by silica gel column chromatography (ethyl acetate/n-hexane=1/2) to give the title compound (1.79 g) as a colorless oil.

¹H-NMR (δ) CDCl₃; 1.22 (t, 3H, J=8 Hz), 1.35 (t, 6H, J=7 Hz), 2.61 (q, 2H, J=8 Hz), 4.07 (s, 2H), 4.08-4.21 (m, 4H), 7.10-7.20 (m, 4H), 7.29 (d, 1H, J=8 Hz), 7.69 (s, 1H), 7.78 (d, 1H, J=8 Hz), 7.85 (d, 1H, J=9 Hz). MS (m/z); 388 (M⁺), 359, 331, 303, 279, 252, 221, 189, 165, 119.

(2) [5-(4-Ethylbenzyl)benzo[b]thiophen-2-phosphonic acid (compound 89)

To a solution of [5-(4-ethylbenzyl)benzo[b]thiophen-2-phosphonic acid diethylester (1.00 g) in dichloromethane (17.0 mL) was added bromotrimethylsilane (1.7 mL) at 0° C., and the reaction mixture was stirred for 19 hr at room temperature. Methanol (4.5 mL) was added to the reaction mixture, and the mixture was stirred for 10 min at room temperature. After evaporation, the residue was crystallized from ethyl acetate-n-hexane to give the title compound (0.72 g) as a colorless crystal.

¹H-NMR (δ) CD₃OD; 1.19 (t, 3H, J=8 Hz), 2.58 (q, 2H, J=8 Hz), 4.03 (s, 2H), 7.08-7.12 (m, 4H), 7.26 (d, 1H, J=9 Hz), 7.70 (s, 1H), 7.76 (d, 1H, J=27 Hz), 7.77 (d, 1H, J=9 Hz). ESI-MS (m/z); 331 [M–H]⁻.

Example 90

[5-(4-Ethylbenzyl)benzo[b]thiophen-2-ylmethyl]phosphonic acid (compound 90)

(1) [5-(4-Ethylbenzyl)benzo[b]thiophen-2-ylmethyl]phosphonic acid diethylester

Triethyl phosphite (1.3 mL) was added to 1-chloromethyl-5-(4-ethylbenzyl)benzo[b]thiophene (1.23 g), and the mixture was stirred for 16 hr at 150° C. The mixture was purified by silica gel column chromatography (ethyl acetate/n-hexane=2/1) to give the title compound (1.51 g) as a pale yellow oil.

¹H-NMR (δ) CDCl₃; 1.29-1.70 (m, 9H), 2.61 (q, 2H, J=8 Hz), 3.41 (d, 2H, J=21 Hz), 4.03 (s, 2H), 4.05-4.15 (m, 4H), 7.11-7.14 (m, 6H), 7.50 (s, 1H), 7.65 (d, 1H, J=8 Hz). MS (m/z); 402 (M⁺), 373, 345, 292, 265, 235, 202, 160, 109, 81 (base peak).

(2) [5-(4-Ethylbenzyl)benzo[b]thiophen-2-ylmethyl]phosphonic acid (compound 90)

To a solution of [5-(4-ethylbenzyl)benzo[b]thiophen-2-ylmethyl]phosphonic acid diethylester (0.80 g) in ethanol (8.0 mL) was added 6N—HCl (8.0 mL), and the reaction mixture was refluxed for 42 hr. Evaporation and crystallization from ethyl acetate-n-hexane gave the title compound (0.54 g) as a colorless crystal.

¹H-NMR (δ) CD₃OD; 1.19 (t, 3H, J=8 Hz), 2.58 (q, 2H, J=8 Hz), 3.38 (d, 2H, J=21 Hz), 4.00 (s, 2H), 7.08-7.12 (m, 5H), 7.15 (d, 1H, J=4 Hz), 7.50 (s, 1H), 7.65 (d, 1H, J=8 Hz). ESI-MS (m/z); 345 [M–H]⁻.

Example 91

[4-(4-Methylthiobenzyl)thiazole-2-carbonyl]phosphonic acid (compound 91)

The title compound was synthesized from 4-(4-methylthiobenzyl)thiazole-2-carbonylchloride as a starting material by the same procedure as described in Example 70.

¹H-NMR (δ) CD₃OD; 2.47 (s, 3H), 4.33 (s, 2H), 7.21 (s, 4H), 8.06 (s, 1H). ESI-MS (m/z); 328 [M–H]⁻.

Example 92

[3-(5-Ethylthiophen-2-ylmethyl)-4-hydroxybenzoyl]phosphonic acid (compound 92)

The title compound was synthesized from 3-(5-ethylthiophen-2-ylmethyl)-4-methoxymethyloxybenzaldehyde as a starting material by the same procedure as described in Example 43.

¹H-NMR (δ) CD₃OD; 1.23 (t, 3H, J=8 Hz), 2.75 (q, 2H, J=8 Hz), 4.06 (s, 2H), 6.54 (d, 1H, J=4 Hz), 6.59 (d, 1H, J=4 Hz), 6.87 (d, 1H, J=8 Hz), 8.02 (d, 1H, J=2 Hz), 8.09 (dd, 1H, J=2 Hz, 8 Hz). ESI-MS (m/z); 325 [M–H]⁻.

Example 93

[4-(2-Methoxyethoxy)-3-(4-phenoxybenzyl)benzoyl]phosphonic acid (compound 93)

The title compound was synthesized from 4-(2-methoxyethoxy)-3-(4-phenoxybenzyl)benzaldehyde as a starting material by the same procedure as described in Example 43.

¹H-NMR (δ) CD₃OD; 3.38 (s, 3H), 3.72 (m, 2H), 3.97 (s, 2H), 4.17 (m, 2H), 6.83-7.05 (m, 6H), 7.22-7.30 (m, 4H), 8.10 (s, 1H), 8.29 (d, 1H, J=8 Hz). ESI-MS (m/z); 441 [M−H]⁻.

Example 94

[2-(4-Phenoxybenzyl)-4-phosphonocarbonylphenoxy]acetic acid methylester (compound 94)

The title compound was synthesized from 4-formyl-3-(4-phenoxybenzyl)phenoxyacetic acid methylester as a starting material by the same procedure as described in Example 43.

¹H-NMR (δ) CD₃OD; 3.34 (s, 3H), 4.08 (s, 2H), 4.45 (s, 2H), 6.81-6.92 (m, 5H), 7.02-7.04 (m, 1H), 7.26-7.31 (m, 4H), 8.14 (d, 1H, J=2 Hz), 8.48 (dd, 1H, J=2 Hz, 8 Hz). ESI-MS (m/z); 455 [M−H]⁻.

Example 95

[2-(4-Phenoxybenzyl)-4-phosphonocarbonylphenoxy]acetic acid (compound 95)

The title compound was synthesized from 4-formyl-3-(4-phenoxybenzyl)phenoxyacetic acid t-butylester as a starting material by the same procedure as described in Example 43.

¹H-NMR (δ) DMSO-d₆; 3.95 (s, 2H), 4.75 (s, 2H), 6.84-6.89 (m, 3H), 6.96 (d, 2H, J=7 Hz), 7.08 (t, 1H, J=7 Hz), 7.28-7.36 (m, 4H), 7.88 (d, 1H, J=2 Hz), 8.32 (dd, 1H, J=2 Hz, 8 Hz). ESI-MS (m/z); 441 [M−H]⁻.

Example 96

[4-Carbamoylmethoxy-3-(4-phenoxybenzyl)benzoyl]phosphonic acid (compound 96)

The title compound was synthesized from 4-carbamoylmethoxy-3-(4-phenoxybenzyl)benzaldehyde as a starting material by the same procedure as described in Example 43.

¹H-NMR (δ) CD₃OD; 4.10 (s, 2H), 4.61 (s, 2H), 6.88-7.33 (m, 10H), 8.10 (d, 1H, J=2 Hz), 8.25 (dd, 1H, J=2 Hz, 9 Hz). ESI-MS (m/z); 440 [M−H]⁻.

Example 97

[4-(2-Aminoethoxy)-3-(4-phenoxybenzyl)benzoyl]phosphonic acid (compound 97)

The title compound was synthesized from 4-(2-t-butoxycarbonylaminoethoxy)-3-(4-phenoxybenzyl)benzaldehyde as a starting material by the same procedure as described in Example 43.

¹H-NMR (δ) CD₃OD; 3.39 (t, 2H, J=5 Hz), 4.07 (s, 2H), 4.32 (t, 2H, J=5 Hz), 6.90-6.96 (m, 4H), 7.07-7.10 (m, 2H), 7.18-7.21 (m, 2H), 7.30-7.34 (m, 2H), 7.77 (dd, 1H, J=2 Hz, 3 Hz), 7.92 (dt, 1H, J=2 Hz, 9 Hz). ESI-MS (m/z); 426 [M−H]⁻.

Example 98

[3-(4-Ethoxybenzyl)-4-(4-hydroxybutoxy)benzoyl]phosphonic acid (compound 98)

The title compound was synthesized from 3-(4-ethoxybenzyl)-3-(4-methoxymethyloxybutoxy)benzaldehyde as a starting material by the same procedure as described in Example 43.

¹H-NMR (δ) CD₃OD; 1.34 (t, 3H, J=7 Hz), 1.60-1.65 (m, 2H), 1.79-1.89 (m, 2H), 3.57 (t, 2H, J=5 Hz), 3.84 (s, 2H), 3.97 (q, 2H, J=5 Hz), 4.19 (t, 2H, J=5 Hz), 6.73 (d, 2H, J=8 Hz), 6.94 (d, 1H, J=8 Hz), 7.07 (d, 2H, J=8 Hz), 8.10 (s, 1H), 8.50 (d, 1H, J=8 Hz). ESI-MS (m/z); 407 [M−H]⁻.

Example 99

[3-(4-Ethoxybenzyl)-4-(6-hydroxyhexyloxy)benzoyl]phosphonic acid (compound 99)

The title compound was synthesized from 3-(4-ethoxybenzyl)-3-(6-methoxymethyloxyhexyloxy)benzaldehyde as a starting material by the same procedure as described in Example 43.

¹H-NMR (δ) CD₃OD; 1.25 (t, 3H, J=7 Hz), 1.30-1.50 (m, 4H), 1.51-1.54 (m, 2H), 1.72-1.88 (m, 2H), 3.53 (t, 2H, J=5 Hz), 3.87 (s, 2H), 3.98 (q, 2H, J=5 Hz), 4.10 (t, 2H, J=5 Hz), 6.73 (d, 2H, J=8 Hz), 6.93 (d, 1H, J=8 Hz), 7.06 (d, 2H, J=8 Hz), 8.11 (s, 1H), 8.49 (d, 1H, J=8 Hz). ESI-MS (m/z); 435 [M−H]⁻.

Example 100

[4-Hydroxy-3-[4-(3-phenyl)phenoxybenzyl]benzoyl]phosphonic acid (compound 101)

The title compound was synthesized from 4-methoxymethyloxy-3-[4-(3-phenyl)phenoxybenzyl]benzaldehyde as a starting material by the same procedure as described in Example 43.

¹H-NMR (δ) CD₃OD; 3.96 (s, 2H), 6.88-6.92 (m, 4H), 7.17-7.39 (m, 8H), 7.51-7.53 (m, 2H), 8.02 (d, 1H, J=2 Hz), 8.08 (dd, 1H, J=2 Hz, 8 Hz). ESI-MS (m/z); 459 [M−H]⁻.

Example 101

[4-Hydroxy-3-[4-(4-phenyl)phenoxybenzyl]benzoyl]phosphonic acid (compound 102)

The title compound was synthesized from 4-methoxymethyloxy-3-[4-(4-phenyl)phenoxybenzyl]benzaldehyde as a starting material by the same procedure as described in Example 43.

¹H-NMR (δ) CD₃OD; 3.97 (s, 2H), 6.88-6.94 (m, 3H), 6.99-7.02 (m, 2H), 7.23-7.29 (m, 3H), 7.36-7.40 (m, 2H), 7.53-7.56 (m, 4H), 8.03 (d, 1H, J=2 Hz), 8.08 (dd, 1H, J=2 Hz, 9 Hz). ESI-MS (m/z); 459 [M−H]⁻.

Example 102

[4-(2-Methoxyethoxy)-3-[4-(3-phenyl)phenoxybenzyl]benzoyl]phosphonic acid (compound 103)

The title compound was synthesized from 4-(2-methoxyethoxy)-3-[4-(3-phenyl)phenoxybenzyl]benzaldehyde as a starting material by the same procedure as described in Example 43.

¹H-NMR (δ) CD₃OD; 3.28 (s, 3H), 3.48-3.52 (m, 2H), 3.78 (s, 2H), 3.80-3.82 (m, 2H), 6.53 (d, 1H, J=9 Hz), 6.82 (d, 1H, J=8 Hz), 7.08 (d, 2H, J=9 Hz), 7.15 (s, 1H), 7.20-7.35 (m, 5H), 7.47 (d, 2H, J=7 Hz), 7.92 (s, 1H), 8.22 (d, 1H, J=8 Hz). ESI-MS (m/z); 517 [M−H]⁻.

Example 103

[4-(2-Hydroxyethoxy)-3-[4-(3-phenyl)phenoxybenzyl]benzoyl]phosphonic acid (compound 104)

The title compound was synthesized from 4-(2-methoxyethyloxyethoxy)-3-[4-(3-phenyl)phenoxybenzyl]benzaldehyde as a starting material by the same procedure as described in Example 43.

$^1$H-NMR (δ) CD$_3$OD; 3.83 (t, 2H, J=5 Hz), 3.95 (s, 2H), 4.01 (t, 2H, J=5 Hz), 6.78 (d, 1H, J=9 Hz), 6.91 (d, 3H, J=9 Hz), 7.01-7.19 (m, 3H), 7.30-7.41 (m, 5H), 7.50-7.54 (m, 2H), 8.04 (s, 1H), 8.34 (d, 1H, J=8 Hz). ESI-MS (m/z); 503 [M−H]$^-$.

Example 104

[4-Carbamoylmethoxy-3-[4-(3-phenyl)phenoxybenzyl]benzoyl]phosphonic acid (compound 105)

The title compound was synthesized from 4-carbamoylmethoxy-3-[4-(3-phenyl)phenoxybenzyl]benzaldehyde as a starting material by the same procedure as described in Example 43.

$^1$H-NMR (δ) DMSO-d$_6$; 3.34 (bs, 4H), 4.05 (s, 2H), 4.61 (s, 2H), 6.95-7.08 (m, 5H), 7.27-7.47 (m, 7H), 7.63 (d, 2H, J=7 Hz), 7.91 (d, 1H, J=2 Hz), 8.23 (dd, 1H, J=2 Hz, 8 Hz). ESI-MS (m/z); 516 [M−H]$^-$.

Example 105

[4-(2-Hydroxyethoxy)-3-(4-n-octyloxylbenzyl)]benzoyl]phosphonic acid (compound 106)

The title compound was synthesized from 4-(2-methoxyethyloxyethoxy)-3-(4-n-octyloxybenzyl)benzaldehyde as a starting material by the same procedure as described in Example 43.

$^1$H-NMR (δ) CD$_3$OD; 0.88 (t, 3H, J=7 Hz), 1.30-1.46 (m, 10H), 1.69-1.74 (m, 2H), 3.87-3.91 (m, 4H), 3.95 (s, 2H), 4.14 (t, 2H, J=5 Hz), 6.77-6.79 (m, 2H), 7.06 (d, 1H, J=9 Hz), 7.12 (dd, 2H, J=2 Hz, 9 Hz), 7.99 (d, 1H, J=2 Hz), 8.22 (dd, 1H, J=2 Hz, 9 Hz). ESI-MS (m/z); 463 [M−H]$^-$.

Example 106

[4-[(2-Hydroxyethylcarbamoyl)methoxy]-3-(4-n-octyloxylbenzyl)]benzoyl]phosphonic acid (compound 107)

The title compound was synthesized from 2-{4-formyl-4-n-octyloxybenzyl}phenoxy]-N-methoxymethoxymethylamide as a starting material by the same procedure as described in Example 43.

$^1$H-NMR (δ) DMSO-d$_6$; 0.90 (t, 3H, J=7 Hz), 1.25-1.45 (m, 10H), 1.70-1.77 (m, 2H), 3.27-3.41 (m, 8H), 3.54 (t, 2H, J=6 Hz), 3.91 (t, 2H, J=7 Hz), 4.03 (s, 2H), 4.55 (s, 2H), 6.80 (d, 2H, J=9 Hz), 6.97 (d, 1H, J=9 Hz), 7.12 (d, 2H, J=9 Hz), 8.17 (s, 1H), 8.35 (d, 1H, J=7 Hz). ESI-MS (m/z); 520 [M−H]$^-$.

Example 107

[4-Carbamoylmethoxy-3-(4-n-octyloxylbenzyl)]benzoyl]phosphonic acid (compound 108)

The title compound was synthesized from 4-carbamoylmethoxy-3-(4-n-octyloxybenzyl)benzaldehyde as a starting material by the same procedure as described in Example 43.

$^1$H-NMR (δ) DMSO-d$_6$; 0.85 (t, 3H, J=7 Hz), 1.25-1.38 (m, 10H), 1.65-1.75 (m, 2H), 3.89 (t, 2H, J=7 Hz), 3.96 (s, 2H), 4.58 (s, 2H), 6.81 (d, 2H, J=9 Hz), 7.04 (d, 1H, J=9 Hz), 7.11 (d, 1H, J=9 Hz), 7.28 (bs, 1H), 7.85 (d, 1H, J=2 Hz), 8.20 (dd, 1H, J=2 Hz, 9 Hz). ESI-MS (m/z); 476 [M−H]$^-$.

Example 108

[4-[-[(1-Carbamoyl-1-methylethylcarbamoyl)methoxy]-3-(4-n-octyloxylbenzyl)]benzoyl]phosphonic acid (compound 109)

The title compound was synthesized from 4-[-[(1-carbamoyl-1-methylethylcarbamoyl)methoxy]-3-(4-n-octyloxybenzyl)-benzaldehyde as a starting material by the same procedure as described in Example 43.

$^1$H-NMR (δ) CD$_3$OD; 0.89 (t, 3H, J=7 Hz), 1.16-1.50 (m, 10H), 1.51 (s, 6H), 1.70-1.77 (m, 2H), 3.91 (t, 2H, J=6 Hz), 4.06 (s, 2H), 4.60 (s, 2H), 6.80 (d, 2H, J=9 Hz), 7.04 (d, 1H, J=9 Hz), 7.12 (d, 2H, J=9 Hz), 8.04 (s, 1H), 8.23 (d, 1H, J=9 Hz). ESI-MS (m/z); 561 [M+H]$^+$.

Example 109

[4-(2-Aminoethoxy)-3-(4-n-octyloxylbenzyl)]benzoyl]phosphonic acid (compound 110)

The title compound was synthesized from 4-(2-t-butoxycarbonylaminoethoxy)-3-(4-n-octyloxybenzyl)benzaldehyde as a starting material by the same procedure as described in Example 43.

$^1$H-NMR (δ) CD$_3$OD; 0.90 (t, 3H, J=7 Hz), 1.31-1.46 (m, 10H), 1.71-1.77 (m, 2H), 3.39 (s, 2H), 3.93 (t, 2H, J=7 Hz), 4.03 (s, 2H), 4.37 (t, 2H, J=5 Hz), 6.82-6.84 (m, 2H), 7.12 (d, 2H, J=9 Hz), 7.15 (d, 1H, J=9 Hz), 7.96 (d, 1H, J=2 Hz), 8.24 (dd, 1H, J=2 Hz, 9 Hz). ESI-MS (m/z); 462 [M−H]$^-$.

Example 110

[4-(2-Methoxyethoxy)-3-(4-n-octyloxylbenzyl)]benzoyl]phosphonic acid (compound III)

The title compound was synthesized from 4-(2-methoxyethoxy)-3-(4-n-octyloxybenzyl)benzaldehyde as a starting material by the same procedure as described in Example 43.

$^1$H-NMR (δ) CD$_3$OD; 0.89 (t, 3H, J=7 Hz), 1.30-1.45 (m, 10H), 1.71-1.74 (m, 2H), 3.40 (s, 3H), 3.74 (t, 2H, J=7 Hz), 4.20-4.22 (m, 2H), 6.78 (dd, 2H, J=2 Hz, 7 Hz), 7.06 (d, 1H, J=9 Hz), 7.11 (dd, 2H, J=2 Hz, 9 Hz), 8.06 (d, 1H, J=2 Hz), 8.22 (dd, 1H, J=2 Hz, 9 Hz). ESI-MS (m/z); 477 [M−H]$^-$.

Example 111

[4-Hydroxy-3-[4-[5-(2-hydroxy-1,1-bishydroxymethylethylcarbamoyl)pentyloxy]benzyl]benzoyl]-phosphonic acid (compound 112)

The title compound was synthesized from 4-methoxymethyloxy-3-[4-[5-(2-methoxymethyloxy-1,1-bismethoxymethyloxyethylcarbamoyl)pentyloxy]benzyl]benzaldehyde as a starting material by the same procedure as described in Example 43.
¹H-NMR (δ) CD₃OD; 1.50-1.76 (m, 6H), 2.46 (t, 2H, J=7 Hz), 3.69-3.70 (2s, 6H), 3.87 (s, 2H), 3.92 (t, 2H, J=8 Hz), 6.79 (d, 2H, J=8 Hz), 6.92 (d, 1H, J=9 Hz), 7.10 (d, 2H, J=8 Hz), 7.92 (s, 1H), 8.03 (d, 1H, J=9 Hz). ESI-MS (m/z); 526 [M−H]⁻.

Example 112

[4-Hydroxy-3-[4-(6-oxo-morpholin-1-ylhexyloxy)benzyl]benzoyl]phosphonic acid (compound 113)

The title compound was synthesized from 4-methoxymethyloxy-3-[4-(6-oxo-morpholin-1-ylhexyloxy)benzyl]-benzaldehyde as a starting material by the same procedure as described in Example 43.
¹H-NMR (δ) CD₃OD; 1.52-1.55 (m, 2H), 1.62-1.70 (m, 2H), 1.74-1.79 (m, 2H), 2.41 (t, 2H, J=7 Hz), 3.48-3.57 (m, 4H), 3.59-3.64 (m, 4H), 3.88 (s, 2H), 3.93 (t, 2H, J=6 Hz), 6.76 (d, 2H, J=8 Hz), 6.81 (d, 1H, J=8 Hz), 7.12 (d, 2H, J=8 Hz), 7.99 (s, 1H), 8.18 (d, 1H, J=9 Hz). ESI-MS (m/z); 490 [M−H]

Example 113

[4-Hydroxy-3-[4-[5-(2-hydroxyethylcarbamoyl)pentyloxy]benzyl]benzoyl]phosphonic acid (compound 114)

The title compound was synthesized from 4-methoxymethyloxy-3-[4-[5-(2-methoxymethyloxyethoxycarbamoyl)pentyloxy]benzyl]benzaldehyde as a starting material by the same procedure as described in Example 43.
¹H-NMR (δ) CD₃OD; 1.46-1.50 (m, 2H), 1.65-1.69 (m, 2H), 1.74-1.77 (m, 2H), 2.22 (t, 2H, J=7 Hz), 3.26-3.31 (m, 2H), 3.57 (t, 2H, J=6 Hz), 3.88 (s, 2H), 3.92 (t, 2H, J=6 Hz), 6.77 (d, 2H, J=9 Hz), 6.81 (d, 1H, J=9 Hz), 7.12 (d, 2H, J=9 Hz), 7.99 (d, 1H, J=2 Hz), 8.19 (dd, 1H, J=2 Hz, 9 Hz). ESI-MS (m/z); 464 [M−H]⁻.

Example 114

[4-(2-Acetylaminoethoxy)-3-(4-n-octyloxybenzyl)benzoyl]phosphonic acid (compound 115)

The title compound was synthesized from 4-(2-acetylaminoethoxy)-3-(4-n-octyloxybenzyl)benzaldehyde as a starting material by the same procedure as described in Example 43.
¹H-NMR (δ) CD₃OD; 0.88 (t, 3H, J=7 Hz), 1.24-1.28 (m, 12H), 1.74 (s, 3H), 3.57 (m, 2H), 3.89-3.99 (m, 6H), 5.17 (m, 1H), 6.79-6.81 (m, 3H), 7.06 (d, 2H, J=9 Hz), 7.92 (m, 2H). ESI-MS (m/z); 487 [M−H]⁻.

Example 115

[4-(2-Methanesulfonylaminoethoxy)-3-(4-n-octyloxybenzyl)benzoyl]phosphonic acid (compound 116)

The title compound was synthesized from 4-(2-methanesulfonylaminoethoxy)-3-(4-n-octyloxybenzyl)benzaldehyde as a starting material by the same procedure as described in Example 43.
¹H-NMR (δ) CD₃OD; 0.88 (t, 3H, J=7 Hz), 1.28-1.44 (m, 10H), 1.72-1.77 (m, 2H), 2.82 (s, 3H), 3.41-3.45 (m, 2H), 3.91-3.95 (m, 2H), 3.94 (s, 2H), 4.11-4.13 (m, 2H), 6.83 (d, 2H, J=9 Hz), 6.90 (d, 1H, J=9 Hz), 7.04 (d, 2H, J=9 Hz), 8.16 (s, 1H), 8.33 (d, 1H, J=7 Hz). ESI-MS (m/z); 540 [M−H]⁻.

Example 116

[3-(4-n-Octyloxybenzyl)-4-(2-uredoethoxy)benzoyl]phosphonic acid (compound 117)

The title compound was synthesized from 3-(4-n-octyloxybenzyl)-4-(2-uredoethoxy)benzaldehyde as starting material by the same procedure as described in Example 43.
¹H-NMR (δ) DMSO-d6; 0.84 (m, 3H), 1.17-1.38 (m, 10H), 1.66-1.68 (m, 2H), 3.88 (s, 2H), 3.84-4.07 (m, 6H), 5.56 (s, 1H), 6.77-6.80 (m, 2H), 6.97 (m, 1H), 7.11-7.13 (m, 2H), 7.87-7.89 (m, 1H), 8.27 (d, 1H, J=6.6 Hz), 8.75 (s, 1H). ESI-MS (m/z); 504 [M−H]⁻.

Example 117

[4-Hydroxy-3-[4-[3'-(5-hydroxyhexyoxy)biphenyl-3-yloxy]benzyl]benzoyl]phosphonic acid (compound 118)

The title compound was synthesized from 4-methoxymethyloxy-3-[4-[3'-(5-methoxymethyloxyhexyoxy)biphenyl-3-yloxy]benzyl]benzaldehyde as a starting material by the same procedure as described in Example 43.
¹H-NMR (δ) CDCl₃; 0.88-1.26 (m, 9H), 1.41-1.48 (m, 2H), 1.75 (m, 2H), 3.87 (s, 2H), 3.99 (m, 3H), 4.33 (m, 1H), 6.72-7.44 (m, 13H), 7.69-7.86 (m, 2H). ESI-MS (m/z); 574 [M−H]⁻.

Example 118

[4-Hydroxy-3-[4-(6-oxo-piperazine-1-ylhexyloxy)benzyl]benzoyl]phosphonic acid (compound 119)

The title compound was synthesized from 4-[6-[4-(5-formyl-2-methoxymethyloxybenzyl)phenoxy]hexanoyl]piperazine-1-carboxylic acid t-butylester as a starting material by the same procedure as described in Example 43.
¹H-NMR (δ) CD₃OD; 1.50-1.57 (m, 2H), 1.64-1.71 (m, 2H), 1.75-1.82 (m, 2H), 2.46 (t, 2H, J=7 Hz), 3.21-3.23 (m, 4H), 3.78-3.80 (m, 4H), 3.89 (s, 2H), 3.95 (t, 2H, J=6 Hz), 6.79 (d, 2H, J=9 Hz), 6.86 (d, 1H, J=9 Hz), 7.12 (d, 2H, J=9 Hz), 7.94 (d, 1H, J=2 Hz), 8.06 (dd, 1H, J=2 Hz, 9 Hz). ESI-MS (m/z); 489 [M−H]⁻.

Example 119

[4-Hydroxy-6-methyl-3-(4-n-octyloxybenzyl)benzoyl]phosphonic acid (compound 120)

The title compound was synthesized from 4-methoxymethyloxy-6-methyl-3-(n-octyoxybenzyl)benzaldehyde as a starting material by the same procedure as described in Example 43.
¹H-NMR (δ) CD₃OD; 4.21 (s, 2H), 6.92-7.03 (m, 4H), 7.26-7.42 (m, 8H), 7.53-7.56 (m, 2H), 8.19 (d, 1H, J=4 Hz). ESI-MS (m/z); 449 [M−H]⁻.

Example 120

{5-[4-(3-Phenyl)phenoxybenzyl]thiophene-2-carbonyl}phosphonic acid (compound 121)

The title compound was synthesized from 5-[4-(3-phenyl)phenoxybenzyl]thiophene-2-carbonylchloride as a starting material by the same procedure as described in Example 70.
$^1$H-NMR (δ) CD$_3$OD; 4.21 (s, 2H), 6.92-7.03 (m, 4H), 7.26-7.42 (m, 8H), 7.53-7.56 (m, 2H), 8.19 (d, 1H, J=4 Hz). ESI-MS (m/z); 449 [M−H]$^-$.

Example 121

{5-[4-(4-Phenyl)phenoxybenzyl]thiophene-2-carbonyl}phosphonic acid (compound 122)

The title compound was synthesized from 5-[4-(4-phenyl)phenoxybenzyl]thiophene-2-carbonylchloride as a starting material by the same procedure as described in Example 70.
$^1$H-NMR (δ) CD$_3$OD; 4.21 (s, 2H), 6.97-7.04 (m, 5H), 7.26-7.28 (m, 3H), 7.39 (t, 2H, J=8 Hz), 7.56-7.59 (m, 4H), 8.19 (d, 1H, J=4 Hz). ESI-MS (m/z); 449 [M−H]$^-$.

The chemical structures of compounds 1~99 and compounds 101~122 are shown in Table 3~11.

TABLE 3

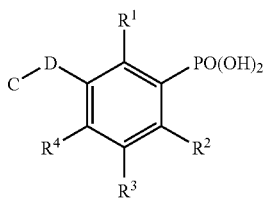

| Compd. No | R$^1$ | R$^2$ | R$^3$ | R$^4$ | C | D |
|---|---|---|---|---|---|---|
| 1 | H | OH | H | H | 4-Ethylphenyl | CH$_2$ |
| 2 | H | OMe | H | OMe | 4-Ethylphenyl | CH$_2$ |
| 3 | H | OMe | H | H | 4-Ethylphenyl | CH$_2$ |

TABLE 4

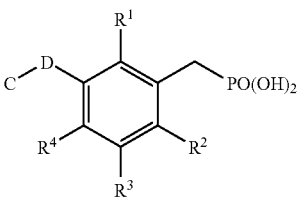

| Compd. No | R$^1$ | R$^2$ | R$^3$ | R$^4$ | C | D |
|---|---|---|---|---|---|---|
| 4 | H | OH | H | H | 4-Ethylphenyl | CH$_2$ |
| 5 | H | H | H | OH | 4-Ethylphenyl | CH$_2$ |
| 6 | H | H | H | OCH$_2$CH$_2$OH | 4-Ethylphenyl | CH$_2$ |
| 7 | H | F | H | H | 4-Ethylphenyl | CH$_2$ |
| 8 | H | Cl | H | H | 4-Ethylphenyl | CH$_2$ |
| 9 | H | Me | H | H | 4-Ethylphenyl | CH$_2$ |
| 10 | H | OMe | H | H | 4-Ethylphenyl | CH$_2$ |
| 11 | H | OMe | H | OMe | 4-Ethylphenyl | CH$_2$ |
| 12 | H | H | H | Cl | 4-Ethylphenyl | CH$_2$ |
| 13 | H | H | H | OMe | 4-Ethylphenyl | CH$_2$ |
| 14 | H | H | H | OEt | 4-Ethylphenyl | CH$_2$ |
| 15 | H | H | H | O-nPr | 4-Ethylphenyl | CH$_2$ |
| 16 | H | H | H | O-iPr | 4-Ethylphenyl | CH$_2$ |
| 17 | H | H | H | OBn | 4-Ethylphenyl | CH$_2$ |

TABLE 4-continued

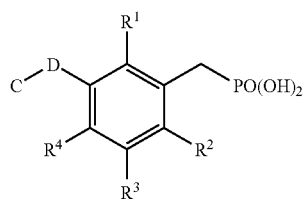

| Compd. No | R$^1$ | R$^2$ | R$^3$ | R$^4$ | C | D |
|---|---|---|---|---|---|---|
| 18 | H | H | H | OH | 2-Ethoxyphenyl | CH$_2$ |
| 19 | H | H | H | OH | 3-Ethoxyphenyl | CH$_2$ |
| 20 | H | H | H | OH | 4-Ethoxyphenyl | CH$_2$ |
| 21 | H | OH | H | H | 4-Ethoxyphenyl | CH$_2$ |
| 22 | H | H | H | OCH$_2$CH$_2$OH | 4-Ethoxyphenyl | CH$_2$ |
| 23 | H | H | H | F | 4-Ethoxyphenyl | CH$_2$ |
| 24 | H | H | H | Cl | 4-Ethoxyphenyl | CH$_2$ |
| 25 | H | OMe | H | OMe | 4-Ethoxyphenyl | CH$_2$ |
| 26 | H | H | H | OH | 4-Ethoxyphenyl | O |
| 27 | H | OH | H | H | 4-Ethoxyphenyl | O |
| 28 | H | H | H | Cl | 4-t-Butylphenyl | CH$_2$ |
| 29 | H | OH | H | H | 4-t-Butylphenyl | CH$_2$ |
| 30 | H | H | H | Cl | Naphthalen-2-yl | CH$_2$ |
| 31 | H | OH | H | H | Naphthalen-2-yl | CH$_2$ |
| 32 | H | H | H | Cl | Benzofuran-2-yl | CH$_2$ |
| 33 | H | H | H | Cl | Benzo[b]thiophen-2-yl | CH$_2$ |

TABLE 5

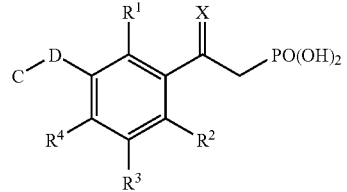

| Compd. No | R$^1$ | R$^2$ | R$^3$ | R$^4$ | C | D | X |
|---|---|---|---|---|---|---|---|
| 34 | H | OH | H | H | 4-Ethylphenyl | CH$_2$ | H$_2$ |
| 35 | H | OMe | H | H | 4-Ethylphenyl | CH$_2$ | H$_2$ |
| 36 | H | H | H | OH | 4-Ethoxyphenyl | CH$_2$ | O |

TABLE 6

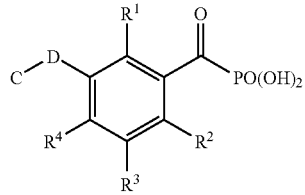

| Compd. No | R$^1$ | R$^2$ | R$^3$ | R$^4$ | C | D |
|---|---|---|---|---|---|---|
| 37 | H | H | H | OH | 4-Ethylphenyl | CH$_2$ |
| 38 | H | H | H | OH | 4-Ethoxyphenyl | CH$_2$ |
| 39 | H | H | H | OH | 4-Ethoxyphenyl | O |
| 40 | H | H | H | OH | 4-Ethoxyphenyl | CH$_2$CH$_2$ |
| 41 | H | H | H | OH | 4-Ethoxypheny | CH$_2$O |
| 42 | H | H | H | OH | 4-Methylthiophenyl | CH$_2$ |

TABLE 6-continued

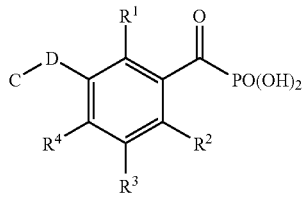

| Compd. No | R¹ | R² | R³ | R⁴ | C | D |
|---|---|---|---|---|---|---|
| 43 | H | H | H | OH | 4-Hydroxyphenyl | CH₂ |
| 44 | H | H | H | OH | 4-Methoxyphenyl | CH₂ |
| 45 | H | H | H | OH | 4-n-Propoxyphenyl | CH₂ |
| 46 | H | H | H | OH | 4-i-Propoxyphenyl | CH₂ |
| 47 | H | H | H | OCH₂CH₂OH | 4-i-Propoxyphenyl | CH₂ |
| 48 | H | H | H | OH | 4-n-Butoxyphenyl | CH₂ |
| 49 | H | H | H | OH | 4-Phenoxyphenyl | CH₂ |
| 50 | H | H | H | OCH₂CH₂OH | 4-Phenoxyphenyl | CH₂ |
| 51 | H | H | H | OH | 4-n-Octyloxyphenyl | CH₂ |
| 52 | H | H | H | OH | 4-n-Hexyloxyphenyl | CH₂ |
| 53 | H | H | H | OH | 4-(2-Hydroxyethoxy)phenyl | CH₂ |
| 54 | H | H | H | OH | Benzo[b]thiophen-2-yl | CH₂ |
| 55 | H | H | H | OCH₂CH₂OH | Benzo[b]thiophen-2-yl | CH₂ |
| 56 | H | H | H | OH | 1,3-Benzodioxol-5-yl | CH₂ |
| 57 | H | H | H | OCH₂OH₂OH | 4-Ethoxyphenyl | CH₂ |
| 58 | H | H | H | OH | 4-(2-Ethoxyethoxy)phenyl | CH₂ |
| 59 | H | H | H | OH | 4-Methylsulfonylphenyl | CH₂ |
| 60 | H | H | H | OCH₂CH₂OH | 4-Methylthiophenyl | CH₂ |
| 61 | H | H | H | OH | 4-Ethylthiophenyl | CH₂ |
| 62 | H | H | H | OCH₂CH₂OH | 4-Ethylthiophenyl | CH₂ |
| 63 | H | H | H | OH | 4-Ethylsulfonylphenyl | CH₂ |

TABLE 7

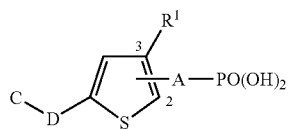

| Compd. No | R¹ | A | Position | C | D |
|---|---|---|---|---|---|
| 64 | H | bond | 2 | 4-Ethoxyphenyl | CH₂ |
| 65 | H | CH₂ | 2 | 4-Ethoxyphenyl | CH₂ |
| 66 | H | bond | 2 | Benzofuran-2-yl | CH₂ |
| 67 | H | CH₂ | 2 | Benzofuran-2-yl | CH₂ |
| 68 | H | bond | 2 | Benzo[b]thiophen-2-yl | CH₂ |
| 69 | H | CH₂ | 2 | Benzo[b]thiophen-2-yl | CH₂ |
| 70 | H | CO | 2 | 4-Ethoxyphenyl | CH₂ |
| 71 | Me | CO | 2 | 4-Ethoxyphenyl | CH₂ |
| 72 | H | CO | 3 | 4-Ethoxyphenyl | CH₂ |
| 73 | H | CO | 2 | 4-Methylthiophenyl | CH₂ |
| 74 | H | CO | 2 | 4-Methylsulfonylphenyl | CH₂ |
| 75 | H | CO | 2 | 4-Chlorophenyl | CH₂ |
| 76 | H | CO | 2 | 4-Ethylthiophenyl | CH₂ |
| 77 | H | CO | 2 | 4-Phenoxyphenyl | CH₂ |
| 78 | H | CO | 2 | 4-Benzyloxyphenyl | CH₂ |
| 79 | H | CO | 2 | 4-i-Propoxyphenyl | CH₂ |
| 80 | H | CO | 2 | n-Butoxyphenyl | CH₂ |
| 81 | H | CO | 2 | n-Pentyloxyphenyl | CH₂ |
| 82 | H | CO | 2 | n-Octyloxyphenyl | CH₂ |
| 83 | H | CO | 2 | n-Tridecanyloxyphenyl | CH₂ |
| 84 | H | CO | 2 | 4-(2-Ethoxyethoxy)phenyl | CH₂ |
| 85 | H | CO | 2 | 4-(Carboxymethoxy)phenyl | CH₂ |

TABLE 7-continued

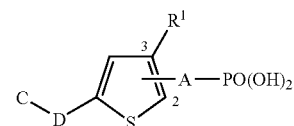

| Compd. No | R¹ | A | Position | C | D |
|---|---|---|---|---|---|
| 86 | H | CO | 2 | 4-(Carbamoylmethoxy)phenyl | CH₂ |
| 87 | H | CO | 2 | 4-[2-(Morpholin-1-yl)ethoxy]phenyl | CH₂ |
| 88 | H | CO | 2 | Benzo[b]thiophen-2-yl | CH₂ |

TABLE 8

Compound 89

Compound 90

Compound 91

TABLE 9

| Compd. No | R¹ | R² | R³ | R⁴ | C | D |
|---|---|---|---|---|---|---|
| 92 | H | H | H | OH | 5-Ethylthiophen-2-yl | CH₂ |
| 93 | H | H | H | OCH₂CH₂OCH₃ | 4-Phenoxyphenyl | CH₂ |
| 94 | H | H | H | OCH₂COOCH₃ | 4-Phenoxyphenyl | CH₂ |
| 95 | H | H | H | OCH₂COOH | 4-Phenoxyphenyl | CH₂ |
| 96 | H | H | H | OCH₂CONH₂ | 4-Phenoxyphenyl | CH₂ |
| 97 | H | H | H | OCH₂CH₂NH₂ | 4-Phenoxyphenyl | CH₂ |
| 98 | H | H | H | O(CH₂)₄OH | 4-Ethoxyphenyl | CH₂ |
| 99 | H | H | H | O(CH₂)₆OH | 4-Ethoxyphenyl | CH₂ |

TABLE 10

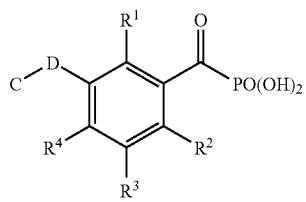

| Compd. No | $R^1$ | $R^2$ | $R^3$ | $R^4$ | C | D |
|---|---|---|---|---|---|---|
| 101 | H | H | H | OH | 4-(3-Phenyl)phenoxyphenyl | $CH_2$ |
| 102 | H | H | H | OH | 4-(4-Phenyl)phenoxyphenyl | $CH_2$ |
| 103 | H | H | H | $OCH_2CH_2OCH_3$ | 4-(3-Phenyl)phenoxyphenyl | $CH_2$ |
| 104 | H | H | H | $OCH_2CH_2OH$ | 4-(3-Phenyl)phenoxyphenyl | $CH_2$ |
| 105 | H | H | H | $OCH_2CONH_2$ | 4-(3-Phenyl)phenoxyphenyl | $CH_2$ |
| 106 | H | H | H | $OCH_2CH_2OH$ | 4-n-Octyloxyphenyl | $CH_2$ |
| 107 | H | H | H | $OCH_2CONHCH_2CH_2OH$ | 4-n-Octyloxyphenyl | $CH_2$ |
| 108 | H | H | H | $OCH_2CONH_2$ | 4-n-Octyloxyphenyl | $CH_2$ |
| 109 | H | H | H | $OCH_2CONHC(CH_3)_2CONH_2$ | 4-n-Octyloxyphenyl | $CH_2$ |
| 110 | H | H | H | $OCH_2CH_2NH_2$ | 4-n-Octyloxyphenyl | $CH_2$ |
| 111 | H | H | H | $OCH_2CH_2OCH_3$ | 4-n-Octyloxyphenyl | $CH_2$ |
| 112 | H | H | H | OH | Ph-O—$(CH_2)_5CONHC(CH_2OH)_3$ | $CH_2$ |
| 113 | H | H | H | OH | Ph-O—$(CH_2)_5CO$-1-morpholine | $CH_2$ |
| 114 | H | H | H | OH | Ph-O—$(CH_2)_5CONHCH_2CH_2OH$ | $CH_2$ |
| 115 | H | H | H | $OCH_2CH_2NHCOCH_3$ | 4-n-Octyloxyphenyl | $CH_2$ |
| 116 | H | H | H | $OCH_2CH_2NHSO_2CH_3$ | 4-n-Octyloxyphenyl | $CH_2$ |
| 117 | H | H | H | $OCH_2CH_2NHCONH_2$ | 4-n-Octyloxyphenyl | $CH_2$ |
| 118 | H | H | H | OH | 5-(3'-Phenoxybiphenyl-3-yloxy)-pentan-1-ol | $CH_2$ |
| 119 | H | H | H | OH | 4-(6-oxo-piperadin-1-ylhexyl-oxy)phenyl | $CH_2$ |
| 120 | $CH_3$ | H | H | OH | 4-n-Octyloxyphenyl | $CH_2$ |

TABLE 11

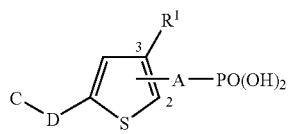

| Compd. No | $R^1$ | A | Position | C | D |
|---|---|---|---|---|---|
| 121 | H | CO | 2 | 4-(3-Phenyl)phenoxyphenyl | $CH_2$ |
| 122 | H | CO | 2 | 4-(4-Phenyl)phenoxyphenyl | $CH_2$ |

The invention claimed is:

1. A compound of the formula;

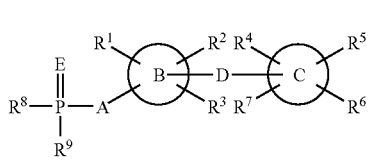

(I)

wherein:

A is selected from —$(CH_2)_n$— or —CO—,

B is a heterocycle or fused heterocycle compound containing a sulfur atom,

C is a benzene ring,

D is selected from —$(CH_2)_{(n+1)}$—,

E is an oxygen atom, and

P is a phosphine atom, wherein $R^1 \sim R^7$ may each be the same or different and are selected from a hydrogen atom, a halogen atom, a nitro group, a cyano group, a straight-chain or branched-chain alkyl group of C1-20, a straight-chain or branched-chain haloalkyl group of C1-20, a straight-chain or branched-chain haloalkoxy group of C1-20, an unsubstituted or substituted aryl group, a heterocycle or fused heterocycle containing a nitrogen, oxygen or sulfur atom, —O—$(CH_2)_{(n+1)}$—OH, an —$(CH_2)_n$—O-straight-chain or branched-chain alkyl group of C1-20, an —$(CH_2)_n$-unsubstituted or substituted aryl group, an —O—$(CH_2)_{(n+1)}$-unsubstituted or substituted aryl group, an —$(CH_2)_n$—$S(O)_o$-straight-chain or branched-chain alkyl group of C1-20, an —O—$(CH_2)_{(n+1)}$—$S(O)_o$-straight-chain or branched-chain alkyl group of C1-20, an —$(CH_2)_n$—$S(O)_o$-unsubstituted or substituted aryl group, an —O—$(CH_2)_{(n+1)}$—$S(O)_o$-unsubstituted or substituted aryl group, —$(CH_2)_n$—$COOR^{11}$, —O—$(CH_2)_n$—$COOR^{11}$, —$(CH_2)_n$—$SO_3R^{11}$, —O—$(CH_2)_n$—$SO_3R^{11}$, —$(CH_2)_n$—$CONR^{12}R^{13}$, —O—$(CH_2)_n$—$CONR^{12}R^{13}$, —$(CH_2)_n$—$SO_2NR^{12}R^{13}$, —O—$(CH_2)_n$—$SO_2NR^{12}R^{13}$, an —$(CH_2)_n$—CO-branched-chain alkyl group of C1-20, an —O—$(CH_2)_n$—CO-branched-chain alkyl group of C1-20, an —$(CH_2)_n$—CO-unsubstituted or substituted aryl group, an —O—$(CH_2)_n$—CO-unsubstituted or substituted aryl group, an amino group, a monosubstituted amino group, a disubstituted amino group, a trisubstituted amino group, a tetrasubstituted amino group, an —O—$(CH_2)_{(n+1)}$—O— amino group, an —O—$(CH_2)_{(n+1)}$—O-monosubstituted amino group, an —O—$(CH_2)_{(n+1)}$—O-disubstituted amino group, an —O—$(CH_2)_{(n+1)}$—O— trisubstituted amino group, an —O—$(CH_2)_{(n+1)}$—

O-tetrasubstituted amino group, a substituted amino group with a substituent selected from a straight-chain or branched-chain alkyl group of C1-20, a straight-chain or branched-chain alkanoyl group of C1-20, an unsubstituted or substituted arylcarbonyl group, a straight-chain or branched-chain alkylsulfonyl group of C1-20, an unsubstituted or substituted arylsulfonyl group or straight-chain or branched-chain alkoxycarbonyl group of C1-20, $R^8$ and $R^9$ may be the same or different and each are selected from a hydroxyl group and a straight-chain or branched-chain alkoxy group of C1-20, $R^1$ and $R^2$ and $R^4$ and $R^5$ can join with a neighboring carbon atom to a 5-7 member saturated or unsaturated hydrocarbon ring or a 5-6 membered fused heterocycle compound, $R^1$, $R^2$ and $R^3$ are each not a hydrogen atom if B is a benzene ring, $R^{11}$ is a hydrogen atom or a straight-chain or branched-chain alkyl group of C1-20, $R^{12}$ and $R^{13}$ are each a hydrogen atom or a straight-chain or branched-chain alkyl group of C1-20, n and m are an integer of from 0-10 and o is an integer of from 0-2, and pharmaceutically acceptable salts thereof.

2. A pharmaceutical composition comprising a compound of claim 1.

3. A compound of the formula (I) according to claim 1 and the pharmaceutically acceptable salts thereof wherein A is —CO—, B ring is heterocycle or fused heterocycle containing a sulfur atom.

\* \* \* \* \*